United States Patent
Osaki et al.

(10) Patent No.: US 12,214,084 B2
(45) Date of Patent: Feb. 4, 2025

(54) ENTERIC HARD CAPSULE

(71) Applicant: QUALICAPS CO., LTD., Nara (JP)

(72) Inventors: Yoshiro Osaki, Nara (JP); Makoto Aso, Nara (JP); Toshimitsu Usui, Nara (JP); Mamoru Honda, Nara (JP)

(73) Assignee: QUALICAPS CO., LTD., Nara (JP)

( * ) Notice: Subject to any disclaimer, the term of this patent is extended or adjusted under 35 U.S.C. 154(b) by 26 days.

(21) Appl. No.: 16/628,742

(22) PCT Filed: Jul. 11, 2018

(86) PCT No.: PCT/JP2018/026216
§ 371 (c)(1),
(2) Date: Jul. 1, 2020

(87) PCT Pub. No.: WO2019/013260
PCT Pub. Date: Jan. 17, 2019

(65) Prior Publication Data
US 2020/0375910 A1    Dec. 3, 2020

(30) Foreign Application Priority Data

Jul. 11, 2017  (JP) ................................ 2017-135666
Mar. 6, 2018  (JP) ................................ 2018-039184

(51) Int. Cl.
| | | |
|---|---|---|
| *A61K 9/48* | (2006.01) | |
| *A61K 9/00* | (2006.01) | |
| *A61K 47/32* | (2006.01) | |
| *A61K 47/38* | (2006.01) | |

(52) U.S. Cl.
CPC .......... *A61K 9/4891* (2013.01); *A61K 9/0053* (2013.01); *A61K 9/4816* (2013.01); *A61K 47/32* (2013.01); *A61K 47/38* (2013.01)

(58) Field of Classification Search
CPC .. A61K 9/4891; A61K 9/0053; A61K 9/4816; A61K 47/32; A61K 47/38
See application file for complete search history.

(56) References Cited

U.S. PATENT DOCUMENTS

| | | | |
|---|---|---|---|
| 630,966 | A | 8/1899 | Bohm et al. |
| 2,196,768 | A | 4/1940 | Hiatt et al. |
| 2,718,667 | A | 9/1955 | Malm et al. |
| 3,826,666 | A | 7/1974 | Hirai et al. |
| 3,927,195 | A | 12/1975 | Messora |
| 4,138,013 | A | 2/1979 | Okajima |
| 4,365,060 | A | 12/1982 | Onda et al. |
| 4,644,031 | A | 2/1987 | Lehmann et al. |
| 5,644,011 | A | 7/1997 | Lehmann et al. |
| 5,756,123 | A | 5/1998 | Yamamoto et al. |
| 6,309,666 | B1 | 10/2001 | Hatano et al. |
| 7,094,425 | B2 | 8/2006 | Scott et al. |
| 9,107,451 | B2 | 8/2015 | Skalsky et al. |
| 2003/0104047 | A1 | 6/2003 | Chen et al. |
| 2005/0079216 | A1 | 4/2005 | Petereit et al. |
| 2005/0152977 | A1 | 7/2005 | Petereit et al. |
| 2006/0177496 | A1 | 8/2006 | McAllister et al. |
| 2010/0074947 | A1 | 3/2010 | Brown et al. |
| 2012/0161364 | A1 | 6/2012 | Son et al. |
| 2013/0203868 | A1* | 8/2013 | Son ...................... A61K 9/4816 514/781 |
| 2013/0295188 | A1* | 11/2013 | Cade ...................... A61K 47/10 424/494 |
| 2017/0119681 | A1 | 5/2017 | Bravo Gonzalez et al. |

FOREIGN PATENT DOCUMENTS

| | | |
|---|---|---|
| CA | 2 769 046 | 2/2011 |
| CN | 102119026 | 7/2011 |
| CN | 102198114 | 9/2011 |
| CN | 106456559 | 2/2017 |
| DE | 2135073 | 2/1973 |
| DE | 2157435 | 6/1973 |
| EP | 2 283 830 | 2/2011 |
| EP | 3332775 | 6/2018 |
| GB | 2 087 235 | 5/1982 |

(Continued)

OTHER PUBLICATIONS

Li et al. The use of hypromellose in oral drug delivery. Journal of Pharmacy and Pharmacology 2005, 57:533-546. (Year: 2005).*
Ashland. Product Grades Available. 20016, 4 pages. (Year: 2016).*
International Search Report issued Sep. 17, 2019 in International (PCT) Application No. PCT/JP2019/024713.
Moghimipour et al., "In vivo evaluation of pH and time-dependent polymers as coating agent for colonic delivery using central composite design", Journal of Drug Delivery Science and Technology, 2018, vol. 43, pp. 50-56.
Zhang et al., "Formulation and preparation of rabeprazole sodium enteric-coated capsules", Central South Pharmacy, 2016, vol. 14, No. 7, pp. 712-716, with English Abstract.

(Continued)

*Primary Examiner* — Robert A Wax
*Assistant Examiner* — Olga V. Tcherkasskaya
(74) *Attorney, Agent, or Firm* — Wenderoth, Lind & Ponack, L.L.P.

(57) ABSTRACT

An object of the present disclosure is providing a hard capsule made of a hard capsule film having enteric properties that can be molded by a cold gel method. An enteric hard capsule comprises a film containing a first component and a second component, and further containing at least one component selected from the group consisting of a third component, a fourth component, and a fifth component, wherein the first component is a nonionic water-soluble cellulose compound having a viscosity value within a range of from 100 mPa·s to 100,000 mPa·s, the second component is an enteric methacrylic acid copolymer, the third component is an enteric cellulose compound, wherein the fourth component is a water-insoluble (meth)acrylic acid alkyl ester copolymer, and the fifth component is at least one kind selected from the group consisting of polyvinyl alcohol, a plasticizer, and a surfactant.

18 Claims, 8 Drawing Sheets

(56) References Cited

FOREIGN PATENT DOCUMENTS

| | | |
|---|---|---|
| JP | 47-003547 | 2/1972 |
| JP | 53-052619 | 5/1978 |
| JP | 55-136061 | 10/1980 |
| JP | 57-032230 | 2/1982 |
| JP | 57-109716 | 7/1982 |
| JP | 60-190725 | 9/1985 |
| JP | 62-10023 | 1/1987 |
| JP | 8-81392 | 3/1996 |
| JP | 8-208458 | 8/1996 |
| JP | 2001-506692 | 5/2001 |
| JP | 2003-325642 | 11/2003 |
| JP | 2004-522746 | 7/2004 |
| JP | 2005-194218 | 7/2005 |
| JP | 2005-526546 | 9/2005 |
| JP | 2006-016372 | 1/2006 |
| JP | 2006-052819 | 2/2006 |
| JP | 2006-528197 | 12/2006 |
| JP | 2007-500176 | 1/2007 |
| JP | 2009-507875 | 2/2009 |
| JP | 2009-196961 | 9/2009 |
| JP | 2009-532331 | 9/2009 |
| JP | 2009-538315 | 11/2009 |
| JP | 2010-202550 | 9/2010 |
| JP | 2010-270039 | 12/2010 |
| JP | 2011-500871 | 1/2011 |
| JP | 2011-503048 | 1/2011 |
| JP | 2013-500293 | 1/2013 |
| JP | 2013-504565 | 2/2013 |
| JP | 2013-540149 | 10/2013 |
| JP | 2013-540806 | 11/2013 |
| JP | 2015-515962 | 6/2015 |
| JP | 2015-518005 | 6/2015 |
| WO | 98/27151 | 6/1998 |
| WO | 02/060384 | 8/2002 |
| WO | 02/060385 | 8/2002 |
| WO | 2004/010978 | 2/2004 |
| WO | 2005/011647 | 2/2005 |
| WO | 2007/031326 | 3/2007 |
| WO | 2007/103200 | 9/2007 |
| WO | 2007/139886 | 12/2007 |
| WO | 2008/050209 | 5/2008 |
| WO | 2009/087483 | 7/2009 |
| WO | 2011/012369 | 2/2011 |
| WO | 2011/036601 | 3/2011 |
| WO | 2012/053703 | 4/2012 |
| WO | 2012/056321 | 5/2012 |
| WO | 2013/164121 | 11/2013 |
| WO | 2013/164122 | 11/2013 |
| WO | 2017/022248 | 2/2017 |
| WO | 2019/013260 | 1/2019 |

OTHER PUBLICATIONS

Ranip et al., "Development and In-Vitro Drug Release Studies of Satranidazole Capsules for Colon Specific Drug Delivery", Asian Journal of Pharmaceutical and Clinical Research, 2014, Vo. 7, Issue 3, pp. 203-211.

Nigam et al., "Effect of Wheat ARF Treatment on the Baking Quality of Whole Wheat Flours of the Selected Varieties of Wheat", Journal of Applied Pharmaceutical Science, 2013, vol. 3, pp. 139-145.

Sharma et al., "Solid-State Interactions at the Core-Coat Interface: Physicochemical Characterization of Enteric-Coated Omeprazole Pellets Without a Protective Sub-Coat", AAPS PharmSciTech, 2015, vol. 16, No. 4, pp. 934-943.

"Formulation Study of Lanzoprazole Fast-disintegrating Tablets Containing Enteric-coated Microgranules", J. Soc. Powder Technol., Japan, 2005, vol. 42, pp. 811, with English-language translation.

Tagawa et al., "Adsorption Treatment of Polymer at Lower Critical Solution Temperature (LCST) and its Effect on The Stability of Polystyrene Latices", Japanese Journal of Polymer Science and Technology, 1983, vol. 40, pp. 273-278, with English Abstract.

Wong et al., "Flocculation of an Aqueous Colloidal Ethyl Cellulose Dispersion (Aquacoat) with a Water-Soluble Polymer, Hydroxypropyl Methylcellulose", Eur. J. Pharm. Biopharm., 1996, vol. 42, pp. 12-15.

Ohyagi et al., "Synergetic Role of Hypromellose and Methacrylic Acid Copolymer in the Dissolution Improvement of Amorphous Solid Dispersions", Journal of Pharmaceutical Science, 2017, vol. 106, pp. 1042-1050.

Office Action issued Jul. 14, 2021 in corresponding Indian Application No. 202047005393.

Microcarrier drug delivery system, 2009, p. 408, with English translation.

Cole et al., "Enteric coated HPMC capsules designed to achieve intestinal targeting", International Journal of Pharmaceutics, 2002, vol. 231, pp. 83-95.

Dvorackova et al., "Coated hard capsules as the pH-dependent drug transport systems to ileo-colonic compartment", Drug Development and Industrial Pharmacy, 2011, vol. 37, No. 10, pp. 1131-1140.

Zema et al., "Gastroresistant capsular device prepared by injection molding", International Journal of Pharmaceutics, 2013, vol. 440, pp. 264-272.

Hibino et al., "Development of Formulation Considering the Intake Easiness (Part 3)—Film Coating to Granules—", 2008 Mie Prefectural Industrial Research Institute Research Report, No. 33, 2009, pp. 59-64, with partial English translation.

Brogmann et al., "Enteric Targeting Through Enteric Coating", Drug Targeting Technology, CRC press, 2001, Part 1, pp. 1-29.

Felton et al., "Mechanical Properties of Polymeric Films Prepared from Aqueous Dispersions", Aqueous Polymeric Coatings For Pharmaceutical Dosage Forms, 4th edition, CRC Press, 2017, Chapter 4, Chapter 9, Chapter 10 (Table 10.5).

Ronbunshu et al., "Temperature-Viscosity Relationships of Aqueous Solutions of Cellulose Ethers", Mar. 1981, vol. 38, No. 3, pp. 133-137, with English abstract.

Klug et al., "Some Properties of Water-Soluble Hydroxyalkyl Cellulose and Their Derivatives", J. Polymer Sci: Part C, 1971, No. 36, pp. 491-508.

Extended European Search Report issued May 26, 2020 in corresponding European Application No. 18832265.5.

International Search Report issued Sep. 4, 2018 in International (PCT) Application No. PCT/JP2018/026216.

Extended European Search Report issued Jun. 3, 2022 in European Patent Application No. 19822248.1.

Office Action issued Feb. 29, 2024, for Chinese Patent Application No. 201980053922.X, with English translation.

* cited by examiner

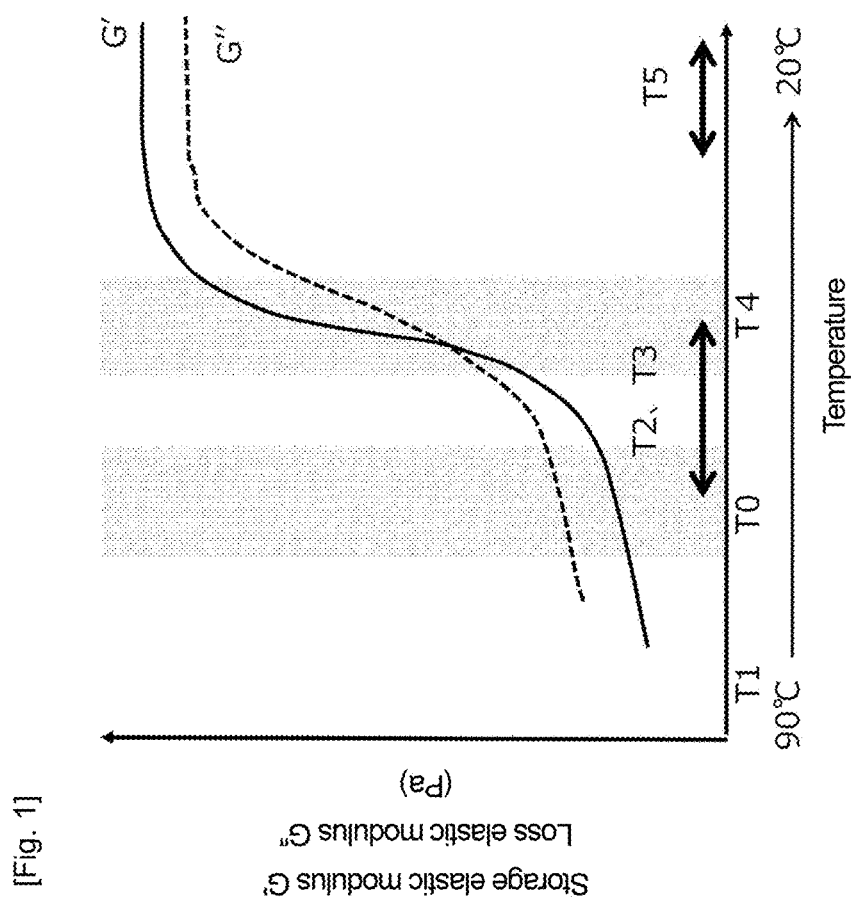

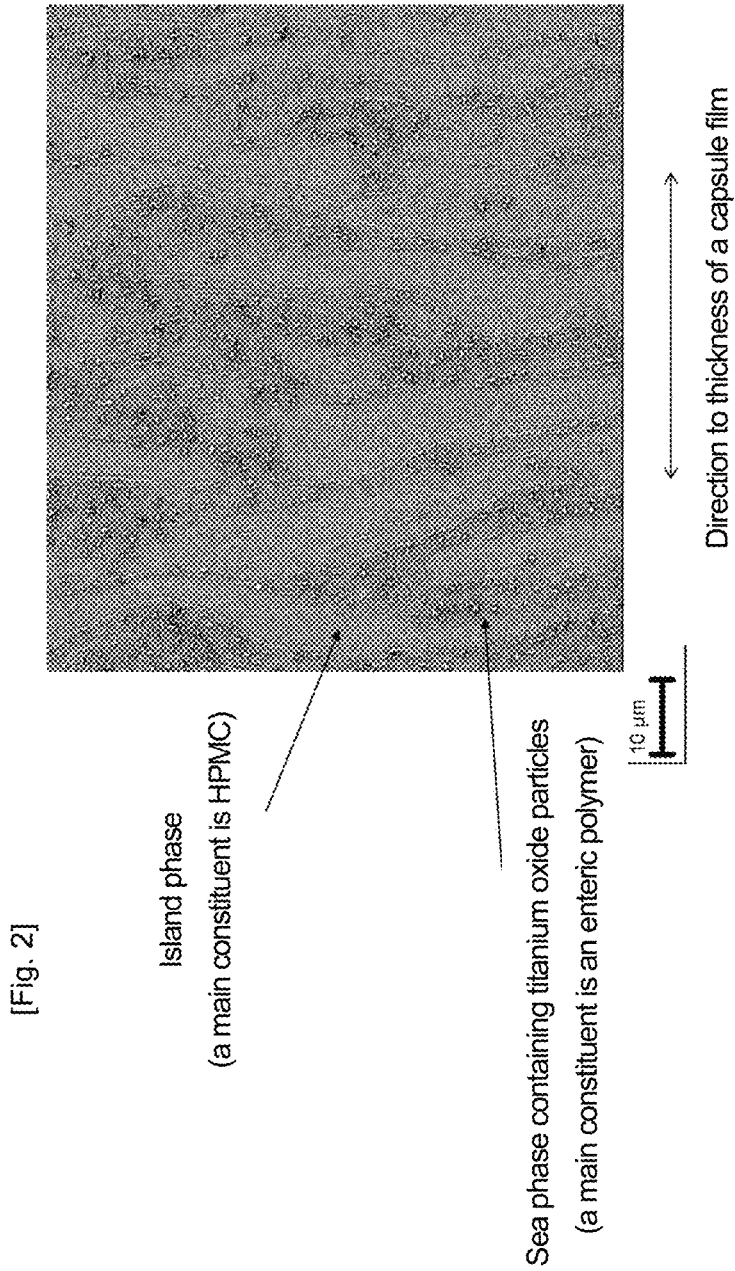

[Fig. 3]
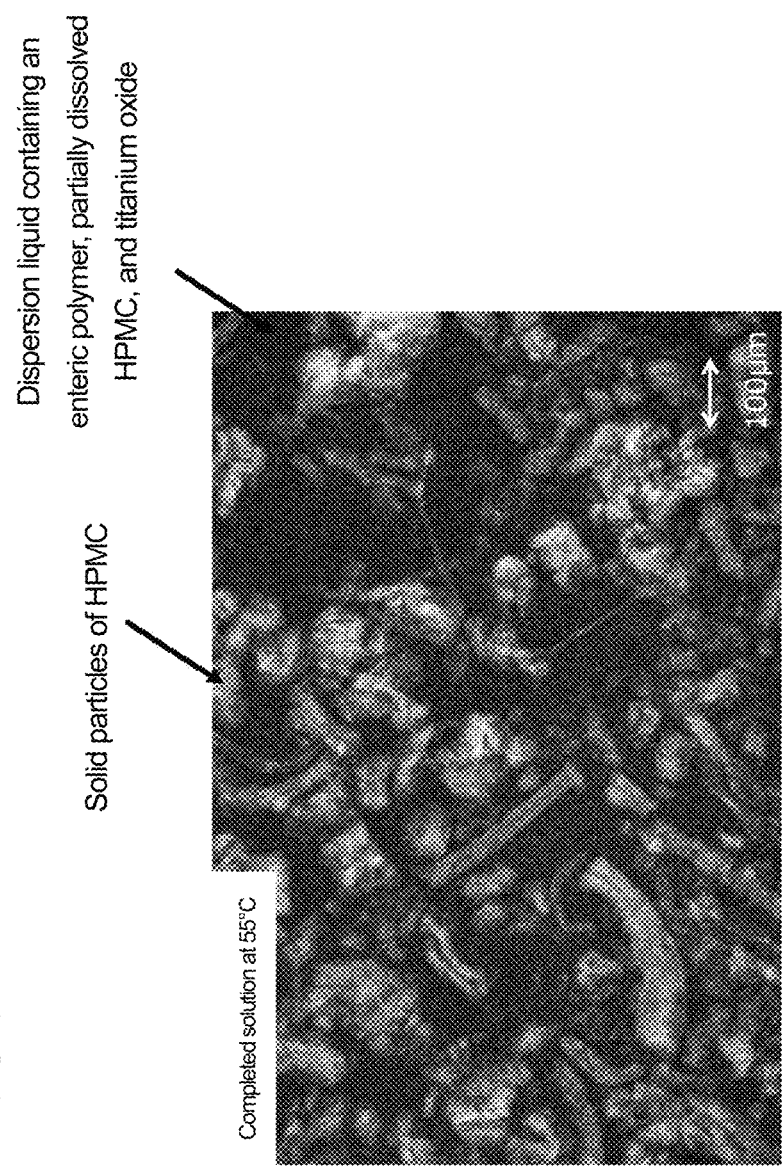

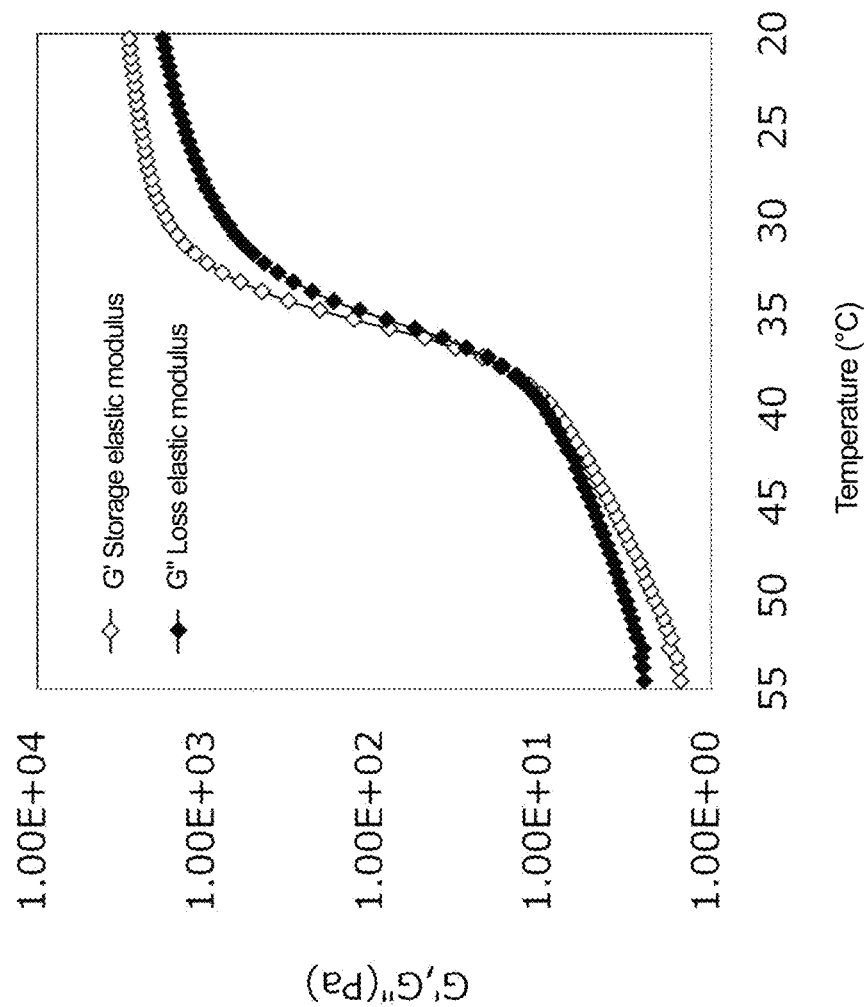
[Fig. 4]

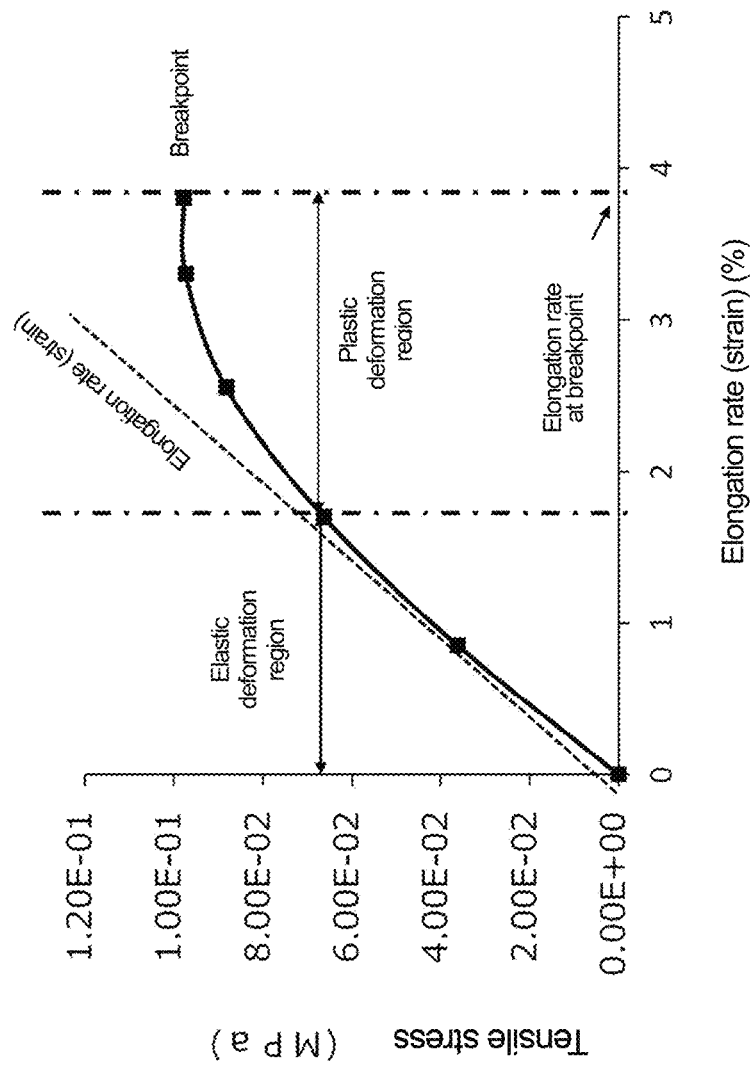
[Fig. 5]

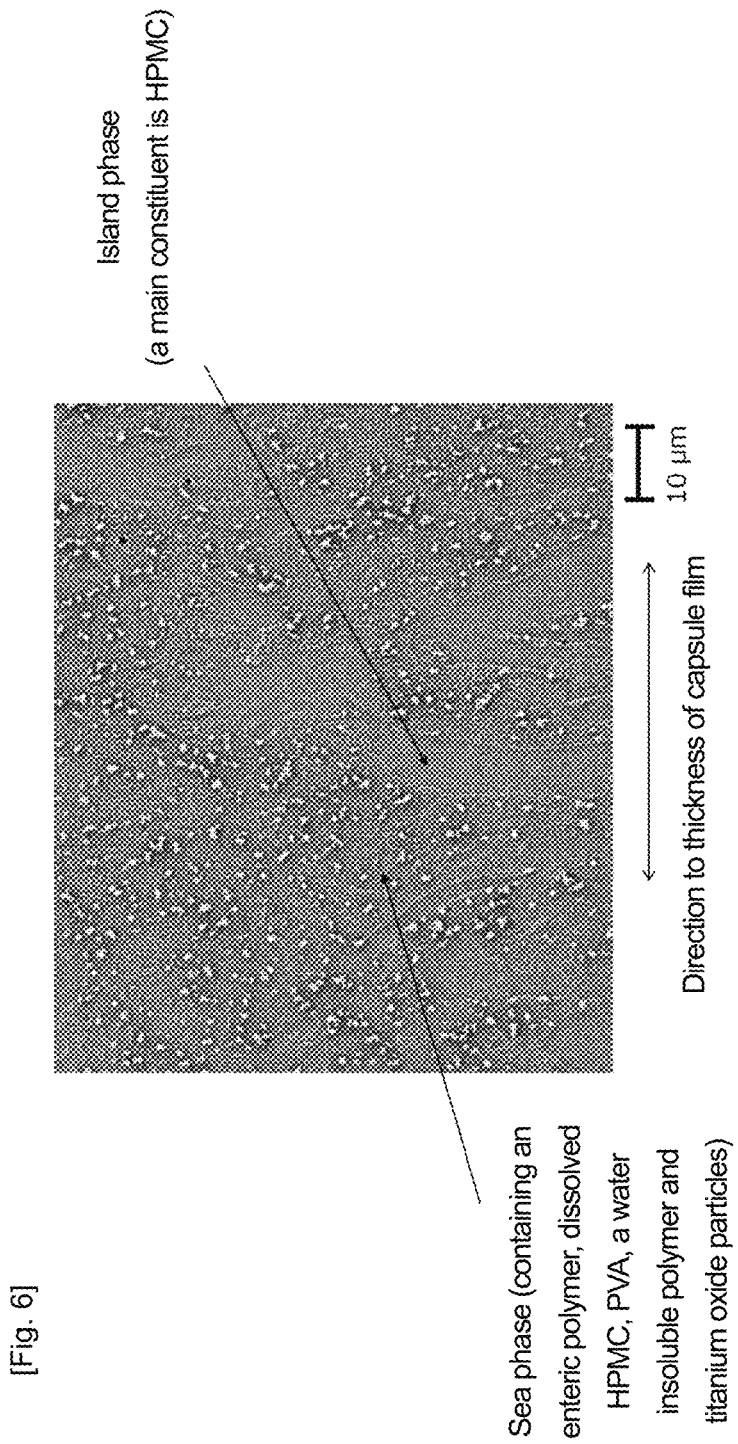
[Fig. 6]

[Fig. 7]
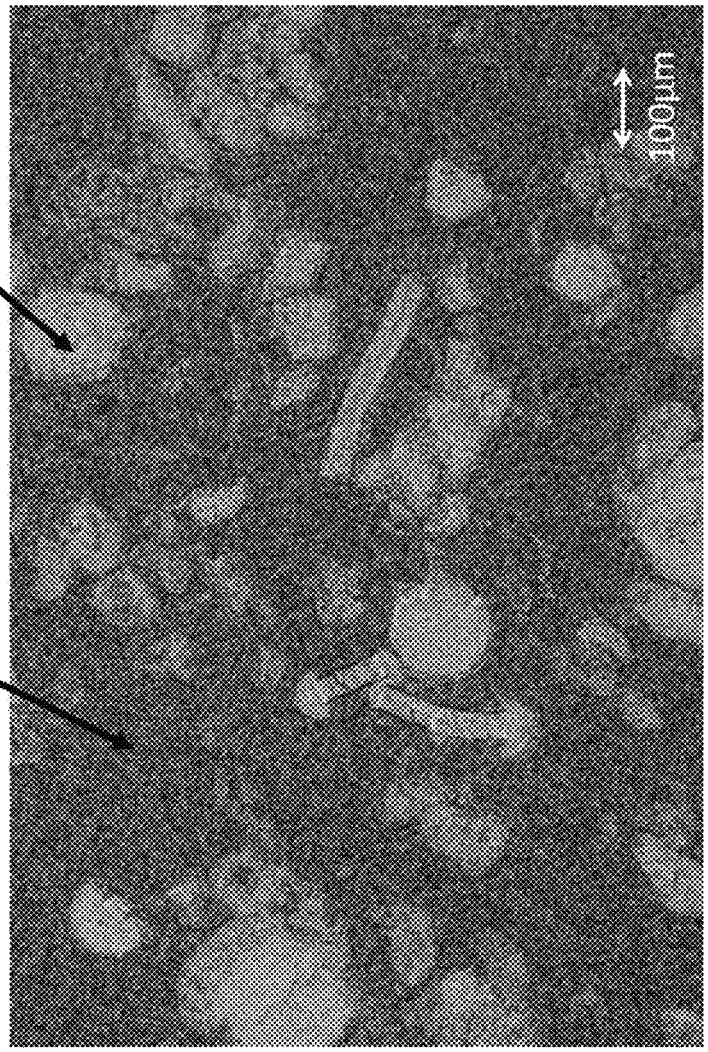

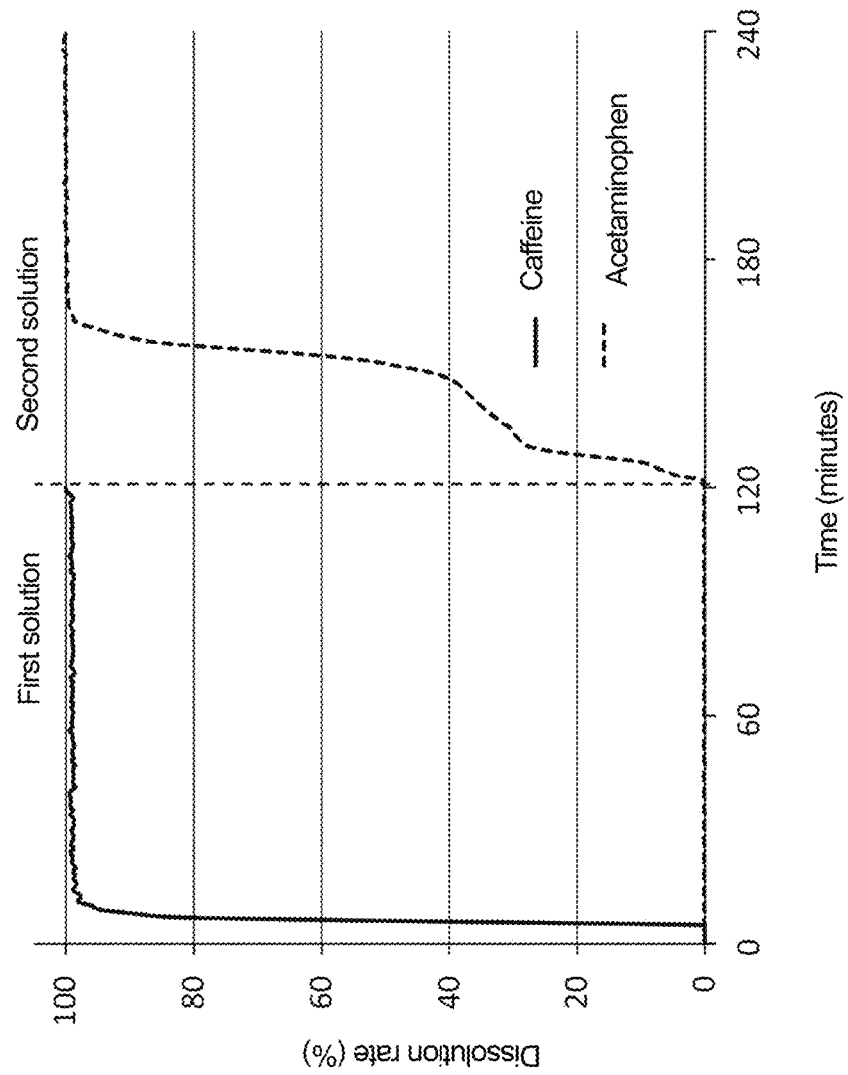
[Fig. 8]

ENTERIC HARD CAPSULE

TECHNICAL FIELD

This description discloses an enteric hard capsule, an enteric hard capsule-preparing solution, a method of preparing an enteric hard capsule-preparing solution, and a method of preparing an enteric hard capsule.

BACKGROUND ART

The term "enteric" is one of dosage forms of a formulation to be orally administered, and in general, means such a formulation characteristic that the formulation is not easily dissolved in the stomach. In addition, the formulation has such a characteristic that the formulation is easily dissolved after being transferred to the intestines. The enteric formulation releases an active pharmaceutical ingredient after being transferred to the intestines without releasing the active pharmaceutical ingredient in the stomach under a strongly acidic environment. Therefore, the enteric formulation is mainly used in order to protect the active pharmaceutical ingredient from gastric acid or gastric enzymes or to cause the active pharmaceutical ingredient to be sustainably released through use of a period of time during which the formulation is transferred from the stomach to the small intestine.

In the pharmaceutical formulation field, the term "enteric" is substantially similarly defined in each Pharmacopeia of Japan (the Japanese Pharmacopoeia, Seventeenth Edition, 6.10 Dissolution Test, "4.3 Delayed-release Dosage Forms" section), the U.S. (US Pharmacopeia Monograph <711> Dissolution 7, "Delayed-Release Dosage Forms" section), and Europe (European Pharmacopeia, 2.9.3, "Delayed-release dosage forms" section). In particular, the term "enteric" is defined in the same manner in Japan, Europe, and the U.S. in that a formulation is required to have acid resistance to such a degree as to be substantially insoluble at 37° C. for 2 hours under an acidic (about pH 1.2, diluted solution of hydrochloric acid) environment. Meanwhile, there is no particular temporal regulation on the dissolution characteristics in the intestines. The dissolution characteristics to be required are varied depending on whether a release target site is the small intestine, the colon, or the large intestine and whether the drug release characteristics are immediate-release characteristics or sustained-release characteristics.

When the formulation dosage form is a tablet, an "enteric" formulation that satisfies the above-mentioned requirement is prepared by coating the tablet with a so-called enteric polymer (Non-patent Literature 1, Chapters 9 and 10).

In addition, when the formulation dosage form is a hard capsule, an enteric hard capsule formulation has hitherto been prepared by a method (coating method) involving coating a hard capsule filled with a content with an enteric polymer similar to that of the tablet. In some cases, a method involving subjecting a non-enteric empty capsule before being released from an immersion pin to enteric coating by an immersion method has hitherto been performed (Patent Literatures 1 to 6, and Non-patent Literatures 2 and 3).

Further, an attempt has also been made to make a hard capsule film enteric. As such related art, there are given, for example, the following:

(1) A gelling agent capable of imparting acid resistance, such as gellan gum, is used instead of or together with an acid-resistant enteric polymer, and thus acid resistance is maintained while a gelation property and film performance are improved (Patent Literatures 7 to 10);

(2) A solvent-based immersion solution is used instead of a water-based solution (Patent Literature 11);

(3) A poorly water-soluble acid-resistant enteric polymer is used as a main component, and a related-art polymer that is water-soluble and has high film-forming ability, such as gelatin or water-soluble cellulose, is partially used (Patent Literatures 12 and 13);

(4) In order to obtain a water-soluble derivative containing a poorly water-soluble enteric polymer, substantially all the acid groups (in particular, a carboxyl group) of the enteric polymer are subjected to salifying. Alternatively, a non-salified polymer is at least partially neutralized with a basic neutralizer and dissolved in water. Alternatively, a non-salified emulsion dispersion liquid is utilized (Patent Literatures 12 to 20); and (5) An alternative technology that does not require solubilization of a polymer, such as injection molding, is used (Patent Literatures 21 to 25, and Non-patent Literature 4).

CITATION LIST

Patent Literature

PTL 1: U.S. Pat. No. 2,196,768 A
PTL 2: U.S. Pat. No. 6,309,666 A
PTL 3: U.S. Pat. No. 7,094,425 B2
PTL 4: U.S. Pat. No. 3,927,195 A
PTL 4: JP 2003-325642
PTL 6: JP 2013-500293 A
PTL 7: JP 2006-16372 A
PTL 8: JP 2010-202550 A
PTL 9: JP 2009-196961 A
PTL 10: WO 2011/036601 A1
PTL 11: U.S. Pat. No. 4,365,060 A
PTL 12: U.S. Pat. No. 3,826,666 A
PTL 13: U.S. Pat. No. 4,138,013 A
PTL 14: U.S. Pat. No. 2,718,667 A
PTL 15: JP 2013-504565 A
PTL 16: JP 2013-540149 A
PTL 17: JP 2015-518005 A
PTL 18: JP 2013-540806 A
PTL 19: JP 2015-515962 A
PTL 20: JP 55-136061 A
PTL 21: JP 47-3547 A
PTL 22: JP 53-52619 A
PTL 23: JP 2006-52819 A
PTL 24: JP 2011-503048 A
PTL 25: JP 2004-522746 A

Non-Patent Literature

NPL 1: Aqueous Polymeric Coating For Pharmaceutical Dosage Forms, 4th edition, CRC Press, 2017, Chapter 4, Chapter 9, Chapter 10 (Table 10.5)
NPL 2: International Journal of Pharmaceutics; 231 (2002), p. 83-95
NPL 3: Drug Dev. Ind. Pharm.; 37(2011) p. 1131-1140
NPL 4: International Journal of Pharmaceutics; 440 (2013), p. 264-272
NPL 5: Reports of the Mie Prefecture Industrial Research Institute, No. 33 (2009), p. 59-64
NPL 6: Drug Targeting Technology, CRC press, 2001, Part I-1(pp. 1-29)

SUMMARY OF INVENTION

Technical Problem

However, in general, preparation of an enteric hard capsule formulation by a coating method requires filling a content into a capsule, fitting a cap and a body to each other, and sealing a fitted portion before coating the surface, and hence a preparation process is complicated. In addition, a burden of operation caused by the complicated preparation process is put on a manufacturer side which fills a content into a capsule, instead of a manufacturer of a hard capsule. The foregoing may impair convenience of a hard capsule as a formation form. When an empty capsule is coated in advance, a drying time is required for each of a capsule film and a coating film, and in order to enhance adhesiveness between the capsule film and the coating film, coating of an underlying portion is further required. As a result, a capsule manufacturing process itself is complicated.

In view of the above-mentioned circumstances, there is a demand that a film of a hard capsule itself be enteric.

A hard capsule is usually prepared by a dipping (immersion) method. Specifically, the immersion method involves dissolving a capsule film polymer material to form an aqueous solution, immersing a molding pin (in general, a molding pin made of stainless steel) in the polymer aqueous solution, pulling up the molding pin from the immersion liquid, inverting the molding pin, and drying the polymer aqueous solution adhering to the surface of the molding pin, to thereby form a film having a thickness of about 100 μm. Then, the dried capsule film is removed from the molding pin and cut to a desired length. After that, a content is filled into the resultant capsule film, and a cap and a body are assembled. Then, printing is performed on the surface of the hard capsule, and the hard capsule is packaged.

In addition, in the immersion method, in order to obtain an aqueous preparing solution for immersion, it is desired that the polymer that is a main component of the hard capsule film be water-soluble, or a most part thereof be an aqueous solution or a part thereof form a dispersion liquid containing significantly fine colloid or solid particles. In addition, it is desired that the polymer have a property of being gelled to be abruptly increased in viscosity along with abrupt increase or decrease in temperature when the molding pin immersed in the preparing solution is pulled up, that is, the polymer have cold gelation ability or hot gelation ability. Further, it is required that the preparing solution for immersion can suppress liquid dripping immediately after the molding pin is pulled up and be finally formed into a film having sufficient hardness and toughness as a hard capsule through dry solidification of a solid content by the subsequent evaporation of moisture.

However, the physical properties of a general enteric polymer (enteric base) for coating are not suitable for preparation of a hard capsule by the immersion method. An enteric polymer that is commercially available for coating of a tablet may function as a film on the surface of a tablet, that is, a solid product, but does not have such film-forming characteristics or strength as to enable the polymer to be independent as a single film body. Therefore, even when a film is formed of the enteric polymer, the film cannot be utilized alone as a hard capsule.

In addition, the related art has the following problems.

In the above-mentioned related art of (1), the moldability of a hard capsule film is improved, but acid resistance is insufficient. Further, when the polymer is gelled through use of the gelling agent, there is a problem in that, in particular, in a cold gelation method that requires a cation as a gelling aid, the stability of a polymer aqueous solution or dispersion liquid and the cold gelation performance of the gelling agent are impaired due to the pH of the aqueous solution containing the polymer or the interaction between the cation and an ionic group of the enteric polymer.

Next, in the above-mentioned related art of (2), it is required to take countermeasures against working environment contamination and fire and explosion caused by an organic solvent and the like that are volatilized during a preparation process, and to collect a waste solvent. Further, there is a problem in that a solvent may remain in a final product.

In the above-mentioned related art of (3), when gelatin is used as a water-soluble polymer or a cold gelling agent, the compatibility between the gelatin and the acid-resistant enteric polymer is insufficient, and turbidness may occur in a capsule film in many cases. Further, gelatin that is an animal protein has a risk of mad cow disease contamination.

Next, in the above-mentioned related art of (4), in order to obtain a preparing solution for immersion, the acid groups of the enteric polymer are salified, or the enteric polymer is substantially completely neutralized (or salified). However, those treatments impart undesirable water sensitivity to a molded hard capsule film itself. Further, there is a problem in that the stability of a polymer aqueous solution or dispersion liquid and the cold gelation performance of the gelling agent are impaired due to the pH of the aqueous solution containing the polymer or the interaction between the cation and an ionic group of the enteric polymer. In addition, an excess amount of a neutralizer (for example, an alkaline agent) is contained. Therefore, when a hard capsule containing the enteric polymer subjected to the above-mentioned treatment as a main component is stored under a high-temperature severe condition, so-called salt precipitation (salting out), in which a component of the neutralizer is gradually released from the capsule, occurs, with the result that there is a risk in that the outer appearance of the capsule may turn yellow.

Even in the case where the enteric polymer is used as a fine dispersion liquid without being completely neutralized and dissolved, in particular, when only an enteric cellulose compound is used as the enteric polymer, it is required to neutralize a majority of carboxyl groups in order to sufficiently reduce each particle diameter of the enteric cellulose compound, and there is a problem in that the amount of a residual salt in the film may reach a concentration as high as from 1 mass % to 10 mass %. Further, when only the enteric cellulose compound is used as the enteric polymer, the hot gelation property thereof is utilized in many cases, and a preparing solution for immersion suitable for molding by the cold gelation method has not been known.

Next, in the above-mentioned related art of (5), a general manufacturing apparatus using the immersion method cannot be used in the first place. Further, in injection molding, a capsule is molded through use of thermoplasticity of the polymer, and hence there is a fear of thermal denaturation of the polymer itself caused by heat treatment at about 100° C. during a molding process. In addition, in injection molding, when a capsule form is molded under heating and then cooled to room temperature, an excessively large stress caused by thermal shrinkage is applied to a film, and there is a fear of the occurrence of cracking in the molded capsule. In addition, a film of a hard capsule that is generally put into circulation currently has a thickness of about 100 μm, and a content is filled into the film by a capsule filling machine. In contrast, in injection molding, it is required to take measures such as preventing cracking by mixing a plasticizer in such an amount that acid resistance may be sacrificed into the film, or keeping the mechanical strength of the film by making the film as thick as about hundreds of µm. Therefore, there is a problem of the interaction between a large amount of the additive and the contained drug. In addition, it is inevitable to set the thickness of a film of a hard capsule molded by injection molding to be larger than that of the hard capsule in circulation. Therefore, it is difficult to prepare an enteric hard capsule that maintains compatibility with the generally used capsule filling machine.

The present invention has an object to provide a hard capsule formed of a hard capsule film that can be molded by the cold gelation method and has enteric characteristics.

Solution to Problem

The inventors of the present invention have made extensive investigations, and as a result, have found that a hard capsule described below has enteric characteristics. The hard capsule includes a film containing a nonionic water-soluble cellulose compound having a viscosity value within a range of from 100 mPa·s to 100,000 mPa·s and an enteric methacrylic acid copolymer, and further containing an enteric cellulose compound, a water-insoluble (meth)acrylic acid alkyl ester copolymer, and at least one component selected from the group consisting of a polyvinyl alcohol copolymer, a plasticizer, and a surfactant. The inventors of the present invention have further found that an enteric hard capsule-preparing solution containing the above-mentioned components can be used for preparing a hard capsule by a cold gelation method.

The present disclosure has been completed based on the above-mentioned findings and includes the following aspects.

Item 1. An enteric hard capsule, comprising a film containing a first component and a second component, and further containing at least one component selected from the group consisting of a third component, a fourth component, and a fifth component, wherein the first component is a nonionic water-soluble cellulose compound having a viscosity value within a range of from 100 mPa·s to 100,000 mPa·s, the second component is an enteric methacrylic acid copolymer, the third component is an enteric cellulose compound, the fourth component is a water-insoluble (meth)acrylic acid alkyl ester copolymer, and the fifth component is at least one kind selected from the group consisting of polyvinyl alcohol, a plasticizer, and a surfactant.

Item 2. The enteric hard capsule according to Item 1, wherein the nonionic water-soluble cellulose compound is at least one kind selected from the group consisting of hydroxypropyl methylcellulose, methylcellulose, and hydroxypropyl cellulose.

Item 3. The enteric hard capsule according to Item 1 or 2, wherein the enteric methacrylic acid copolymer is at least one kind selected from the group consisting of a copolymer of methacrylic acid, methyl methacrylate and methyl acrylate; and a copolymer of methacrylic acid and ethyl acrylate.

Item 4. The enteric hard capsule according to any one of Items 1 to 3, wherein the enteric methacrylic acid copolymer is a copolymer containing 40 mass % to 60 mass % of methacrylic acid and 60 mass % to 40 mass % of ethyl acrylate.

Item 5. The enteric hard capsule according to any one of Items 1 to 4, wherein the enteric cellulose compound is at least one kind selected from the group consisting of hydroxypropyl methylcellulose phthalate, hydroxypropyl methylcellulose acetate succinate, and cellulose acetate phthalate.

Item 6. The enteric hard capsule according to any one of Items 1 to 5, wherein the (meth)acrylic acid alkyl ester copolymer is a copolymer of methyl methacrylate and ethyl acrylate.

Item 7. The enteric hard capsule according to any one of Items 1 to 6, wherein, when a total mass of the first component, the second component, the third component, the fourth component, and the fifth component contained in the film is set to 100 mass %, and when a ratio of the first component is represented by $\alpha$ mass %, a ratio of the second component is represented by $\beta$ mass %, a ratio of the third component is represented by $\gamma$ mass %, a ratio of the fourth component is represented by $\sigma$ %, and a ratio of the fifth component is represented by $\varphi$, $0.5 \le (\beta+\gamma+\sigma)/(\alpha+\beta+\gamma+\sigma+\varphi) \le 0.9$ is established, and $0.4 \le (\beta+\gamma)/(\beta+\gamma+\sigma)$ is established.

Item 8. The enteric hard capsule according to any one of Items 1 to 7, wherein, when a total mass of the first component, the second component, the third component, the fourth component, and the fifth component contained in the film is set to 100 mass %, and when a ratio of the first component is represented by $\alpha$ mass %, a ratio of the second component is represented by $\beta$ mass %, a ratio of the third component is represented by $\gamma$ mass %, a ratio of the fourth component is represented by $\sigma$ %, and a ratio of the fifth component is represented by $\varphi$, $0.05 \le \alpha/(\alpha+\beta+\gamma+\sigma+\varphi) \le 0.5$ is established.

Item 9. The enteric hard capsule according to any one of Items 1 to 8, wherein, when a total mass of the first component, the second component, the third component, the fourth component, and the fifth component contained in the film is set to 100 mass %, and when a ratio of the second component is represented by $\beta$ mass % and a ratio of the third component is represented by $\gamma$ mass %, $0.1 \le \beta/(\beta+\gamma) \le 1$ is established.

Item 10. The enteric hard capsule according to Item 9, wherein, when the total mass of the first component, the second component, the third component, the fourth component, and the fifth component contained in the film is set to 100 mass %, and when the ratio of the first component is represented by $\alpha$ mass %, the ratio of the second component is represented by $\beta$ mass %, the ratio of the fourth component is represented by $\sigma$ %, and the ratio of the fifth component is represented by $\varphi$, $\gamma=0$ is established, and $0.3 \le \beta/(\alpha+\beta+\gamma+\sigma+\varphi) \le 0.7$ is established.

Item 11. The enteric hard capsule according to any one of Items 1 to 10, wherein at least a part of the second component is contained as a salt thereof, which is pharmaceutically acceptable or is acceptable as a food additive, and/or at least a part of the third component is contained as a salt thereof, which is pharmaceutically acceptable or is acceptable as a food additive.

Item 12. The enteric hard capsule according to Item 11, wherein, when a total molar number of carboxyl groups forming the salts in the second component and the third component contained in the film and carboxyl groups prevented from forming the salts is set to 100 mol %, a content of the carboxyl groups forming the salts is from 2 mol % to 50 mol %.

Item 13. The enteric hard capsule according to any one of Items 1 to 12, wherein the film has a thickness of from 50 µm to 250 µm.

Item 14. The enteric hard capsule according to Item 13, wherein the film has an elastic modulus of from 1 GPa to 5 GPa at 25° C. and a relative humidity of 60%.

Item 15. The enteric hard capsule according to Item 13 or 14, wherein the film has an elongation at break of from 2% to 30% at 25° C. and a relative humidity of 22%.

Item 16. The enteric hard capsule according to any one of Items 1 to 15, wherein the film of the enteric hard capsule has a sea-island structure in which an island phase is substantially formed of the first component.

Item 17. The enteric hard capsule according to Item 16, wherein the island phase has a short diameter of 0.1 μm or more and less than 30 μm.

Item 18. The enteric hard capsule according to any one of Items 1 to 17, wherein, in a dissolution test using a solution having a pH of 1.2, a dissolution ratio of the enteric hard capsule after two hours is 25% or less.

Item 19. The enteric hard capsule according to Item 18, wherein the dissolution ratio of the enteric hard capsule in the dissolution test is 10% or less.

Item 20. An enteric hard capsule-preparing solution, comprising a component (i), a component (ii), a basic neutralizer that is pharmaceutically acceptable or is acceptable as a food additive, and a solvent, and further comprising at least one component selected from the group consisting of a component (iii), a component (iv), and a component (v), wherein the component (i) is a nonionic water-soluble cellulose compound having a viscosity value within a range of from 100 mPa·s to 100,000 mPa·s, the component (ii) is an enteric methacrylic acid copolymer, the component (iii) is an enteric cellulose compound, the component (iv) is a water-insoluble (meth)acrylic acid alkyl ester copolymer, and the component (v) is at least one kind selected from the group consisting of polyvinyl alcohol, a plasticizer, and a surfactant.

Item 21. The enteric hard capsule-preparing solution according to Item 20, wherein the component (i) is dispersed as a solid particle.

Item 22. The enteric hard capsule-preparing solution according to Item 20 or 21, wherein a part of the component (ii) and/or a part of the component (iii) is partially neutralized with the basic neutralizer.

Item 23. The enteric hard capsule-preparing solution according to Item 22, wherein a degree of neutralization in the partial neutralization is from 2% to 50% with respect to a molar number required for complete neutralization of the components (ii) and (iii).

Item 24. The enteric hard capsule-preparing solution according to any one of Items 20 to 23, wherein the component (ii) is dispersed as a colloid particle.

Item 25. The enteric hard capsule-preparing solution according to any one of Items 20 to 24, wherein the nonionic water-soluble cellulose compound is at least one kind selected from the group consisting of hydroxypropyl methylcellulose, methylcellulose, and hydroxypropyl cellulose.

Item 26. The enteric hard capsule-preparing solution according to any one of Items 20 to 25, wherein the enteric cellulose compound is at least one kind selected from the group consisting of hydroxypropyl methylcellulose phthalate, hydroxypropyl methylcellulose acetate succinate, and cellulose acetate phthalate.

Item 27. The enteric hard capsule-preparing solution according to any one of Items 20 to 26, wherein the enteric methacrylic acid copolymer is at least one kind selected from the group consisting of a copolymer of methacrylic acid, methyl methacrylate and methyl acrylate; and a copolymer of methacrylic acid and ethyl acrylate.

Item 28. The enteric hard capsule-preparing solution according to any one of Items 20 to 27, wherein a part or an entirety of the enteric cellulose compound is substituted with the water-insoluble (meth)acrylic acid alkyl ester copolymer that is the component (iv).

Item 29. The enteric hard capsule-preparing solution according to any one of Items 20 to 28, wherein the water-insoluble (meth)acrylic acid alkyl ester copolymer is a copolymer of methyl methacrylate and ethyl acrylate.

Item 30. The enteric hard capsule-preparing solution according to Item 28 or 29, wherein the component (iv) is dispersed as a colloid particle.

Item 31. The enteric hard capsule-preparing solution according to any one of Items 20 to 30, wherein, when a total mass of the component (i), the component (ii), the component (iii), the component (iv), and the component (v) contained in the enteric hard capsule-preparing solution is set to 100 mass %, and when a ratio of the component (i) is represented by α' mass %, a ratio of the component (ii) is represented by β' mass %, a ratio of the component (iii) is represented by γ' mass %, a ratio of the component (iv) is represented by σ' mass %, and a ratio of the component (v) is represented by φ' mass %, $0.5 \leq (\beta'+\gamma'+\sigma')/(\alpha'+\beta'+\gamma'+\sigma'+\varphi') \leq 0.9$ is established, and $0.4 \leq (\beta'+\gamma')/(\beta'+\gamma'+\sigma')$ is established.

Item 32. The enteric hard capsule-preparing solution according to any one of Items 20 to 31, wherein, when a total mass of the component (i), the component (ii), the component (iii), the component (iv), and the component (v) contained in the enteric hard capsule-preparing solution is set to 100 mass %, and when a ratio of the component (i) is represented by α' mass %, a ratio of the component (ii) is represented by β' mass %, a ratio of the component (iii) is represented by γ' mass %, a ratio of the component (iv) is represented by σ' mass %, and a ratio of the component (v) is represented by φ' mass %, $0.05 \leq \alpha'/((\alpha'+\beta'+\gamma'+\sigma'+\varphi') \leq 0.5$ is established.

Item 33. The enteric hard capsule-preparing solution according to any one of Items 20 to 32, wherein, when a total mass of the component (i), the component (ii), the component (iii), the component (iv), and the component (v) contained in the enteric hard capsule-preparing solution is set to 100 mass %, and when a ratio of the component (ii) is represented by β' mass % and a ratio of the component (iii) is represented by γ' mass %, $0.1 \leq \beta'/(\beta'+\gamma') \leq 1$ is established.

Item 34. The enteric hard capsule-preparing solution according to Item 33, wherein, when the total mass of the component (i), the component (ii), the component (iii), the component (iv), and the component (v) contained in the enteric hard capsule-preparing solution is set to 100 mass %, and when the ratio of the component (i) is represented by α' mass %, the ratio of the component (ii) is represented by β' mass %, the ratio of the component (iv) is represented by σ' mass %, and the ratio of the component (v) is represented by φ' mass %, γ'=0 is established, and $0.3 \leq \beta'/(\alpha'+\beta'+\gamma'+\sigma'+\varphi') \leq 0.7$ is established.

Item 35. The enteric hard capsule-preparing solution according to Item 34, wherein a degree of neutralization of the component (ii) with the basic neutralizer is from 2% to 20%.

Item 36. The enteric hard capsule-preparing solution according to any one of Items 20 to 35, wherein the basic neutralizer is at least one kind selected from the group consisting of sodium hydroxide, potassium hydroxide, and calcium hydroxide.

Item 37. The enteric hard capsule-preparing solution according to any one of Items 20 to 35, wherein the basic neutralizer is at least one kind selected from the group consisting of ammonia and ammonium carbonate.

Item 38. The enteric hard capsule-preparing solution according to any one of Items 31 to 37, wherein, when the enteric hard capsule-preparing solution is set to 100 mass %, a total amount of the component (i), the component (ii), the component (iii), the component (iv), and the component (v) is from 10 mass % to 30 mass %.

Item 39. The enteric hard capsule-preparing solution according to any one of Items 20 to 38, wherein the enteric hard capsule-preparing solution has a viscosity of from 100 mPa·s to 10,000 mPa·s.

Item 40. A method of preparing an enteric hard capsule-preparing solution, comprising mixing a component (i) and a component (ii) with each other under a condition in which a basic neutralizer that is pharmaceutically acceptable or is acceptable as a food additive is present in a solvent, wherein the component (i) is a nonionic water-soluble cellulose compound having a viscosity value within a range of from 100 mPa·s to 100,000 mPa·s, and the component (ii) is an enteric methacrylic acid copolymer.

Item 41. The method of preparing an enteric hard capsule-preparing solution according to Item 40, wherein the nonionic water-soluble cellulose compound is at least one kind selected from the group consisting of hydroxypropyl methylcellulose, methylcellulose, and hydroxypropyl cellulose.

Item 42. The method of preparing an enteric hard capsule-preparing solution according to Item 40 or 41, wherein the enteric methacrylic acid copolymer is at least one kind selected from the group consisting of a copolymer of methacrylic acid, methyl methacrylate and methyl acrylate; and a copolymer of methacrylic acid and ethyl acrylate.

Item 43. The method of preparing an enteric hard capsule-preparing solution according to any one of Items 40 to 42, wherein the basic neutralizer is at least one kind selected from the group consisting of sodium hydroxide, potassium hydroxide, and calcium hydroxide.

Item 44. The method of preparing an enteric hard capsule-preparing solution according to any one of Items 40 to 42, wherein the basic neutralizer is at least one kind selected from the group consisting of ammonia and ammonium carbonate.

Item 45. The method of preparing an enteric hard capsule-preparing solution according to any one of Items 40 to 44, further comprising in random order: a step A of preparing a neutralized solution of a component (iii); a step B of adding the component (i) to the neutralized solution containing the component (iii), to thereby prepare a partially dissolved solution of the component (i); and a step C of mixing a dispersion liquid of the component (ii) and the neutralized solution or the partially dissolved solution with each other, wherein the component (iii) is an enteric cellulose compound.

Item 46. The method of preparing an enteric hard capsule-preparing solution according to Item 45, wherein the enteric cellulose compound is at least one kind selected from the group consisting of hydroxypropyl methylcellulose phthalate, hydroxypropyl methylcellulose acetate succinate, and cellulose acetate phthalate.

Item 47. The method of preparing an enteric hard capsule-preparing solution according to Item 45 or 46, wherein the step A is a step of preparing a neutralized solution by at least partially neutralizing the component (iii) with a basic neutralizer that is pharmaceutically acceptable or is acceptable as a food additive and dissolving the component (iii) in a solvent, and a degree of neutralization of the component (iii) is 50% or more, or the component (iii) is completely neutralized.

Item 48. The method of preparing an enteric hard capsule-preparing solution according to any one of Items 45 to 47, wherein the step B is a step of preparing a partially dissolved solution by partially dissolving the component (i) in the neutralized solution containing the component (iii) or in a mixed solution of the neutralized solution of the component (iii) and the dispersion liquid of the component (ii), and the step of preparing the partially dissolved solution is a step of preparing a dispersion liquid by adding the component (i) to the neutralized solution containing the component (iii) or the mixed solution of the neutralized solution of the iii-component and the dispersion liquid of the component (ii) at a first temperature T1 equal to or higher than a cloud point T0 of the component (i) and partially dissolving the component (i) at a second temperature T2 lower than the cloud point.

Item 49. The method of preparing an enteric hard capsule-preparing solution according to any one of Items 45 to 48, further comprising a step D of mixing the solution prepared in the step A, B, or C and a water-insoluble (meth)acrylic acid ester copolymer that is a component (iv) with each other.

Item 50. The method of preparing an enteric hard capsule-preparing solution according to Item 49, wherein the water-insoluble (meth)acrylic acid alkyl ester copolymer is a copolymer of methyl methacrylate and ethyl acrylate.

Item 51. The method of preparing an enteric hard capsule-preparing solution according to any one of Items 45 to 50, further comprising a step E of holding the solution obtained in the step B, C, or D at a third temperature T3 lower than a cloud point of the component (i).

Item 52. The method of preparing an enteric hard capsule-preparing solution according to Item 40, further comprising in random order: a step A' of preparing a partially neutralized solution of the component (ii); a step B' of preparing a partially dissolved solution of the component (i); and a step C' of mixing a dispersion liquid of a component (iv) and the solution prepared in the step A or B with each other, wherein the component (iv) is a water-insoluble (meth)acrylic acid alkyl ester copolymer.

Item 53. The method of preparing an enteric hard capsule-preparing solution according to Item 52, wherein the water-insoluble (meth)acrylic acid alkyl ester copolymer is a copolymer of methyl methacrylate and ethyl acrylate.

Item 54. The method of preparing an enteric hard capsule-preparing solution according to Item 52 or 53, the step A' is a step of preparing a neutralized solution by at least partially neutralizing the component (ii) with a basic neutralizer that is pharmaceutically acceptable or is acceptable as a food additive and dissolving the component (ii) in a solvent, and a degree of neutralization of the component (ii) is from 2% to 20%.

Item 55. The method of preparing an enteric hard capsule-preparing solution according to any one of Items 52 to 54, wherein the step B' is a step of preparing a partially dissolved solution by partially dissolving the component (i) in the neutralized solution containing the component (ii), and wherein the step of preparing the partially dissolved solution is a step of preparing a dispersion liquid by adding the component (i) to the neutralized solution containing the component (ii) or a mixed solution of the neutralized solution of the component (ii) and the dispersion liquid of the component (iv) at a first temperature T1 equal to or higher than a cloud point T0 of the component (i) and partially dissolving the component (i) at a second temperature T2 lower than the cloud point.

Item 56. The method of preparing an enteric hard capsule-preparing solution according to Item 55, further comprising a step E' of holding the solution obtained in the step B' or C' at a third temperature T3 lower than the cloud point of the component (i).

Item 57. The method of preparing an enteric hard capsule-preparing solution according to Item 51 or 56, wherein a range T3 of the third temperature is from 40° C. to 60° C.

Item 58. The method of preparing an enteric hard capsule-preparing solution according to any one of Items 48 to 51 and 55 to 57, wherein the first temperature T1 falls within a range of from 60° C. to 90° C.

Item 59. The method of preparing an enteric hard capsule-preparing solution according to any one of Items 48 to 51 and 55 to 57, wherein the second temperature T2 falls within a range of from 30° C. to 60° C.

Item 60. The method of preparing an enteric hard capsule-preparing solution according to any one of Items 40 to 59, wherein the enteric hard capsule-preparing solution has a viscosity of from 100 mPa·s to 10,000 mPa·s.

Item 61. A method of preparing an enteric hard capsule, comprising the following steps: a first step of immersing a mold pin in the enteric hard capsule-preparing solution of any one of Items 20 to 39 or an enteric hard capsule-preparing solution obtained by the preparation method of any one of Items 40 to 60, the mold pin having a surface temperature lower than a temperature of the enteric hard capsule-preparing solution; and a second step of pulling up the mold pin from the enteric hard capsule-preparing solution and drying the enteric hard capsule-preparing solution adhering to the mold pin.

Item 62. The method of preparing an enteric hard capsule according to Item 61, wherein the enteric hard capsule-preparing solution has a temperature of from 40° C. to 60° C.

Item 63. The method of preparing an enteric hard capsule according to Item 62 or 61 or 62, wherein the surface temperature of the mold pin before being immersed in the preparing solution is from 5° C. to 40° C.

Item 64. The method of preparing an enteric hard capsule according to any one of Items 61 to 63, wherein the drying of the enteric hard capsule-preparing solution adhering to the mold pin is performed at a temperature of less than 40° C.

Item 65. An enteric hard capsule formulation, comprising the enteric hard capsule of any one of Items 1 to 19 sealed with a seal liquid, the seal liquid being made of a diluted aqueous solution in which at least one kind of enteric polymer selected from the group consisting of an enteric methacrylic acid copolymer and an enteric cellulose compound is at least partially neutralized, or a liquid in which the enteric polymer is dissolved in a water/ethanol or water/isopropanol solvent.

Item 66. A hard capsule formulation, comprising the enteric hard capsule of any one of Items 1 to 19 in a hard capsule that is dissolvable under an acidic condition.

Advantageous Effects of Invention

The present invention can provide the hard capsule formed of the hard capsule film having enteric characteristics, which can be molded by the cold gelation method. In addition, according to the present invention, the enteric capsule can be prepared without using the gelling agent. Further, a content can be filled into the hard capsule through use of a capsule filling machine that has hitherto been used.

BRIEF DESCRIPTION OF DRAWINGS

FIG. 1 is a diagram showing a schematic diagram of dynamic viscoelastic behavior in the process of lowering the temperature of an enteric hard capsule preparation liquid. T0 indicates a cloud point or a dissolution starting temperature. T1, T2, and T3 indicate the first temperature, the second temperature, and the third temperature described in the specification, respectively. T4 indicates an abrupt viscosity increase starting temperature. T5 indicates room temperature (20° C. to 25° C.).

FIG. 2 shows a scanning electron microscope image of a cross section of the capsule film prepared as Example 2-2.

FIG. 3 shows an optical microscope image of a capsule preparation liquid (55° C.) prepared as Example 2-2.

FIG. 4 shows the dynamic viscoelastic behavior of a capsule preparation liquid prepared as Example 2-2 at the time of temperature decrease. For example, 1.00E + 2 on the vertical axis indicates 100, and 1.00E + 3 indicates 1000.

FIG. 5 shows an example of a typical tensile stress-elongation (strain, %) curve in a tensile test, and an explanation of an elastic modulus (Young's modulus) and an elongation at break. The elastic modulus on the vertical axis indicates a slope in a low stress elastic region. For example, 1.00E-02 on the vertical axis indicates 0.01 and 1.00E-1 indicates 0.1. Further, the elongation at break on the horizontal axis is the elongation (strain, %), when the test piece breaks.

FIG. 6 shows a scanning electron microscope image of a cross section of the capsule film prepared as Example 6-2.

FIG. 7 shows an optical microscope image of a capsule preparation liquid (55° C.) prepared as Example 6-2.

FIG. 8 shows dissolution characteristics of a double-capsule containing an enteric hard capsule of the present disclosure as an inner capsule.

DESCRIPTION OF EMBODIMENTS

1. Description of Terms and Materials

First, terms and materials to be used in this description, claims, and the like are described. The terms and materials regarding the present disclosure comply with the description in this section unless otherwise stated.

In the present disclosure, the term "hard capsule" refers to an empty capsule in which a content is filled into a produced capsule film. Usually, the hard capsule includes a cap portion and a body portion, and is also called a hard capsule or a two-piece capsule. The "hard capsule" in the present disclosure can have imparted thereto a shape that is the same as or similar to that of a related-art hard capsule that is commercially available, which is intended to be orally administered to a target such as a human or an animal.

The "hard capsule" according to the present disclosure does not encompass a soft capsule manufactured by filling a content between two films and causing the films to adhere to each other, a seamless capsule manufactured by dropping a content together with a film solution onto a solidification liquid, or a microcapsule prepared by incorporating an active ingredient inside through base precipitation or emulsification.

In addition, in the present disclosure, an empty hard capsule is simply referred to as "hard capsule" or "capsule", and a hard capsule filled with a content is referred to as "hard capsule formulation".

In the present disclosure, the term "enteric hard capsule" refers to a hard capsule in which a film of a capsule main body itself has "enteric" characteristics that comply with the following conditions.

Specifically, the term "enteric" refers to the characteristics that satisfy at least the following condition (i).

(i) In the dissolution test described in the Japanese Pharmacopoeia, Revised Seventeenth Edition (hereinafter sometimes simply referred to as "Japanese Pharmacopoeia, Seventeenth Edition"), a dissolution rate of a content when a test object is immersed in a first liquid at 37° C.±0.5° C. for 2 hours is 25% or less, preferably 10% or less. The pH of the first liquid is preferably about 1.2. The first liquid may be prepared, for example, by adding 7.0 ml of hydrochloric acid and water to 2.0 g of sodium chloride to obtain 1,000 ml of a liquid.

The term "enteric" preferably satisfies the following condition (ii) as well as the above-mentioned condition (i). (ii) In the above-mentioned dissolution test, the content is eluted when the test object is immersed in a second liquid at 37° C.±0.5° C. The pH of the second liquid is preferably about 6.8. The second liquid may be prepared, for example, by dissolving 3.40 g of potassium dihydrogen phosphate and 3.55 g of anhydrous disodium hydrogen phosphate in water to obtain 1,000 mL of a phosphate buffer and adding 1 volume of water to 1 volume of the phosphate buffer. In this case, there is no limitation on a period of time during which the dissolution rate of the content in the second liquid is measured. For example, when it is required that the content be eluted relatively rapidly after reaching the intestines, the dissolution rate after 30 minutes from the immersion of the test object in the second liquid is 50%, preferably 70% or more, more preferably 80% or more. In addition, for example, the dissolution rate after 45 minutes from the immersion of the test object in the second liquid is 75% or more, preferably 80% or more, more preferably 90% or more. Further, for example, the dissolution rate after 1 hour from the immersion of the test object in the second liquid is 75% or more, preferably 80% or more, more preferably 90% or more.

The dissolution test may be carried out in accordance with the dissolution test method specified in the Japanese Pharmacopoeia, Seventeenth Edition (the Japanese Pharmacopoeia, Seventeenth Edition, 6.10-1.2 Paddle Method (paddle revolution number: 50 revolutions/min), with a sinker corresponding to FIG. 6.10-2a being used).

There is no limitation on a content to be used in the dissolution test as long as the content itself is rapidly dissolved in a test solution and can be quantified by a known method. There is given, for example, acetaminophen.

The term "nonionic water-soluble cellulose compound" (hereinafter sometimes simply referred to as "water-soluble cellulose compound") refers to a water-soluble cellulose ether, which is a cellulose compound (polymer) that does not have an ionic group in a molecule and becomes water-soluble by having nonionic hydrophilic groups such as —OH and =O, and in which a part of hydroxyl groups of a glucose ring of cellulose is etherified.

A specific example thereof may be a water-soluble cellulose ether having a hydrogen atom of a hydroxy group of cellulose substituted with at least one group of an alkyl group or a hydroxyalkyl group. Herein, examples of the "alkyl group" in the alkyl group or the hydroxyalkyl group may include linear or branched lower alkyl groups each having 1 to 6 carbon atoms, preferably 1 to 4 carbon atoms. Specific examples thereof may include a methyl group, an ethyl group, a butyl group, and a propyl group. Specific examples of the nonionic water-soluble cellulose compound include: lower alkyl celluloses, such as methylcellulose (MC); hydroxy lower alkyl celluloses, such as hydroxyethyl cellulose (HEC) and hydroxypropyl cellulose (HPC); and hydroxy lower alkyl alkyl celluloses, such as hydroxyethyl methylcellulose, hydroxyethyl ethylcellulose, and hydroxypropyl methylcellulose (sometimes referred to as hypromellose or HPMC in this description). Of those, methylcellulose, hydroxypropyl cellulose, and hydroxypropyl cellulose are commercially available and particularly suitable for pharmaceutical and food applications. The degree of substitution of the water-soluble cellulose ether is not particularly limited, and for example, hydroxypropyl methylcellulose, methylcellulose, and hydroxypropyl cellulose specified in the Japanese Pharmacopoeia are used. For example, the degree of substitution with a methoxy group of hydroxypropyl methylcellulose is preferably from 16.5 mass % to 30.0 mass %, more preferably from 19.0 mass % to 30.0 mass %, particularly preferably from 28.0 mass % to 30.0 mass %, and the degree of substitution with a hydroxypropoxy group thereof is preferably from 4.0 mass % to 32.0 mass %, more preferably from 4.0 mass % to 12.0 mass %, particularly preferably from 7.0 mass % to 12.0 mass %. In addition, the degree of substitution with a methoxy group of methylcellulose is preferably from 26.0 mass % to 33.0 mass %, more preferably from 28.0 mass % to 31.0 mass %. Those degrees of substitution may be measured by a method compliant with a method of measuring a degree of substitution of hydroxypropyl methylcellulose, methylcellulose, and hydroxypropyl cellulose described in the Japanese Pharmacopoeia, Seventeenth Edition.

Of those, hydroxypropyl methylcellulose represented by the following formula is an optimum cellulose compound in that hydroxypropyl methylcellulose is excellent in film-forming property and mechanical strength under low moisture.

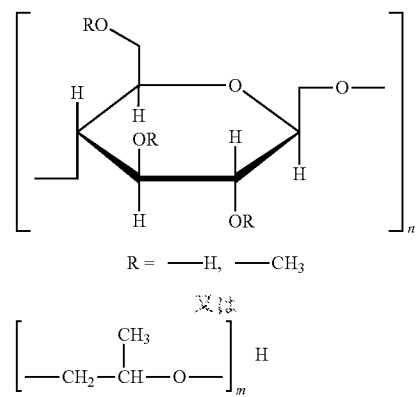

(where "n" and "m" represent any integers.)

The hydroxypropyl methylcellulose to be used in the present disclosure encompasses hypromellose of substitution types (substitution grades) 2910, 2906, and 2208 specified in the Japanese Pharmacopoeia, Seventeenth Edition.

TABLE 1

| Substitution type | Methoxy group (%) | | Hydroxypropoxy group (%) | |
|---|---|---|---|---|
| | Lower limit | Upper limit | Lower limit | Upper limit |
| 1828 | 16.5 | 20.0 | 23.0 | 32.0 |
| 2208 | 19.0 | 24.0 | 4.0 | 12.0 |
| 2906 | 27.0 | 30.0 | 4.0 | 7.5 |
| 2910 | 28.0 | 30.0 | 7.0 | 12.0 |

In addition, the hydroxypropyl methylcellulose according to the present disclosure encompasses hypromellose having the following molecular weight that is approved for use as a food additive in Japan.

<Molecular Weight>

Unsubstituted structural unit: 162.14

Substituted structural unit: about 180 (degree of substitution: 1.19), about 210 (degree of substitution: 2.37)

Polymer: about 13,000 (n=about 70) to about 200,000 (n=about 1,000).

As methylcellulose and hydroxypropyl methylcellulose that are commercially available, there may be given, for example, Japanese Pharmacopoeia METOLOSE (trademark) series and METOLOSE series for food additives manufactured by Shin-Etsu Chemical Co., Ltd., AnyCoat-C or AnyAddy (trademark) series manufactured by LOTTE (former Samsung) Fine Chemical Co., Ltd., METHOCEL (trademark) series manufactured by The Dow Chemical Company, and Benecel (trademark) series manufactured by Ashland Inc.

The hydroxypropyl cellulose targeted at in the present disclosure also encompasses HPC having a molecular weight of about 30,000 (n=about 100) to about 1,000,000 (n=about 2,500) approved for use as a food additive and a pharmaceutical additive in Japan (16th JECFA. Hydroxypropyl Cellulose (Revised Specification). FNP52 Add 12, 2004). As hydroxypropyl cellulose having a high "viscosity value" that is commercially available, there may be given Klucel (trademark) series manufactured by Ashland Inc. and NISSO HPC manufactured by Nippon Soda Co., Ltd. For example, in Klucel (trademark) series manufactured by Ashland Inc., HPC corresponds to those which have labeled viscosity types G, M, and H.

Those nonionic water-soluble cellulose compounds are usually supplied as solid particles that are finely pulverized within a range of the order of from about 0.1 µm to about 100 µm. In addition, it is preferred that those nonionic water-soluble cellulose compounds be "non-salified". The term "non-salifying" means that, except for a trace amount of a chloride that is inevitably mixed or present as a residual impurity in a manufacturing process of a cellulose compound, a large part of free acid residues of the cellulose compound is not salified.

In the present disclosure, it is preferred to use a nonionic water-soluble cellulose compound in which the "viscosity value" of a 2 mass % aqueous solution at 20° C. is 100 mPa·s or more. In the following, a value of the viscosity is sometimes simply referred to as "viscosity value". Regarding a method of measuring the "viscosity value", measurement is performed in accordance with the sections of methylcellulose and hypromellose formulated based on International Harmonization after the Japanese Pharmacopoeia, Fifteenth Edition. Specifically, the term "viscosity value" refers to a value (mPa·s) of a viscosity at 20° C.±0.1° C. of a 2 mass % aqueous solution of water-soluble cellulose. In the measurement of the "viscosity value", in the case of the "viscosity value" of less than 600 mPa·s, a first method (Ubbelohde method) in General Tests, 2.53 Viscosity Determination is used, and in the case of the "viscosity value" of 600 mPa·s or more, a second method, 2.1.2. Single cylinder-type rotational viscometer (Brookfield type viscometer) in General Tests, 2.53 Viscosity Determination is used.

In addition, as the "viscosity value", a labeled viscosity of a chemical manufacturer (sometimes referred to as "viscosity grade value") may also be adopted. Regarding the labeled viscosity and the width of the labeled viscosity, for example, in methylcellulose and hydroxypropyl methylcellulose sold under the trademark METOLOSE series manufactured by Shin-Etsu Chemical Co., Ltd., 80% to 120% of the labeled viscosity is defined in the case of the labeled viscosity of less than 600 mPa·s, and 75% to 140% of the labeled viscosity is defined in the case of the labeled viscosity of 600 mPa·s or more. Regarding the lower limit value of 100 mPa·s in the present disclosure, the labeled viscosity may be used directly as the "viscosity value" as long as the spirit of the present disclosure is not impaired.

In addition, in methylcellulose and hydroxypropyl methylcellulose sold under the trademark METHOCEL series manufactured by The Dow Chemical Company, the viscosity value of an aqueous solution at 20° C. and a concentration of 2 mass % is measured through use of the Ubbelohde method in ASTM, D1347, or D2363, and the relationship between the labeled viscosity (viscosity grade) and the number average molecular weight and weight average molecular weight is substantially compatible with that of the above-mentioned official values. Any labeled viscosity may be used directly as the "viscosity value" as long as the spirit of the present disclosure is not impaired.

In the present disclosure, the lower limit value of the "viscosity value" is preferably 100 mPa·s, more preferably 200 mPa·s, still more preferably 400 mPa·s. The upper limit value of the "viscosity value" is preferably 100,000 mPa·s, which is an upper limit value of a cellulose compound that is actually available. The number average molecular weight (g/Mol) corresponding to the "viscosity value" of from 100 mPa·s to 200,000 mPa·s is from about 30,000 to about 300,000. The weight average molecular weight (g/Mol) is from about 100,000 to about 1,000,000 (from catalog values of methylcellulose and hydroxypropyl methylcellulose sold under the trademark METOLOSE series manufactured by Shin-Etsu Chemical Co., Ltd. and the trademark METOCEL series manufactured by The Dow Chemical Company).

The nonionic water-soluble cellulose compound in a solid state is usually a solid particle having a particle diameter of the order of from 1 µm to 100 µm. In addition, the compound has a feature of having a low critical solution temperature (LCST), that is, T0. The LCST refers to a temperature at which dissolution starts when the water temperature becomes lower than T0 in a temperature decrease process, and a polymer in a solution is gelled or subjected to phase separation when the water temperature becomes higher than T0 in a temperature increase process.

When the water-soluble cellulose compound is completely dissolved in a solvent (e.g., water) in the vicinity of room temperature, the solution becomes transparent. In a process in which the solution is increased in temperature again, the gelation or phase separation from the solvent at T0 is observed as turbidness of the aqueous solution, and hence T0 is called "cloud point". In the case where undissolved water-soluble cellulose particles (usually, each having a diameter of from 1 µm to 100 µm) are dissolved in water, when the water-soluble cellulose particles are first dispersed at the cloud point T0 or more and then dissolved by decreasing the water temperature, the particles start being gradually dissolved from the surface, but keep a dispersion state of solid fine particles without being completely dissolved. When the water temperature is further decreased to the vicinity of room temperature, a complete solution is obtained. When the solution is increased in temperature again, the solution is gelled or subjected to phase separation from the solvent in the vicinity of the cloud point, but the water-soluble cellulose compound does not return to the original dispersion liquid of undissolved solid fine particles. It seems that, in MC and HPMC, a gel in which a water molecule is taken in a network of the cellulose polymer is formed, and in HPC, phase separation occurs between a solid phase of the cellulose polymer and a water phase. The low critical solution temperature (hereinafter sometimes referred to as "dissolution temperature") and the cloud point are each a designation with focus being given on the temperature decrease process or the temperature increase process, and are substantially matched with each other although there is a slight shift therebetween due to the history of the temperature decrease process or the temperature increase process. In the following description, the low critical solution temperature and the cloud point are dealt with equivalently.

The cloud point of the nonionic water-soluble cellulose compound usually falls within a range of from 40° C. to 70° C. also depending on the pH of the aqueous solution and the like (Collection of Papers on Polymer, vol. 38 (1981), p. 133-137, J. Polym. Sci. C, Vol. 36 (1971), p. 491-508). For example, the cloud points of HPMC, MC, and HPC, which are typical nonionic water-soluble cellulose compounds, are about 60° C., about 40° C., and about 40° C., respectively.

The term "enteric cellulose compound" refers to an acid-resistant cellulose compound (polymer). The term specifically refers to a compound obtained by etherifying a hydrogen atom of a hydroxy group of a cellulose with, for example, phthalic acid, acetic acid, or succinic acid having a carboxyl group. Examples of the enteric cellulose compound may include hydroxypropyl methylcellulose phthalate (HPMCP), hydroxypropyl methylcellulose acetate succinate (HPMCAS), and cellulose acetate phthalate (CAP).

The HPMCP is also referred to as hypromellose phthalate, and is obtained by, for example, allowing phthalic anhydride to react with hypromellose (HPMC) through use of anhydrous sodium acetate as a catalyst, to thereby further introduce a carboxybenzoyl group (—COC$_6$H$_4$COOH). The carboxybenzoyl group contains a carboxyl group and exhibits hydrophobicity and acid resistance by itself. In contrast, in a mildly acidic area to a neutral area, dissolution occurs through the dissociation of the carboxybenzoyl group. Thus, the dissolution pH, that is, pH to be a threshold value at which dissolution starts substantially at such value or more may be varied depending on the bonding amount of the carboxybenzoyl group.

As product examples, the hydroxypropyl methylcellulose phthalate sold under the trade name HP-55 (substitution type: 200731) and HP-50 (substitution type: 220824), which are two types having different dissolution pH's, and HP-55S, which has a higher degree of polymerization than HP-55 and is excellent in film strength, are available from Shin-Etsu Chemical Co., Ltd. and LOTTE Fine Chemical Co., Ltd. The dissolution pH's of HP-50 and HP-55 are substantially pH 5.0 and pH 5.5, respectively.

The HPMCAS is also referred to as hypromellose acetate succinate, and is obtained by, for example, allowing acetic anhydride and succinic anhydride to react with hypromellose (HPMC), to thereby further introduce an acetyl group (—COCH$_3$) and a succinoyl (also referred to as "succinyl") group (—COC$_2$H$_4$COOH). A carboxyl group (—COOH group) in the succinoyl group is important for expression of an enteric function. There is no particular limitation on the content of a substituent of the HPMCAS. A methoxy group content is preferably from 12 mass % to 28 mass %, more preferably from 20 mass % to 26 mass %. A hydroxypropoxy group content is preferably from 4 mass % to 23 mass %, more preferably from 5 mass % to 10 mass %. An acetyl group content is preferably from 2 mass % to 16 mass %, more preferably from 5 mass % to 14 mass %. A succinoyl group content is preferably from 2 mass % to 20 mass %, more preferably from 4 mass % to 18 mass %.

As a product example of hypromellose acetate succinate, for example, AQOAT (trademark) series products are available from Shin-Etsu Chemical Co., Ltd. In the series, there are three kinds of substitution grades AS-L, AS-M, and AS-H based on the degrees of substitution with a succinoyl group and an acetyl group. In the order of the grade (L, M, or H), an acetyl group content is set to be decreased while a succinoyl group content, that is, a carboxyl group content is set to be increased, and the dissolution pH is set to be increased. The dissolution pH's of AS-L, M, and H are substantially pH 5.0, pH 5.5, and pH 6.0, respectively.

In addition, hypromellose acetate succinate products having various degrees of substitution are available as one of AFFINISOL (trademark) series products from The Dow Chemical Company and one of AquaSolve (trademark) series from Ashland Inc.

The CAP is also called cellacefate (British Pharmacopoeia), cellulose acetate phthalate (Japanese Pharmacopoeia), cellulosi acetas phthalas (European Pharmacopoeia), or cellacefate (US Pharmacopeia). The CAP is obtained by allowing phthalic anhydride to react with cellulose acetate (acetylated cellulose) through use of anhydrous sodium acetate or the like as a catalyst, to thereby introduce a carboxybenzoyl group (—COC$_6$H$_4$COOH). The CAP is commercially available as Aquateric (trademark) series products from FMC Technologies Inc. or from Eastman Chemical Company.

Those enteric cellulose compounds are insoluble in water in a non-neutralized state and are solubilized by being at least partially neutralized with a basic neutralizer. The term "non-neutralized state" means that free acid residues (for example, carboxylic acid residues of phthalic acid, succinic acid, and acetic acid moieties that are present in molecules) are not neutralized. In the present disclosure, it is preferred to use a non-neutralized enteric cellulose compound.

The "methacrylic acid copolymer" is also referred to as "methacrylate copolymer". The methacrylic acid copolymer is a polymer having a methacrylic acid monomer unit in a skeleton thereof.

The methacrylic acid copolymer is more preferably formed of a methacrylic acid monomer unit serving as an anionic group and an alkyl ester monomer unit of acrylic acid or methacrylic acid that is neutral. An alkyl that forms an ester bond with acrylic acid or methacrylic acid may be, for example, an alkyl having 1 to 4 carbon atoms, preferably an alkyl having 1 to 3 carbon atoms. A more specific example of the alkyl ester of acrylic acid or methacrylic acid may be at least one kind selected from the group consisting of methyl methacrylate, ethyl methacrylate, butyl methacrylate, methyl acrylate, ethyl acrylate, and butyl acrylate.

The methacrylic acid copolymer is preferably enteric. The methacrylic acid copolymer may be more preferably, for example, an enteric methacrylic acid copolymer such as a copolymer of methacrylic acid (formula (I)), methyl methacrylate (formula (II)) and methyl acrylate (formula (III)); or a copolymer of methacrylic acid (formula (I)) and ethyl acrylate (formula (IV)) shown below (Non-patent Literature 1, Chapter 9).

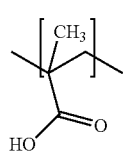

(I)

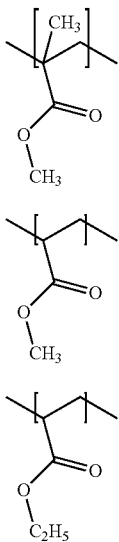

The methacrylic acid copolymer preferably contains at least 5%, preferably 5% to 70%, particularly 8% to 60%, more preferably 30% to 60% of the methacrylic acid monomer unit when the total number (total number of units or total number of groups) of monomers forming the copolymer is set to 100. The ratio of each monomer unit may be easily converted into mass % using the molecular weight of each monomer unit.

The methacrylic acid copolymer is preferably a polymer formed of 40 mass % to 60 mass % of methacrylic acid (molecular weight: 86.04), and 60 mass % to 40 mass % of methyl methacrylate (molecular weight: 100.05) or 60 mass % to 40 mass % of ethyl acrylate (molecular weight: 100.05) (e.g., a methacrylic acid copolymer sold under the tradename EUDRAGIT (trademark) L100 or the tradename EUDRAGIT (trademark) L100-55). Of those, EUDRAGIT (trademark) L100-55, that is, a copolymer formed of 50 mass % of methacrylic acid and 50 mass % of ethyl acrylate, is particularly suitable. EUDRAGIT (trademark) L30D-55 is an aqueous dispersion liquid containing about 30 mass % of EUDRAGIT (trademark) L100-55. Those methacrylic acid copolymers are each set to be dissolved when the pH is about 5.5 or more.

Another preferred example is a polymer formed of 5 mass % to 15 mass % of methacrylic acid, 10 mass % to 30 mass % of methyl methacrylate, and 50 mass % to 70 mass % of methyl acrylate (molecular weight: 86.04). The polymer is more specifically EUDRAGIT (trademark) FS, that is, a copolymer formed of 10 mass % of methacrylic acid, 25 mass % of methyl methacrylate, and 65 mass % of methyl acrylate. EUDRAGIT (trademark) FS30D is a dispersion liquid containing about 30 mass % of the methacrylic acid copolymer sold under the trade name EUDRAGIT (trademark) FS. This methacrylic acid copolymer is set to be dissolved when the pH is about 7 or more and may be used in some cases when the delivery to the large intestine, which is an environment having a higher pH, is intended.

In general, in the above-mentioned enteric methacrylic acid copolymer, an aqueous emulsion containing significantly small colloid particles are produced in advance through a copolymerization process in an aqueous solution from a monomer level by an emulsion polymerization process. Thus, an aqueous dispersion liquid of significantly fine colloid particles having an average particle diameter of less than 1 μm is obtained even without a dissolution step through neutralization of a solid polymer component with a basic neutralizer.

As a water dispersion liquid equivalent to the methacrylic acid copolymer sold under the trade name EUDRAGIT series (Evonik Industries AG) L30D-55 and a commercialized methacrylic acid copolymer equivalent thereto, there are also given a methacrylic acid copolymer sold under the trade name Kollicoat series (BASF) MAE 30D/DP and the trade name Polykid series (Sanyo Chemical Industries, Ltd.) PA-30. However, the present invention is not always limited thereto. Those water dispersion liquids (aqueous emulsions) usually contain less than 0.3% of a residual monomer, and a trace amount of Polysorbate 80 and sodium lauryl sulfate for the purpose of a production process thereof and stabilization. Those components are acceptable as impurities inevitably contained in the hard capsule film and the hard capsule-preparing solution according to the present disclosure.

The "(meth)acrylic acid alkyl ester copolymer" is a (meth)acrylic acid copolymer that is substantially neutral, and is mainly formed of an alkyl ester neutral monomer unit of methacrylic acid or acrylic acid. An alkyl that forms an ester bond with acrylic acid or methacrylic acid may be, for example, an alkyl having 1 to 4 carbon atoms, preferably an alkyl having 1 to 3 carbon atoms. A more specific example of the alkyl ester of acrylic acid or methacrylic acid may be at least one kind selected from the group consisting of methyl methacrylate, ethyl methacrylate, butyl methacrylate, methyl acrylate, ethyl acrylate, and butyl acrylate. In order for the (meth)acrylic acid alkyl ester copolymer to be substantially neutral, the ratio of the neutral monomer is, for example, more than 95 mass %, more than 98 mass %, more than 99 mass %, or 100 mass %. However, the presence of an ionic group in the polymer is not completely eliminated, and a (meth)acrylic acid copolymer, in which an ionic group content, in particular, an anionic group content is less than 5 mass %, preferably less than 2 mass %, preferably less than 1 mass %, may be contained.

The (meth)acrylic acid alkyl ester copolymer is preferably water-insoluble.

A copolymer (EUDRAGIT (trademark) NE or EUDRAGIT (trademark) NM type) formed of 20 mass % to 40 mass % of methyl methacrylate (molecular weight: 100.05) and 60 mass % to 80 mass % of ethyl acrylate (molecular weight: 100.05) is more preferred. Of those, EUDRAGIT (trademark) NE, which is a copolymer formed of 70 mass % of ethyl acrylate and 30 mass % of methyl methacrylate, is suitable. In each case, less than 5 mass %, preferably less than 2 mass %, more preferably less than 1 mass % of methacrylic acid (molecular weight: 86.04) may be contained.

Those water-insoluble (meth)acrylic acid alkyl ester copolymers each have a glass transition temperature of less than 100° C. or a minimum film-forming temperature (MFT) of less than 50° C. and have the following effect. In particular, when a dispersion liquid containing colloid particles of an enteric methacrylic acid copolymer is dried to form a film, fusion between the particles is accelerated to obtain a dried film that is transparent and less liable to be cracked. In addition, the water-insoluble (meth)acrylic acid alkyl ester copolymer has an advantage of not impairing acid resistance in an appropriate addition amount.

Also in the above-mentioned water-insoluble (meth)acrylic acid alkyl ester copolymer, an aqueous emulsion containing significantly small colloid particles may be produced in advance through a copolymerization process in an aqueous solution from a monomer level by an emulsion polymerization process. Thus, an aqueous dispersion liquid of significantly fine colloid particles having an average particle diameter of less than 1 μm is obtained even without a dissolution step through neutralization of a solid polymer component with a basic neutralizer.

The "polyvinyl alcohol (PVA)" is a polymerized product obtained by saponifying polyvinyl acetate. As the polyvinyl alcohol (PVA), there are usually given a completely saponified product having a degree of saponification of 97% or more, which is represented by the following formula (1), and a partially saponified product having a degree of saponification of from 78% to 96%, which is represented by the following formula (2). In the present disclosure, any of the completely saponified product and the partially saponified product may be used. There is no particular limitation, and a partially saponified product having a degree of saponification n/(n+m) of from about 78% to about 90%, in particular, from about 87% to about 90% is preferably used.

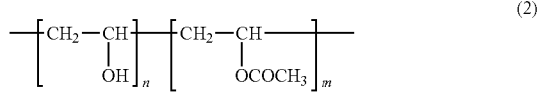

(where "n" and "m" represent any integers.)

There is no particular limitation on an average degree of polymerization (n) of PVA as long as the film-forming ability can be exhibited. The average degree of polymerization (n) is usually from about 400 to about 3,300, particularly preferably from about 1,000 to about 3,000. The weight average molecular weight of the PVA is calculated to be from about 18,000 to about 200,000 based on the above-mentioned average degree of polymerization and degree of saponification, but the present invention is not particularly limited thereto. Through addition of the PVA, appropriate mechanical strength (elastic modulus and cracking resistance) can be imparted to a capsule film while an enteric property is maintained.

The PVA copolymer is preferably a high molecular copolymer obtained by copolymerizing acrylic acid and methyl methacrylate through use of the above-mentioned partially saponified PVA as a skeleton. As a commercially available PVA copolymer, for example, there may be given a PVA copolymer sold under the trade name POVACOAT (trademark) series (Nisshin Kasei Co., Ltd.).

The PVA copolymer is preferably a high molecular copolymer obtained by copolymerizing acrylic acid and methyl methacrylate through use of the above-mentioned partially saponified PVA as a skeleton. As a commercially available PVA copolymer, for example, there may be given POVACOAT (trademark) series (Nisshin Kasei Co., Ltd.).

The enteric hard capsule film according to the present disclosure may further contain a plasticizer, a surfactant (emulsifier), a base (excluding a nonionic water-soluble cellulose compound), a binder (excluding PVA), a coating agent, and the like, each of which is pharmaceutically acceptable and is acceptable as a food additive. In addition, the enteric hard capsule film according to the present disclosure may contain a release-sustaining agent, a solubilizing agent, a solubilizer, and the like for controlling solubility, in particular, dissolution characteristics in a neutral pH region. As the above-mentioned additives that are acceptable as pharmaceutical additives, for example, those which are described according to the above-mentioned applications in Japanese Pharmaceutical Excipients Directory 2016 (edited by IPEC Japan, Yakuji Nippo, Limited) may be used, but the present invention is not limited thereto. Those additives are also classified in an overlapping manner into a plurality of applications in some cases.

The plasticizer is not always limited to the specific substances described in the above-mentioned Japanese Pharmaceutical Excipients Directory. There is no particular limitation on the plasticizer as long as the plasticizer can be used for pharmaceutical or food compositions and can impart plasticity to a capsule film when being added thereto. An appropriate substance generally has a molecular weight (Mw) of from 100 to 20,000 and has one or a plurality of hydrophilic groups, for example, a hydroxyl group, an ester group, and an amino group, in one molecule. Examples thereof may include dioctyl adipate, polyester adipate, epoxidized soybean oil, a epoxyhexahydrophthalic acid diester, kaolin, triethyl citrate, glycerin, a glycerin fatty acid ester, sesame oil, a dimethyl polysiloxane-silicon dioxide mixture, D-sorbitol, a medium-chain fatty acid triglyceride, corn starch-derived sugar alcohol liquid, triacetin, concentrated glycerin, castor oil, phytosterol, diethyl phthalate, dioctyl phthalate, dibutyl phthalate, butyl phthalyl butyl glycolate, propylene glycol, polyoxyethylene (105) polyoxypropylene (5) glycol, polysorbate 80, macrogol, isopropyl myristate, a cotton seed oil-soybean oil mixture, glycerin monostearate, isopropyl linoleate, and polyethylene glycols having various molecular weights (macrogol 400, 600, 1500, 4000, and 6000). Of those, polyethylene glycol is particularly suitable from the viewpoints of being excellent in compatibility and imparting high glossiness. The weight average molecular weight of the polyethylene glycol is not particularly limited, and is preferably from 200 to 35,000 from the viewpoint of imparting high glossiness.

The surfactant (also referred to as emulsifier) is used as a solubilizer, a suspending agent, an emulsifier, a dispersant, a solubilizing agent, a stabilizer, or the like. Specific examples thereof include benzalkonium chloride, benzethonium chloride polyoxyethylene (40) monostearate (polyoxyl 40 stearate*), sorbitan sesquioleate (sorbitan sesquioleate*), polyoxyethylene (20) sorbitan monooleate (polysorbate 80*), glyceryl monostearate (glycerin monostearate*), sodium lauryl sulfate, and polyoxyethylene lauryl ether (lauromacrogol*) (*: notation in the Japanese Pharmacopoeia). The examples also include a sodium alkyl benzene sulfonate, a sucrose fatty acid ester, polyethylene glycol monooleate, polyethylene glycol dioleate, a propylene glycol fatty acid ester (propylene glycol monostearate), polyoxyethylene hydrogenated castor oil, polyoxyethylene glycerin monostearate, polyoxyethylene (160) polyoxypropylene (30) glycol, and polyoxyethylene nonylphenyl ether.

The enteric hard capsule film according to the present disclosure may further contain, for example, a lubricant, a metal sequestering agent, a colorant, a light-shielding agent, or a binder, at up to about 5 mass %. Examples of the metal sequestering agent may include ethylenediaminetetraacetic acid, acetic acid, boric acid, citric acid, gluconic acid, lactic acid, phosphoric acid, tartaric acid, or salts thereof, metaphosphate, dihydroxyethylglycine, lecithin, β-cyclodextrin, or combinations thereof.

The lubricant is not particularly limited as long as the lubricant can be used for a pharmaceutical or food composition. Examples thereof may include calcium stearate, magnesium stearate, sodium stearyl fumarate, carnauba wax, starch, a sucrose fatty acid ester, light anhydrous silicic acid, macrogol, talc, and a hydrogenated vegetable oil.

Examples of the metal sequestering agent may include ethylenediaminetetraacetic acid, acetic acid, boric acid, citric acid, gluconic acid, lactic acid, phosphoric acid, tartaric acid, or salts thereof, metaphosphate, dihydroxyethylglycine, lecithin, β-cyclodextrin, and combinations thereof.

The colorant and the light-shielding agent are not particularly limited as long as the colorant and the light-shielding agent can be used for a pharmaceutical or food composition. Examples of the colorant may include gambir tannin powder, turmeric extract, methylrosaniline chloride, yellow iron oxide, yellow iron sesquioxide, Opaspray K-1-24904, orange essence, brown iron oxide, carbon black, caramel, carmine, carotene liquid, β-carotene, photosensitizer 201, licorice extract, gilt, *Sasa veitchii* extract, black iron oxide, light anhydrous silicic acid, Daemonorops draco, zinc oxide, titanium oxide, iron sesquioxide, disazo yellow, Food Blue No. 1 and its aluminum lake, Food Blue No. 2 and its aluminum lake, Food Yellow No. 4 and its aluminum lake, Food Yellow No. 5 and its aluminum lake, Food Green No. 3 and its aluminum lake, Food Red No. 2 and its aluminum lake, Food Red No. 3 and its aluminum lake, Food Red No. 102 and its aluminum lake, Food Red No. 104 and its aluminum lake, Food Red No. 105 and its aluminum lake, Food Red No. 106 and its aluminum lake, sodium hydroxide, talc, sodium copper chlorophyllin, copper chlorophyll, hull-less barley green tea extract powder, hull-less barley green tea extract, phenol red, sodium fluorescein, d-borneol, malachite green, octyldodecyl myristate, methylene blue, medicinal carbon, riboflavin butyrate, riboflavin, green tea powder, ammonium manganese phosphate, sodium riboflavin phosphate, rose oil, turmeric color, chlorophyll, carminic acid color, Food Red No. 40 and its aluminum lake, water-soluble annatto, sodium iron chlorophyllin, dunaliella carotene, capsicum color, carrot carotene, potassium norbixin, sodium norbixin, palm oil carotene, beet red, grape pericarp color, black currant color, monascus color, safflower red color, safflower yellow color, marigold color, sodium riboflavin phosphate, madder color, alkanet color, aluminum, sweet potato carotene, shrimp color, krill color, orange color, cacao color, cacao carbon black, Japanese persimmon color, crayfish color, carob color, fish scale foil, silver, kusagi (Clerodendrum trichotomum) color, gardenia blue color, gardenia red color, gardenia yellow color, kooroo color, chlorophyllin, kaoliang color, bone carbon black, bamboo grass color, shea nut color, shikon (lithospermum root) color, red sandalwood color, vegetable carbon black, sappan color, spirulina color, onion color, tamarind color, corn color, tomato color, peanut color, phaffia color, pecan nut color, monascus yellow, annatto powder, Haematococcus algae color, purple sweet potato color, purple corn color, purple yam color, vegetable oil soot color, lac color, rutin, enju (*Styphnolobium japonicum*) extract, buckwheat whole-plant extract, logwood color, red cabbage color, red rice color, red radish color, adzuki bean color, *Hydrangea serrata* leaf extract, sepia color, uguisu-kagura (*Lonicera gracilipes*) color, elderberry color, olive tea, cowberry color, gooseberry color, cranberry color, salmonberry color, strawberry color, dark sweet cherry color, cherry color, thimbleberry color, dewberry color, pineapple juice, huckleberry color, grape juice color, black currant color, blackberry color, plum color, blueberry color, berry juice, boysenberry color, whortleberry color, mulberry color, morello cherry color, raspberry color, red currant color, lemon juice, loganberry color, chlorella powder, cocoa, saffron color, beefsteak plant color, chicory color, laver color, hibiscus color, malt extract, paprika powder, red beet juice, and carrot juice.

Examples of the light-shielding agent may include titanium oxide, a calcium compound, iron sesquioxide, yellow iron sesquioxide, black iron oxide, Food Blue No. 1 aluminum lake, Food Blue No. 2 aluminum lake, Food Yellow No. 4 aluminum lake, Food Yellow No. 5 aluminum lake, Food Green No. 3 aluminum lake, Food Red No. 2 aluminum lake, Food Red No. 3 aluminum lake, Food Red No. 102 aluminum lake, Food Red No. 104 aluminum lake, Food Red No. 105 aluminum lake, Food Red No. 106 aluminum lake, and Food Red No. 40 aluminum lake.

In a pharmaceutical hard capsule, in order to prevent deterioration of a content caused by an ultraviolet ray or the like, in particular, titanium oxide or a calcium compound may be added as the light-shielding agent. As a calcium-containing compound, there are given an inorganic calcium salt, such as calcium carbonate or calcium hydrogen carbonate, calcium hydroxide, calcium oxide, a calcium complex, such as dolomite or hydroxyapatite, and other compounds each containing a calcium element.

2. Enteric Hard Capsule

A first embodiment according to the present disclosure relates to an enteric hard capsule.

Specifically, the first embodiment relates to an enteric hard capsule including a film containing a first component and a second component, and further containing at least one component selected from the group consisting of a third component, a fourth component, and a fifth component. The first component is a nonionic water-soluble cellulose compound having a viscosity value within a range of from 100 mPa·s to 100,000 mPa·s. The second component is an enteric methacrylic acid copolymer. The third component is an enteric cellulose compound. The fourth component is a water-insoluble (meth)acrylic acid alkyl ester copolymer. The fifth component is at least one kind selected from the group consisting of polyvinyl alcohol, a plasticizer, and a surfactant. Of those, the second component and the third component are used for imparting an enteric function, and the first component is used mainly for assisting in formation of a film to be a capsule shape that is independent without a support. The fourth component and the fifth component are used mainly for causing the independent capsule film to obtain mechanical strength suitable as a hard capsule while maintaining the enteric function.

The viscosity value of the nonionic water-soluble cellulose compound to be used as the first component in the present disclosure is set within a range of from 100 mPa·s to 100,000 mPa·s for the following reason.

In the case of a hypromellose hard capsule for oral administration which does not depend on pH and in which solubility without delay is heavily weighed, those containing water-soluble cellulose having a labeled viscosity (viscosity grade) of from 3 mPa·s to 15 mPa·s have hitherto been used (JP 08-208458 A, JP 2001-506692 A, JP 2010-270039 A, and JP 2011-500871 A). In those, water-soluble cellulose, in particular, HPMC accounts for substantially 100% in a film (containing about 0 mass % to about 5 mass % of a gelling agent, a gelling aid, a light-shielding agent, a colorant, and the like, and about 0 mass % to about 10 mass % of residual moisture in some cases). In a dissolution test using acetaminophen as an indicator, the dissolution speed thereof hardly depends on pH and is determined by the molecular weight of water-soluble cellulose, that is, the viscosity value thereof. Usually, in a test liquid of pH 1.2, a test liquid of pH 6.8, and pure water, acetaminophen in the capsule is eluted by 100% within 30 minutes. Meanwhile, dissolution delay tends to occur at a viscosity value of 100 mPa·s or more, and hence the above-mentioned materials have hitherto been hardly used as a fast-dissolving capsule film material.

In the present disclosure, it is considered that, as compared to the related art, the characteristics suitable for a hard capsule can be realized through addition of a small amount of a nonionic water-soluble cellulose compound having a significantly high viscosity such as a viscosity value of 100 mPa·s or more, that is, a significantly high molecular weight to an enteric polymer. Although not bound by a theory, it is considered that the nonionic water-soluble cellulose compound generally exhibits a function as a filler for a relatively brittle enteric polymer. Further, due to the significantly high molecular weight, in the test liquid (first liquid) of pH 1.2, the nonionic water-soluble cellulose compound appropriately suppresses swelling caused by intrusion of moisture, and does not impair the acid resistance function of the enteric polymer that is a main component.

Meanwhile, in the test liquid of pH 6.8, the enteric polymer accelerates rapid dissolution. Therefore, even when water-soluble cellulose having a viscosity value of 100 mPa·s or more is contained, dissolution delay is less liable to occur.

In the present disclosure, the enteric methacrylic acid copolymer serving as the second component is a constituent feature essential for realizing the enteric hard capsule according to the present disclosure. As the original properties of the enteric base, the enteric methacrylic acid copolymer is significantly stable (Non-patent Literature 6, in particular, FIG. 3) as compared to the enteric cellulose compound in long-term storage, and further has a low water vapor permeation rate, that is, an advantage of being excellent in moisture-proof property of a film (Non-patent Literature 6, in particular, Table 2).

However, due to the polymer skeleton thereof, the enteric methacrylic acid copolymer is liable to form a hard and brittle film. In order to compensate for this shortcoming, the enteric cellulose compound (third component) may be mixed. The third component can achieve mechanical strength preferred as a hard capsule film while securing a sufficient enteric property. Simultaneously, through blending of the third component in addition to the second component among options of an enteric polymer that is pharmaceutically acceptable, the pH dependency can be more flexibly controlled. That is, the dissolution characteristics in an intermediate pH region of from about pH 4 to about pH 5 can be controlled. Meanwhile, as another embodiment according to the present disclosure, a part or an entirety of the enteric cellulose compound can be substituted with the water-insoluble (meth)acrylic acid alkyl ester copolymer serving as the fourth component. The fourth component can improve mechanical strength, in particular, ease of cracking without deteriorating acid resistance performance. In addition, unlike the third component, when a completely dissolved or finely granulated dispersion liquid is obtained, it is not required to perform neutralization, and hence the concentration of a residual salt in the film can be suppressed.

In addition to the first component, the second component, the third component, and the fourth component, at least one kind selected from the group consisting of PVA, a plasticizer, and a surfactant may be added as the fifth component. The fifth component is preferred because the effect of imparting appropriate hardness and ease of cracking is obtained, and the transparency of the film can be maintained. Some plasticizers and surfactants, such as triethyl citrate (TEC), polyethylene glycol (PEG), and propylene glycol (PG), are useful also for reducing and stabilizing particle diameters in a dispersion liquid of the enteric polymer. PVA has an effect of increasing the hardness of the film.

In the enteric hard capsule according to the first embodiment, it is preferred that, when a total mass of the first component, the second component, the third component, the fourth component, and the fifth component contained in the film is set to 100 mass %, and when a ratio of the first component is represented by $\alpha$ mass %, a ratio of the second component is represented by $\beta$ mass %, a ratio of the third component is represented by $\gamma$ mass %, a ratio of the fourth component is represented by $\sigma$ mass %, and a ratio of the fifth component is represented by $\varphi$ mass %, a total ratio of the enteric polymer (second component and third component) and the fourth component $(\beta+\gamma+\sigma)/(\alpha+\beta+\gamma+\sigma+\varphi)$ be 0.5 or more. The value of $(\beta+\gamma+\sigma)/(\alpha+\beta+\gamma+\sigma+\varphi)$ is more preferably 0.55 or more, still more preferably 0.6 or more. Simultaneously, $(\beta+\gamma)/(\beta+\gamma+\sigma)$ is preferably 0.4 or more, more preferably 0.5 or more. With this, sufficient acid resistance as the enteric hard capsule can be exhibited.

Meanwhile, in order to maintain appropriate hardness and cracking resistance of the capsule film, the upper limit of $(\beta+\gamma+\sigma)/(\alpha+\beta+\gamma+\sigma+\varphi)$ is set to 0.9 or less, preferably 0.8 or less.

It is preferred that the ratio of the nonionic water-soluble cellulose compound serving as the first component be $0.05 \leq \alpha/(\alpha+\beta+\gamma+\sigma+\varphi) \leq 0.5$. When the ratio is less than 0.05, the capsule film is liable to be cracked. When the ratio is more than 0.5, deterioration of acid resistance at pH 1.2 or deterioration of solubility at pH 6.8 (neutral) is liable to be caused. The ratio is more preferably $0.07 \leq \alpha/(\alpha+\beta+\gamma+\sigma+\varphi) \leq 0.4$. In the case where the viscosity value is more than about 1,000 mPa·s, when $\alpha$ is more than 30 mass %, dissolution is liable to be slow even in a buffer solution of pH 6.8. When it is required that the capsule be transferred to the intestines to be rapidly dissolved, it is preferred to use a water-soluble cellulose compound having a viscosity value of from 100 mPa·s to 1,000 mPa·s. Alternatively, when a water-soluble cellulose compound having a viscosity value of from 1,000 mPa·s to 10,000 mPa·s is used, the ratio $\alpha$ thereof is set to preferably less than 30 mass %, more preferably less than 20 mass %. Meanwhile, when it is required that the capsule be transferred to the intestines and released in a sustained manner (about 60 minutes or more are taken for dissolution), it is preferred to use water-soluble cellulose having a viscosity value of 10,000 mPa·s or more.

Regarding the ratios of the second component and the third component that form the enteric polymer, the ratio $\beta/(\beta+\gamma)$ of the enteric methacrylic acid copolymer is preferably 0.1 or more, more preferably 0.2 or more, still more preferably 0.4 or more. The upper limit thereof may be 1 or less, that is, $\gamma=0$ may be established. The reason for this is as described below. As the properties of the enteric polymer, the enteric methacrylic acid copolymer is more chemically stable than the enteric cellulose compound, and a free carboxylic acid is hardly generated through decomposition of a carboxyl group in long-term storage under high humidity. In addition, the enteric methacrylic acid copolymer also has a low water vapor permeation rate, that is, an advantage of being excellent in moisture-proof property of a film.

As a more preferred embodiment, when the ratio $\gamma$ of the third component is reduced, it is preferred that a part or an entirety of the enteric cellulose compound serving as the third component be substituted with the water-insoluble (meth)acrylic acid alkyl ester copolymer of the fourth component. It is more preferred that $\gamma=0$ be established. The water-insoluble (meth)acrylic acid alkyl ester copolymer has an effect of improving mechanical strength, in particular, ease of cracking of a film without deteriorating acid resistance. In the case of $\gamma=0$, $\beta/(\alpha+\beta+\gamma+\sigma+\varphi)$, that is, $\beta/(\alpha+\beta+\sigma+\varphi)$ is preferably 0.3 or more, more preferably 0.4 or more. Meanwhile, the enteric methacrylic acid copolymer is a material that is liable to make the capsule film brittle. Therefore, the upper limit of $\beta/(\alpha+\beta+\sigma+\varphi)$ is preferably 0.7 or less, more preferably 0.65 or less. The ratio $(\beta+\gamma+\sigma)/(\alpha+\beta+\gamma+\sigma+\varphi)$, that is, $(\beta+\sigma)/(\alpha+\beta+\sigma+\varphi)$ is preferably 0.5 or more and 0.9 or less as described above. Further, in order to maintain appropriate cracking resistance, it is preferred that $\sigma/(\alpha+\beta+\gamma+\sigma+\varphi)$, that is, $\sigma/(\alpha+\beta+\varphi)$ be set to 0.2 or more.

Even in any of the above-mentioned component ratios, the ratio $\varphi/(\alpha+\beta+\gamma+\sigma+\varphi)$ of the fifth component is set to preferably 0.15 or less, more preferably 0.1 or less. When the fifth component is contained in an excess amount, a film that is so soft, in particular, under high humidity as to be unsuitable as a hard capsule may be obtained. In addition, acid resistance may become insufficient due to the water solubility of the fifth component.

In the present disclosure, a mixture of a plurality of kinds of nonionic water-soluble cellulose compounds having different viscosity values of 100 mPa·s or more or having different substitution types may be used. The entire amount of the nonionic water-soluble cellulose compounds having a viscosity value of 100 mPa·s or more is regarded as the first component, and the ratio thereof may be represented by $\alpha$ mass %. The same also hereinafter applies to the second, third, and fourth components. When a plurality of kinds of enteric methacrylic acid copolymers are used, the entire amount thereof is regarded as the second component, and the ratio thereof is represented by $\beta$ mass %. When a plurality of kinds of enteric cellulose compounds are used, the entire amount thereof is regarded as the third component, and the ratio thereof is represented by $\gamma$ mass %. When a plurality of kinds of water-insoluble (meth)acrylic acid alkyl ester copolymers are used, the entire amount thereof is regarded as the fourth component, and the ratio thereof is represented by $\sigma$ mass %. Also regarding the fifth component, when at least two kinds selected from the group consisting of PVA, a plasticizer, and a surfactant are simultaneously used, the entire amount thereof is regarded as the fifth component, and the ratio thereof is represented by $\varphi$ mass %.

In addition to the first component, the second component, the third component, the fourth component, and the fifth component, a lubricant, a metal sequestering agent, a colorant, a light-shielding agent, and residual moisture may be contained. When the total mass of the first component, the second component, the third component, the fourth component, and the fifth component contained in the film is represented by X, and the total mass of the lubricant, the metal sequestering agent, the colorant, and the light-shielding agent is represented by $\varepsilon$, $\varepsilon/X$ may be set within a range of 0.2 or less, more preferably 0.1 or less, still more preferably 0.05 or less.

In the capsule film according to the present disclosure, the presence of a salt caused by at least partial neutralization of the enteric polymer formed of the enteric methacrylic acid copolymer and/or the enteric cellulose compound, and the presence of a neutralized product of another film component in association with the presence of the salt may be allowed. As the salt, there may be given at least one kind of salt selected from the group consisting of an alkali metal salt, an alkaline-earth metal salt, and an ammonium salt. As the salt, there may be given preferably at least one kind of salt selected from the group consisting of a sodium (Na) salt and a potassium (K) salt. The Na salt is particularly preferred.

Specifically, the carboxyl group of the enteric cellulose compound is neutralized with a metal ion such as Na, and may be stably present in a solid film as a group such as —COONa. For example, when the molar number (group number) of carboxyl residues before neutralization contained in the enteric polymer is set to 100%, the ratio of those neutralized acid (e.g., carboxylic acid) residues is preferably 50% or less, more preferably 30% or less, still more preferably 20% or less. The foregoing is called a degree of neutralization (the detailed definition of the degree of neutralization is described in a second embodiment described later). The presence of the salt in an excess amount is not preferred because the film is liable to be cracked, and deterioration of the film caused by salt precipitation and disintegration caused by excess permeation of water may occur. Meanwhile, the presence of the salt in an appropriate amount assists in water permeation and swelling of the capsule film containing the enteric polymer. The swelling of the capsule film has an effect of closing a gap between the cap and the body to more completely prevent elution. For this purpose, the degree of neutralization is preferably 2%, more preferably 5% or more.

In other words, when the total molar number of carboxyl groups forming the salts in the second component contained in the film and carboxyl groups prevented from forming the salts is set to 100 mol %, the content of the carboxyl groups forming the salts is 2 mol % or more, preferably 5 mol % or more. In addition, the content of the carboxyl groups forming the salts is 50 mol % or less, preferably 20 mol % or less, more preferably 15 mol % or less. In particular, when $\gamma=0$ is established, the content of the carboxyl groups may be set to 20 mol % or less.

In other words, when the salt contained in the capsule film is a Na salt, the content thereof is converted into a hydroxide thereof (NaOH mass) to be preferably 0.1 mass % or more, more preferably 0.2 mass % with respect to the weight of the film. Meanwhile, the content of the salt is preferably 5 mass % or less, more preferably 2 mass % or less, still more preferably 1 mass % or less. In particular, when $\gamma=0$ is established, the content of the salt may be set to 2 mass % or less.

It is preferred that 2 mass % to 10 mass % of residual moisture be contained in the capsule film according to the present disclosure in order to maintain cracking resistance. Moisture contained in an appropriate amount functions as a plasticizer while hardly influencing the solubility of the capsule. The moisture content is reversibly varied substantially in proportion to environmental humidity within a range of a relative humidity of from about 20% to about 60% although depending also on the environmental humidity at a time of capsule storage. In the present disclosure, as a moisture content value of the capsule film, a saturation value after the capsule film is stored (humidity control) at a constant relative humidity of 43% for several days at room temperature is used.

The moisture content after humidity control may be measured by a loss-on-drying method as described below.

<Method of Measuring Moisture Content of Capsule Film by Loss-On-Drying Method>

A potassium carbonate saturated salt is loaded into a desiccator to obtain an atmosphere in a constant-humidity state, and a sample (hard capsule or film) is placed in the atmosphere in this state. The desiccator is sealed, and humidity therein is controlled at 25° C. for 1 week. The following saturated salt (aqueous solution) is used for humidity control. Specifically, in the presence of a potassium acetate saturated salt, a potassium carbonate saturated salt, and an ammonium nitrate saturated salt, atmospheres having a relative humidity of about 22%, about 43%, and about 60% may be created, respectively. After the mass (wet mass) of the sample after humidity control is measured, the sample is then dried by heating at 105° C. for 2 hours, and the mass (dry mass) of the sample is measured again. From the difference between the mass before drying (wet mass) and the mass after drying (dry mass), the ratio of a moisture amount (water content) decreased by heating and drying at 105° C. for 2 hours is calculated in accordance with the following equation and is defined as the moisture content (mass %).

$$\text{Water content (\%)} = \frac{(\text{Wet mass of sample}) - (\text{Dry mass of sample})}{\text{Wet mass of sample}} \times 100$$

As the moisture content at room temperature and a relative humidity of 43%, the above-mentioned water content is preferably at least 2% or more, more preferably 3% or more, still more preferably 4% or more. When the water content is less than 2%, the resultant capsule film is liable to be cracked. Meanwhile, when the moisture content is too large, the moisture may react with a drug filled in the capsule in the case of long-term storage. Therefore, the water content is preferably 10% or less, more preferably 8% or less, still more preferably 6% or less.

It is desired that the enteric hard capsule according to the present disclosure have a shape and mechanical strength (hardness and cracking resistance) that are the same as or similar to those of a commercially available related-art hard capsule intended to be orally administered to a target such as a human or an animal. A commercially available hard capsule to be used as reference is a gelatin or hypromellose (HPMC) capsule. Thus, the thickness of a film of the capsule is 50 μm or more, preferably 60 μm or more, more preferably 70 μm or more. Meanwhile, the upper limit thereof is 250 μm or less, preferably 200 μm or less, more preferably 150 μm or less. In particular, the range of from 70 μm to 150 μm is suitable for direct use in a commercially available filling machine. It is required that, with such thickness, the film of the enteric hard capsule have mechanical strength equivalent to that of a commercially available hard capsule film. The mechanical strength can be evaluated through use of a film prepared in a strip shape by a "Tensile Strength Test" that is usually applied to a polymer film (Non-patent Literature 1, Chapter 4).

When the mechanical strength of a hard capsule film is evaluated, it is important to compare test films having the same thickness. Therefore, the mechanical strength of the film, which depends on the component composition of a hard capsule, may be evaluated for a cast film produced by a casting method through use of a preparing solution having the same component composition as the component composition of a hard capsule-preparing solution.

The cast film is produced as described below. A metal applicator is set on a glass surface or a PET film held at room temperature. A preparing solution at 50° C. to 60° C. is poured onto the glass surface or the PET film, and the metal applicator is moved at a constant speed, to thereby produce a uniform film of 100 μm. After that, the film is dried at a temperature of from room temperature to 30° C. for about 10 hours.

In order to obtain the film having a uniform thickness of 100 μm, applicators having different gaps of from 0.4 mm to 1.5 mm may be appropriately used.

The produced film may be cut into, for example, a dumbbell shape of 5 mm×75 mm (specified in JIS K-7161-2-1BA), and then subjected to a tensile test with, for example, a compact tabletop testing machine (EZ-LX manufactured by Shimadzu Corporation). Specifically, both ends of the film are set on a holder (gap length: 60 mm) and pulled at a tensile rate of 10 mm/min. Then, an elongation of the film and a curve between a stress (tensile stress) that occurs in the film and an elongation rate (strain) are determined. Typical elongation and tensile stress test results are shown in FIG. 5. An elastic modulus that is an indicator of hardness is obtained from the inclination of the curve in an elastic deformation region at a time of a low stress in FIG. 5, and an elongation rate at a breakpoint may be determined as an elongation at break (Non-patent Literature 1, Chapter 4).

It is desired that the mechanical strength be maintained under an environment of usual use conditions (temperature of from about 5° C. to about 30° C. and relative humidity of from about 20% to about 60%). For example, the mechanical strength may be evaluated by subjecting the produced film to humidity control for 1 week or more through humidity control under the conditions of 25° C. and a relative humidity of 22% (potassium acetate saturated salt is used), and after that, performing a tensile test. It is preferred that the tensile test be performed under a temperature and humidity environment of 25° C. and a relative humidity of 22%. Alternatively, the mechanical strength is evaluated by subjecting the produced film to humidity control for 1 week or more through humidity control under the conditions of 25° C. and a relative humidity of 60% (ammonium nitrate saturated salt is used), and after that, performing a tensile test. It is preferred that the tensile test be performed under the same temperature and humidity environment as that for the humidity control conditions.

An elastic modulus (Young's modulus) that is an indicator of hardness is preferably from 1 GPa to 5 GPa, more desirably from 2 GPa to 4 GPa. An elongation at break that is an indicator of cracking resistance evaluated by the tensile test is preferably from about 2% to about 30%, more preferably from about 3% to about 30%. Usually, the hardness and cracking resistance of the enteric hard capsule film according to the present disclosure have a trade-off relationship in the above-mentioned range in many cases. A coating film and a soft capsule film each are softer and have a larger elongation at break in many cases. For example, a film having an elongation at break of more than 30% is usually so soft as to be unsuitable as an independent hard capsule film in many cases. Meanwhile, when the elongation at break is less than 2%, a film is significantly liable to be cracked even in usual handling.

As described above, the moisture that is present in the capsule film in an amount of about several percent may usually influence mechanical strength, in particular, a cracking property as a plasticizer. Under use and storage conditions at a low relative humidity, when the moisture content is decreased, for example, to about 2% to about 3%, the capsule film is liable to be cracked, that is, the elongation at break thereof is liable to be decreased. Meanwhile, on a high humidity side, the moisture content is increased, and an elastic modulus is liable to be decreased. As a result, there is a problem of an elongation at break on a low humidity side, and there is a problem of an elastic modulus on a high humidity side. In the present disclosure, a film having an elongation at break of from 2% to 30% can be obtained by performing humidity control and a tensile test, in particular, under an environment of a relative humidity of 22%, which is a relatively low humidity, and a temperature of 25° C. In addition, a film having an elastic modulus of from 1 GPa to 5 GPa can be obtained by performing humidity control and a tensile test under an environment of a relative humidity of 60%, which is a relatively high humidity, and a temperature of 25° C. As a result, regarding the hardness of the enteric hard capsule according to the present disclosure, an elastic modulus within a range of from 1 GPa to 5 GPa and an elongation at break of from 3% to 30% are obtained within most of relative humidity and temperature ranges under a room condition. It is more preferred to set the elastic modulus to a range of from 2 GPa to 5 GPa and the elongation at break to a range of from 3% to 10%.

The enteric hard capsule film according to the first embodiment has a structure in which a phase containing a nonionic water-soluble cellulose compound as a main component is dispersed in a phase substantially formed of another component. This structure is referred to as "sea-island structure" assuming that the phase containing the nonionic water-soluble cellulose compound as a main component is an "island" phase, and the phase substantially formed of another component is a "sea" phase. The island phase is substantially formed of the first component. Herein, the term "substantially" means that the island phase may contain another component, in particular, the enteric cellulose polymer serving as the third component, and meanwhile, the sea phase may contain the first component that is partially dissolved. In addition, the sea phase also contains the methacrylic acid copolymer serving as the second component, a plasticizer, a surfactant (emulsifier), a lubricant, a binder, a light-shielding agent, a pigment, a color, a lubricant, and the like. As described later in Examples, the "sea-island structure" may be confirmed by observing a transverse section of a hard capsule film with a scanning electron microscope. Such "sea-island structure" is required to undergo a kind of dispersion equilibrium state in a solution state. Therefore, it is presumed that it is difficult to form the "sea-island structure" by injection molding or extrusion molding using thermoplasticity of a film component polymer. In addition, it is presumed that, even when the first component is exposed to low temperature in the vicinity of room temperature to be completely dissolved in a preparation step of a capsule-preparing solution described later, an island phase is not formed.

The size of each island phase depends on the size of a solid particle of the nonionic water-soluble cellulose compound used for preparing the hard capsule. It is preferred that the short diameter of the island phase in the hard capsule film be 0.1 μm or more and less than 30 μm. It is more preferred that the short diameter of the island phase be 0.2 μm or more and less than 20 μm.

3. Enteric Hard Capsule-Preparing Solution and Preparation Method Therefor

A second embodiment according to the present disclosure relates to a preparing solution for preparing the enteric hard capsule described in the above-mentioned section 2. The enteric hard capsule according to the present disclosure is formed of a film obtained by drying a preparing solution of this embodiment to remove a solvent.

Specifically, the second embodiment relates to an enteric hard capsule-preparing solution containing a component (i), a component (ii), a basic neutralizer, and a solvent, and further containing at least one component selected from the group consisting of a component (iii), a component (iv), and a component (v). The component (i) is a nonionic water-soluble cellulose compound having a viscosity value, preferably a "viscosity value" of a 2% aqueous solution at 20° C., within a range of from 100 mPa·s to 100,000 mPa·s. The component (ii) is an enteric methacrylic acid copolymer. The component (iii) is an enteric cellulose compound. The component (iv) is a water-insoluble (meth)acrylic acid alkyl ester copolymer. The component (v) is at least one kind selected from the group consisting of a polyvinyl alcohol copolymer, a plasticizer, and a surfactant.

In this case, it is preferred that the solvent to be used in the preparing solution contain water as a main component, in particular, be purified water. In a dissolution process of obtaining a dispersion liquid from solid powder of the nonionic water-soluble cellulose compound, the enteric cellulose compound, and/or the enteric methacrylic acid copolymer, a mixed solvent containing water and at least one kind selected from the group consisting of ethanol and anhydrous ethanol may be used. During preparation of the preparing solution in the present disclosure or in an immersion step, this ethanol is mostly evaporated. Therefore, as the preparing solution in immersion, actually, the content of moisture is 80 mass %, more preferably 90 mass % or more. Substantially 100% purified water excluding inevitably contained impurities may be used.

In this embodiment, the enteric methacrylic acid copolymer serving as the component (ii) and the enteric cellulose compound serving as the component (iii) are used independently or together as an enteric polymer. Those enteric polymers each have solubility depending on pH of a solvent, and hence are substantially insoluble in neutral water. Therefore, it is desired that those enteric polymers be dissolved or at least partially dissolved in the presence of a basic neutralizer to be used as a dispersion liquid of minute particles each having a diameter of about 10 μm, preferably 1 μm or less. When the particle diameter is larger than the foregoing, the enteric polymer may adversely influence irregularities of the surface of the capsule film and the strength of the capsule film.

In the following, the above-mentioned solution including also the case in which at least a part is neutralized and dissolved is referred to as "neutralized solution" or "partially neutralized solution". The "neutralized solution" may be a suspension liquid in which undissolved minute particles are contained in a dispersion state. There is no limitation on the basic neutralizer as long as the basic neutralizer is a compound that is pharmaceutically acceptable or is acceptable as a food additive. As the basic neutralizer, there may be given at least one kind selected from the group consisting of an alkali metal salt, an alkaline-earth metal salt, and an ammonium salt. The basic neutralizer is preferably at least one kind selected from the group consisting of a sodium salt and an ammonium salt. More preferably, as the basic neutralizer, there may be given at least one kind selected from the group consisting of sodium hydroxide, potassium hydroxide, calcium hydroxide, ammonia, and ammonium carbonate. Still more preferably, the basic neutralizer is sodium hydroxide, and in some cases, at least one kind selected from the group consisting of ammonia and ammonium carbonate.

When the basic neutralizer is ammonia, it is desired that, after a film is formed, a salt in the film be removed to the extent possible by volatilizing ammonia. When ammonia is used as the basic neutralizer, it is preferred to use HPMCAS as the enteric cellulose compound because ammonia can be easily volatilized.

In the present disclosure, instead of the enteric cellulose compound, a neutralized product obtained by neutralizing the enteric cellulose compound with the basic neutralizer in advance, which is formed into solid powder, may also be used by being dissolved or dispersed in a solvent. However, it is preferred to use a solution or a partially dissolved solution in which an enteric cellulose compound is dissolved or dispersed in a solvent, which is obtained by dispersing a non-neutralized enteric cellulose compound in the solvent and adding the basic neutralizer to the resultant in an amount capable of neutralizing at least a part thereof.

The amount of the basic neutralizer required for neutralizing and dissolving the enteric polymer (component (ii) or component (iii)) may be defined as described below.

In order to completely neutralize the enteric polymer, the basic neutralizer is added thereto in such an amount that a cation derived from the basic neutralizer becomes equivalent or more to 1 mol of a carboxyl group contained in the enteric polymer. When the cation derived from the basic neutralizer is divalent or more, the amount is reduced to 1/valence. The case in which the cation derived from the basic neutralizer is dissolved in a solvent so as to reach a substantially equivalent amount to that of the carboxyl group contained in the enteric polymer is referred to as "complete neutralization". The molar number of the equivalent cation, that is, "equivalent (equimolar amount)" refers to, for example, the molar number of the cation in an amount capable of blocking the molar number (group number) of the carboxyl residue before neutralization contained in the enteric methacrylic acid copolymer by 100% through neutralization.

Specifically, the molar number of the equivalent cation may be defined as the mass (KOH) mg/g (KOH equivalent) of KOH (molecular weight: 56.10) required for neutralizing 1 g of the intended enteric polymer. In addition, the degree of neutralization is defined by a ratio of the mass of the actually added basic neutralizer with respect to the equivalent of the basic neutralizer required for complete neutralization. When the basic neutralizer is sodium hydroxide NaOH (molecular weight: 40.00), calcium hydroxide $Ca(OH)_2$ (molecular weight: 74.09), ammonia $NH_3$ (molecular weight: 17.03), or ammonium carbonate $(NH_4)_2CO_3$ (molecular weight: 96.09), the equivalent thereof is obtained by conversion through use of the following equation.

$$\text{(Equivalent)} = \frac{\text{(KOH equivalent)} - \text{(Molecular weight of basic neutralizer/valence)}}{\text{Molecular weight of KOH}} \times 100$$

Usually, the equivalent of the basic neutralizer required for complete neutralization may be labeled by a manufacturer with a margin of from about ±10% to about ±20% as an acceptable range of the degree of substitution of the carboxyl group. A more accurate neutralization equivalent may be determined by a general titration method.

For example, when the component (ii) is the methacrylic acid copolymer sold under the trade name Eudragit L30D55, L100-55, and L100 manufactured by Evonik Industries AG, the KOH equivalent thereof is 301.2 mg/g. When the basic neutralizer is sodium hydroxide, the KOH equivalent is 214.8 mg/g. In addition, when the basic neutralizer is ammonia, the KOH equivalent is 91.4 mg/g. When the component (ii) is the methacrylic acid copolymer sold under the trade name Eudragit FS30D manufactured by Evonik Industries AG, the KOH equivalent thereof is 56.7 mg/g. When the basic neutralizer is sodium hydroxide, the KOH equivalent is 40.4 mg/g. When the basic neutralizer is ammonia, the KOH equivalent is 17.2 mg/g.

For example, when the component (iii) is hydroxypropyl cellulose phthalate sold under the trade name HP50 and HP55 manufactured by Shin-Etsu Chemical Co., Ltd., the KOH equivalents thereof are from 79.0 mg/g to 101.6 mg/g and from 101.6 mg/g to 131.7 mg/g, respectively. When the basic neutralizer is sodium hydroxide, the KOH equivalents are from 56.3 mg/g to 72.4 mg/g and from 72.4 mg/g to 93.9 mg/g, respectively. In addition, when the basic neutralizer is ammonia, the KOH equivalents are from 24.0 mg/g to 30.8 mg/g and from 30.8 mg/g to 40.0 mg/g, respectively.

When the component (iii) is HPMCAS sold under the trade name AQOAT AS-H, AS-M, or AS-L manufactured by Shin-Etsu Chemical Co., Ltd., the KOH equivalents thereof are from 22.2 mg/g to 44.4 mg/g, from 55.5 mg/g to 77.7 mg/g, and from 77.7 mg/g to 99.9 mg/g, respectively. When the basic neutralizer is sodium hydroxide, the KOH equivalents are from 15.8 mg/g to 31.7 mg/g, from 39.6 mg/g to 55.4 mg/g, and from 55.4 mg/g to 71.2 mg/g, respectively. In addition, when the basic neutralizer is ammonia, the KOH equivalents are from 6.7 mg/g to 13.5 mg/g, from 16.8 mg/g to 23.6 mg/g, and from 23.6 mg/g to 30.3 mg/g, respectively.

The degree of neutralization is defined by a mass ratio of the actually added basic neutralizer with respect to the amount of the basic neutralizer corresponding to the neutralization equivalent. The degree of neutralization is simultaneously equal to the molar number of residues blocked through neutralization of the molar number of the carboxylic acid residues.

$$\text{(Degree of neutralization)} = \frac{\text{(Mass of added basic neutralizer)}}{[\text{(Neutralization equivalent, mass)} \times \text{Mass of enteric polymer}]} \times 100$$

For example, when E (g) of NaOH is used with respect to Γ (g) of an enteric methacrylic acid copolymer L30D55, the degree of neutralization thereof is $E/(0.2418 \times \Gamma) \times 100(\%)$. Alternatively, E (g) of NaOH is used with respect to, the degree of neutralization thereof is $E/(0.065 \times \Gamma) \times 100(\%)$. A median value of 65 mg/g of a neutralization equivalent of from 56.3 to 72.4 with respect to NaOH of HP50 is applied.

Further, in the present disclosure, when Γ1 (g) of the enteric methacrylic acid copolymer L30D55 and Γ2 (g) of the enteric cellulose compound HP50 are mixed to be used, and the mixture is neutralized through use of E (g) of NaOH, the degree of neutralization with respect to the entire enteric polymer may be calculated to be $E/(0.2418 \times \Gamma 1 + 0.065 \times \Gamma 2) \times 100(\%)$. Alternatively, also when Γ1 (g) of a colloid dispersion liquid of the enteric methacrylic acid copolymer L30D55 is added to a solution obtained by neutralizing Γ2 (g) of the enteric cellulose compound HP50 through use of E (g) of NaOH, the degree of neutralization with respect to the entire enteric polymer is similarly defined.

In the enteric cellulose compound serving as the component (iii), originally, a large cellulose mass (solid particle) contained in a raw material pulp is controlled for a molecular weight by hydrolysis or chemical decomposition with an enzyme, and in addition, the resultant is pulverized by a mechanical procedure, such as mechanical milling, to obtain solid particles of the order of from 10 μm to 100 μm. In order to further miniaturize the solid particles to obtain a dispersion liquid of fine particles each having a particle diameter of about 10 μm or less, or in order to completely dissolve the solid particles, it is preferred that the degree of neutralization of the enteric cellulose compound be 50% or more so that the fine particles contained in the dispersion liquid have a size of about 10 μm or less irrespective of complete dissolution or partial dissolution. The upper limit thereof is 100%, and excess neutralization to more than 100% is not preferred because precipitation of a salt remaining in the film after being dried and the like occur.

Meanwhile, in the case of the enteric methacrylic acid copolymer serving as the component (ii), an acidic dispersion liquid (aqueous emulsion) in which significantly small colloid particles each having a diameter of more than about 0.01 μm and less than 1 μm are generated is directly obtained through a copolymerization process in an aqueous solution from a monomer level by an emulsion polymerization process. In this case, the dispersion liquid is provided as a dispersion liquid of significantly fine colloid particles having an average particle diameter of less than 1 μm even without a dissolution step through neutralization with a basic neutralizer. Specifically, there are given the above-mentioned L30D55 and the like manufactured by Evonik Industries AG. The pH of the colloid dispersion liquid of L30D55 is about 2.5.

There may also be obtained a water dispersion liquid in which enteric methacrylic acid copolymer powder (specifically, there are given L10055 and the like manufactured by Evonik Industries AG) obtained by drying the enteric methacrylic acid copolymer after being synthesized by emulsion polymerization in the solution to form solid fine particles is re-dispersed in water and partially neutralized with the basic neutralizer to form fine particles. In this case, a water dispersion liquid in which the enteric methacrylic acid copolymer is formed into sufficiently fine particles is obtained even with a degree of neutralization of from about 2% to about 20%.

In the present disclosure, it has been found that, regarding the enteric hard capsule-preparing solution containing the nonionic water-soluble cellulose compound serving as the component (i), the enteric methacrylic acid copolymer serving as the component (ii), and the enteric cellulose compound serving as the component (iii), each originally not having cold gelation ability independently, the cold gelation ability can be imparted to the enteric hard capsule-preparing solution by mixing the above-mentioned three components in the presence of the basic neutralizer. In particular, it has been found that the interaction between the nonionic water-soluble cellulose compound having a high viscosity serving as the component (i) and the enteric methacrylic acid copolymer serving as the component (ii) in the presence of an appropriate amount of the basic neutralizer is important. As the enteric hard capsule-preparing solution according to the present disclosure, there is given preferably an enteric hard capsule-preparing solution in which, as shown in FIG. 1, when the temperature is decreased from a temperature lower than the cloud point T0 (cloud point or dissolution starting temperature) of the nonionic water-soluble cellulose compound serving as the component (i), preferably at a fourth temperature T4 (abrupt viscosity increase starting temperature) lower than the second temperature T2 or a third temperature T3, storage and loss elastic moduli are abruptly increased to reach a gel state, that is, storage elastic modulus $G'$>loss elastic modulus $G''$ in the vicinity of room temperature.

The abrupt increase in viscosity in the vicinity of T4 in a cooling process of the capsule-preparing solution according to the present disclosure does not usually occur in a dispersion liquid of the enteric methacrylic acid copolymer serving as the component (ii) or a neutralized solution of the enteric cellulose compound serving as the component (iii). Thus, it is presumed that the abrupt viscosity increase in the vicinity of T4 is caused mainly by the structural viscosity of the partially dissolved nonionic water-soluble cellulose compound serving as the component (i). In particular, through the action of the nonionic water-soluble cellulose compound having a high viscosity (that is, a high molecular weight) to be used in the present disclosure, the tendency in which the viscosity is increased abruptly by one or more orders of magnitude becomes significant in a region of the temperature T4 of from about 30° C. to about 50° C. in the cooling process. In order to utilize such abrupt increase in viscosity at a time of a decrease in temperature, it is preferred that the ratio of the component (i) contained in the preparing solution be $0.05 \leq \alpha'/(\alpha'+\beta'+\gamma'+\sigma'+\varphi') \leq 0.5$. When the ratio is less than 0.05, the viscosity increase tends to be gentle. When the ratio is more than 0.5, the viscosity is too high, and it tends to be difficult to perform molding by an immersion method described later. The ratio is more preferably $0.07 \leq \alpha'/(\alpha'+\beta'+\gamma'+\sigma'+\varphi') \leq 0.4$.

In order to achieve the cold gelation characteristics in which a gel state, that is, storage elastic modulus $G'$>loss elastic modulus $G''$ is obtained at least in the vicinity of room temperature, the interaction between the component (ii) and the component (i), each having a relatively high concentration, is important. The ratio $\beta'/(\beta'+\gamma')$ is more than 0, preferably 0.1 or more, more preferably 0.2 or more, still more preferably 0.4 or more. The upper limit thereof may be 1 or less, and for example, $\gamma'=0$ may be established. Further, it is preferred that the concentration of each solid content of the component (i) and the component (ii) with respect to a solvent be 10 mass % or more.

Such cold gelation characteristics are not considered to be preferred in coating, for example, spray coating because a gelled material causes clogging in a nozzle for a spray and the like. Thus, the nonionic water-soluble cellulose compound and the enteric methacrylic acid copolymer, each having a high concentration and a high viscosity value, are not usually combined selectively (Non-patent Literature 5).

Further, in the present disclosure, it is preferred that a part or an entirety of the component (iii) be substituted with the water-insoluble (meth)acrylic acid alkyl ester copolymer serving as the component (iv) in order to reduce the ratio $\gamma'$ of the component (iii) because the required amount of the enteric polymer, and then the total amount of the basic neutralizer can be further reduced without deteriorating the acid resistance. With a dispersion liquid of the water-insoluble (meth)acrylic acid alkyl ester copolymer, a water dispersion liquid of colloid can be directly produced by an emulsion polymerization process. Thus, it is preferred to use the dispersion liquid of the water-insoluble (meth)acrylic acid alkyl ester copolymer because an organic solvent for solubilization in water is not required to be used.

Even in the case where the enteric cellulose compound and the enteric methacrylic acid copolymer are contained as the enteric polymer, and in an enteric polymer dispersion solution, for example, a basic neutralizer is used in an amount for complete neutralization or in an amount close to complete neutralization in dissolution of the enteric cellulose compound, when a colloid dispersion liquid obtained by emulsion polymerization not requiring neutralization is used as the enteric methacrylic acid copolymer, the usage amount of the basic neutralizer can be significantly reduced with respect to the total amount of the enteric polymer, and a dispersion liquid of fine particles in which a small part of the enteric polymer is neutralized and dissolved (partially neutralized) can be obtained as a whole. The foregoing has also an advantage in that the amount of a residual salt in the capsule film after drying can be reduced without using a volatile basic neutralizer, such as ammonia. In particular, it is preferred that $\beta'/(\beta'+\gamma')$ be 0.2 or more because the degree of neutralization of the entire enteric polymer containing the enteric cellulose compound and the enteric methacrylic acid copolymer can be set to 50% or less. It is more preferred that $\beta'/(\beta'+\gamma')$ be 0.4 or more because the degree of neutralization of the entire enteric polymer can be set to 30% or less.

Further, it is still more preferred that $\gamma'=0$ be established, that is, the enteric polymer be formed of only the enteric methacrylic acid copolymer because the degree of neutralization can be set to 20% or less. However, also in this case, due to the constraint in a method of preparing a capsule-preparing solution described later, the lower limit of the degree of neutralization is preferably 2% or more, more preferably 5% or more. When the component (i) and the component (ii) are directly mixed with each other under a state in which the basic neutralizer is not present in a solvent, the mixture is immediately gelled to cause condensation, and hence points of attention regarding the preparation method as described later are required.

Further, in order to adjust the viscosity of the capsule-preparing solution, at least one kind selected from the group consisting of PVA, a plasticizer, and a surfactant may be added as the component (v) in addition to the component (i), the component (ii), the component (iii), and the component (iv). Alternatively, at least one kind selected from the group consisting of PVA, a plasticizer, and a surfactant may be used for stabilizing the dispersion state of colloid or solid fine particles in the capsule-preparing solution.

When a total mass of the component (i), the component (ii), the component (iii), the component (iv), and the component (v) contained in the enteric hard capsule-preparing solution is set to 100 mass %, and when a ratio of the component (i) is represented by $\alpha'$ mass %, a ratio of the component (ii) is represented by $\beta'$ mass %, a ratio of the component (iii) is represented by $\gamma'$ mass %, a ratio of the component (iv) is represented by $\sigma'$ mass %, and a ratio of the component (v) is represented by $\varphi'$ mass % (the same applies hereinafter), those ratios are substantially equal to the ratios of the components of the hard capsule film obtained by drying the preparing solution. Thus, the component ratios preferred as the capsule film are applied. In this case, the mass of each component refers to a mass of a solid content.

Specifically, the total ratio $(\beta'+\gamma'+\sigma')/(\alpha'+\beta'+\gamma'+\sigma'+\varphi')$ of the enteric polymer (component (ii) and component (iii)) and the component (iv) is preferably 0.5 or more. The value of $(\beta'+\gamma'+\sigma')/(\alpha'+\beta'+\gamma'+\sigma'+\varphi')$ is more preferably 0.55 or more, still more preferably 0.6 or more. Simultaneously, $(\beta'+\gamma')/(\beta'+\gamma'+\sigma')$ is preferably 0.4 or more, more preferably 0.5 or more. With this, the acid resistance sufficient as the enteric hard capsule can be exhibited. Meanwhile, in order to maintain the appropriate hardness and cracking resistance of the capsule film, the upper limit value of $(\beta'+\gamma'+\sigma')/(\alpha'+\beta'+\gamma'+\varphi')$ is set to 0.9, preferably 0.8.

As a more preferred embodiment, there is a composition in which the entire enteric cellulose compound of the component (iii) is formed of the water-insoluble (meth) acrylic acid alkyl ester copolymer serving as the component (iv) in the same manner as in the film components. Specifically, the foregoing is a composition in which, when $\gamma'$ is 0%, $\beta'/(\alpha'+\beta'+\sigma'+\varphi')$ is 0.3 or more, more preferably 0.4 or more. The upper limit value thereof is preferably 0.7 or less, more preferably 0.65 or less.

When $\gamma'$ is 0%, it is preferred that $(\beta'+\gamma'+\sigma')/(\alpha'+\beta'+\gamma'+\sigma'+\varphi')$, that is, $(\beta'+\sigma')/(\alpha'+\beta'+\sigma'+\varphi')$ be set to 0.5 or more and 0.9 or less as described above. Further, it is preferred that $\sigma'/(\alpha'+\beta'+\gamma'+\sigma'+\varphi')$, that is, $\sigma'/(\alpha'+\beta'+\sigma'+\varphi')$ be set to 0.2 or more.

The ratio $\varphi'/(\alpha'+\beta'+\gamma'+\sigma'+\varphi')$ of the component (v) is set to preferably 0.15 or less, more preferably 0.1 or less in any of the above-mentioned cases.

In addition to the component (i), the component (ii), the component (iii), the component (iv), and the component (v), a lubricant, a metal sequestering agent, a colorant, a light-shielding agent, and the like may be contained. When the total mass of the component (i), the component (ii), the component (iii), the component (iv), and the component (v) contained in the film is represented by X', and the total mass of the plasticizer, the lubricant, the metal sequestering agent, the colorant, the light-shielding agent, and the like is represented by $\varepsilon'$, $\varepsilon'/X'$ may be set within a range of 0.2 or less, more preferably 0.1 or less.

In addition, there is no limitation on each of the solid contents of the component (i), the component (ii), the component (iii), the component (iv), and the component (v) contained in the enteric hard capsule-preparing solution as long as the hard capsule-preparing solution can be prepared. When the enteric hard capsule-preparing solution is set to 100 mass %, the total solid content of the component (i), the component (ii), the component (iii), the component (iv), and the component (v) is preferably from 10 mass % to 30 mass %, more preferably from 13 mass % to 25 mass %. In the case where the lubricant, the metal sequestering agent, the colorant, the light-shielding agent, and the like are contained, when the enteric hard capsule-preparing solution is set to 100 mass %, the total of the above-mentioned components is 6 mass % or less, preferably 3 mass % or less, more preferably 2 mass % or less, still more preferably 1 mass % or less.

Dissolved or dispersed solid contents other than the components (i) to (v) are usually present in the capsule film while keeping substantially original component ratios. In addition, moisture in the solvent may partially remain in the film as described above.

A third embodiment according to the present disclosure relates to a method of preparing the enteric hard capsule-preparing solution of the second embodiment.

Specifically, the third embodiment relates to a method of preparing an enteric hard capsule-preparing solution, including mixing a component (i) and a component (ii) with each other under a condition in which a basic neutralizer is present in a solvent. The component (i) is a nonionic water-soluble cellulose compound having a viscosity value within a range of from 100 mPa·s to 100,000 mPa·s, and the component (ii) is an enteric methacrylic acid copolymer. It is preferred that a colloid dispersion liquid be used regarding the enteric methacrylic acid copolymer.

As described above, in order to cause an abrupt increase in viscosity and cold gelation in the vicinity of room temperature in a temperature decrease process, it is important to use the nonionic water-soluble cellulose compound serving as the component (i) having a viscosity value within a range of from 100 mPa·s to 100,000 mPa·s and the enteric methacrylic acid copolymer serving as the component (ii) together. However, when both the components are directly mixed with each other, aggregation immediately occurs, and a stable dispersion liquid may not be obtained. Therefore, it is required to mix both components under a condition in which the basic neutralizer is present in the solvent. For this purpose, when the enteric polymer is formed of only the component (ii), the degree of neutralization with respect to the component (ii) is preferably 2% or more, more preferably 5% or more. The upper limit thereof is 20% or less, more preferably 15% or less. When the upper limit is more than 20%, the cold gelation performance is liable to be impaired.

When the enteric polymer is formed of both the component (ii) and the component (iii), it is difficult to distinguish the respective degrees of neutralization of the component (ii) and the component (iii) from each other. For example, the degree of neutralization with respect to the entire enteric polymer formed of the component (ii) and the component (iii) is preferably 10% or more, more preferably 20% or more. The upper limit thereof is preferably 50% or less, more preferably 30% or less.

The third embodiment is divided into an embodiment (embodiment 3-1) in which the enteric cellulose compound serving as the component (iii) is contained as the enteric polymer and an embodiment (embodiment 3-2) in which the enteric cellulose compound serving as the component (iii) is not contained as the enteric polymer.

The embodiment 3-1 relates to a method of preparing an enteric hard capsule-preparing solution containing film components containing the component (i), the component (ii), and the component (iii) and a solvent. The method includes: a step A of preparing a neutralized solution of the component (iii); a step B of adding the component (i) to the neutralized solution containing the component (iii), to thereby prepare a partially dissolved solution of the component (i); and a step C of mixing a dispersion liquid of the component (ii) with the solution prepared in the step A or the step B.

In each step, each component may be added to the solvent. Alternatively, the component may be added to or mixed with a solution containing another component prepared in the previous step. A transition temperature between the respective steps, or the temperature regulation in mixing of solutions prepared in the respective steps may be appropriately set in accordance with the following requirements.

In the step A, as the neutralized solution of the component (iii), a dissolved neutralized product of the component (iii) may be used. Alternatively, the neutralized solution of the component (iii) may be prepared by dispersing a non-neutralized component (iii) in a solvent and adding a basic neutralizer to the resultant. The step A is preferably a step of preparing a neutralized solution by dispersing a non-neutralized component (iii) in a solvent, adding the above-mentioned basic neutralizer that is pharmaceutically acceptable or is acceptable a food additive to a dispersion liquid, to thereby at least partially neutralize the dispersion liquid, and dissolving the resultant in a solvent.

Specifically, the non-neutralized component (iii) is loaded into a solvent, for example, purified water in an amount of about 5 times the total amount of the entire component excluding the solvent, and the non-neutralized component (iii) is uniformly dispersed so as not to form lumps. After that, the basic neutralizer is loaded into the resultant to dissolve the component (iii). In order to completely neutralize the component (iii), as described above, the basic neutralizer is added thereto so that a cation derived from the basic neutralizer becomes equivalent or more to 1 mol of a carboxyl group contained in the component (iii).

In an enteric cellulose compound that is generally commercially available, a large lump of pulp serving as a starting material is subjected to hydrolysis or chemical decomposition with an enzyme to control its molecular weight, and in addition, the resultant is pulverized by a mechanical procedure, such as mechanical milling, to obtain solid particles of the order of from 10 μm to 100 μm. In order to further miniaturize the solid particles to achieve a particle diameter smaller than about 1 μm or dissolve the solid particles, it is preferred that the degree of neutralization in neutralization of only the component (iii) be 50% or more of an equivalent amount. The state in which the degree of neutralization is not complete neutralization is referred to as "partial neutralization". Specifically, the neutralized solution in the step A has a degree of neutralization of preferably 50% or more, or may be a completely neutralized solution. It is not preferred that the basic neutralizer be contained in an excess amount exceeding an equivalent because a problem such as salt precipitation occurs. It is preferred that the basic neutralizer be contained so that the amount of a cation becomes less than an equivalent amount with respect to 1 mol of a carboxyl group contained in the component (iii).

It is preferred that the pH of the completely neutralized enteric cellulose solution be set to pH in the vicinity of a dissociation point of the enteric cellulose compound. Specifically, the pH of the completely neutralized enteric cellulose solution is preferably from 4.5 to 7.0, more preferably from 5.0 to 6.5 in the vicinity of the dissociation point of the enteric cellulose compound. When the pH is less than 4.5, the enteric cellulose compound may not be dissolved. When the pH is more than 7.0, an excess cation may neutralize also the methacrylic acid copolymer to be added later. For example, in the case of HPMCP, the dissociation point of the enteric cellulose compound corresponds to pH at which a carboxyl group in a carboxybenzoyl group is ionized, and HPMCP is dissolved to neutralize a solution in neutralization titration. In addition, in the case of HPMCAS, the dissociation point of the enteric cellulose compound corresponds to pH at which a carboxyl group in a succinoyl group and an acetyl group is ionized, and HPMCAS is dissolved to neutralize a solution in neutralization titration. The pH in the vicinity of the dissociation point of HPMCP and HPMCAS is from 5 to 7.

Specifically, the step B is a step of preparing a partially dissolved solution by partially dissolving the component (i) in the neutralized solution containing the component (iii) or in a mixed solution of the neutralized solution of the component (iii) and the dispersion liquid of the component (ii). The step of preparing the partially dissolved solution is a step of preparing a dispersion liquid by adding the component (i) to the neutralized solution containing the component (iii) or the mixed solution of the neutralized solution of the component (iii) and the dispersion liquid of the component (ii) at a first temperature T1 equal to or higher than a cloud point T0 of the component (i) and partially dissolving the component (i) at the second temperature T2 lower than the cloud point.

In the embodiment 3-1, there is no limitation on the first temperature T1 as long as the first temperature T1 is a temperature equal to or higher than the cloud point T0 and less than the boiling point of the solvent. The first temperature T1 may be set, for example, within a range of from 60° C. to 90° C. When the nonionic water-soluble cellulose compound is HPMC or MC, the temperature T1 may be set, preferably, within a range of from 70° C. to 90° C. When the nonionic water-soluble cellulose compound is HPC, the temperature T1 is preferably within a range of from 60° C. to 80° C. The reason for dispersing the nonionic water-soluble cellulose compound at a temperature equal to or higher than the cloud point is to prevent formation of lumps before the nonionic water-soluble cellulose compound is uniformly dispersed.

In the embodiment 3-1, it is preferred that the second temperature T2 be higher than room temperature (20° C. to 25° C.) and lower than the cloud point T0. For example, it is preferred that the second temperature T2 be set within a range of from 30° C. to 60° C. When the nonionic water-soluble cellulose compound is HPMC or MC, the temperature T2 may be set within a range of from 30° C. to 60° C. When the nonionic water-soluble cellulose compound is HPC, the temperature T2 is preferably within a range of from 30° C. to 40° C.

In the embodiment 3-1, the viscosity of a dispersion liquid in which the nonionic water-soluble cellulose compound is dispersed in an undissolved state at a temperature equal to or higher than T0 is significantly low and less than about 100 mPa·s. When the dissolution of the nonionic water-soluble cellulose compound starts, the viscosity is gradually increased to reach a viscosity of more than 100 mPa·s, and hence it is found that the nonionic water-soluble cellulose compound passes through T0 in the temperature decrease process. A dispersion liquid in which solid particles of the undissolved water-soluble cellulose are stably present is obtained within a temperature of from about T0 to about 10° C. When the temperature is further decreased, an abrupt increase in viscosity by 1 or 2 orders of magnitude is continued to reach 1,000 mPa·s or more. Further, when the temperature approaches the vicinity of room temperature, the solid particles of the water-soluble cellulose compound are substantially entirely dissolved while substantially maintaining a high viscosity. Then, the nonionic water-soluble cellulose compound is substantially completely dissolved in the solvent, and the sea-island structure of the capsule film cannot be kept. In addition, the viscosity as the capsule-preparing solution becomes too high, and hence it is preferred that the temperature T2 be equal to or lower than T0 and be not lower than T4. Specifically, the temperature T2 is set preferably so as not to be lower than 30°, and is more preferably set to 35° C. or more. In addition, T2 is preferably 60° C. or less, more preferably 55° C. or less.

As described above, a dispersion liquid in which the component (i) is partially dissolved may be prepared by suspending the nonionic water-soluble cellulose compound serving as the component (i) in the neutralized solution of the component (iii) at the temperature T1 equal to or higher than the cloud point T0 and decreasing the temperature to the second temperature T2.

In the preparing solution according to the present disclosure and a preparation step C of the preparing solution according to the present disclosure, the methacrylic acid copolymer serving as the component (ii) is mixed with the neutralized solution containing the enteric cellulose compound as a water dispersion liquid. Therefore, the entire enteric polymer containing a combination of the enteric cellulose compound and the methacrylic acid copolymer may be set in a partially neutralized state. Thus, when the component (i) and the component (ii) are mixed with each other, it is preferred that the basic neutralizer be present in the solvent in advance. The KOH equivalent of the methacrylic acid copolymer, in particular, L30D55 is significantly large, i.e., 301.2 mg/g. Therefore, even in the case where the enteric cellulose compound is completely neutralized in the step A, when the methacrylic acid copolymer is appropriately contained, the degree of neutralization of the combination of the enteric cellulose compound and methacrylic acid copolymer with respect to the entire enteric base may be set to 50% or less, further 30% or less. The foregoing is effective for suppressing the dissolution of the capsule film in an intermediate region of from pH 4 to pH 5 in a dissolution test.

The embodiment 3-1 may include a step D of mixing the solution prepared in the step A, B, or C and the water-insoluble (meth)acrylic acid alkyl ester copolymer serving as the component (iv) with each other. Further, the embodiment 3-1 may further include a step E of holding the solution obtained in the step B, C, or D at the third temperature T3 lower than the cloud point of the component (i). In addition, it is preferred that the third temperature T3 be equal to or higher than T2 and lower than the cloud point T0, but be not lower than the cloud point by 10° C. or more. The case in which T2=T3 is established is possible. With this, the partially dissolved state of the component (i) can be stably kept. For example, the third temperature T3 may be set within a range of from 30° C. to 65° C. When the nonionic water-soluble cellulose compound is HPMC, in particular, HPMC of substitution types 2910 and 2906, the temperature T3 may be set within a range of from 40° C. to 65° C. The temperature T3 may be set preferably within a range of from 45° C. to 60° C., more preferably within a range of from 50° C. to 60° C. With this, a temperature difference of about 10° C. or more can be ensured between the temperature T3 and the temperature T4 at which an abrupt increase in viscosity caused by cold gelation starts. Thus, the foregoing is preferred from the viewpoint of stably keeping the preparing solution. When the nonionic water-soluble cellulose compound is MC or HPC, the temperature T3 is set preferably within a range of from 30° C. to 50° C.

The embodiment 3-1 according to the present disclosure further includes two embodiments: an embodiment 3-1a and an embodiment 3-1b.

(1) The embodiment 3-1a relates to a method of preparing an enteric hard capsule-preparing solution containing film components containing a component (i), a component (ii) and a component (iii) and a solvent. The method includes: a step a1 of preparing a neutralized solution of the component (iii); a step b1 of partially dissolving the component (i) in the neutralized solution of the component (iii); and a step c1 of mixing a dispersion liquid of the component (ii) and the solution obtained in the step b1 with each other.

The descriptions of the neutralized solution of the component (iii), the cloud point T0, the temperature T1, the temperature T2, and the temperature T3 in the embodiment 3-1 are incorporated herein.

The step a1 is a step of preparing the neutralized solution of the component (iii), and the step a1 conforms to the step A in the third embodiment.

In the step b1, a dispersion liquid is prepared by dispersing the component (i) in a liquid prepared in the step a1 at the first temperature T1 equal to or higher than the cloud point T0 and decreasing the temperature to partially dissolve the component (i) at the second temperature T2 lower than the cloud point. Specifically, a dispersion liquid in which the component (i) is partially dissolved may be prepared by dispersing the component (i) in the liquid prepared in the step a1 at a temperature equal to or higher than the cloud point T0, and decreasing the temperature to the second temperature T2.

In the step c1, the partially dissolved solution of the component (i) containing the component (iii) obtained in the step b1 and the dispersion liquid of the component (ii) are mixed with each other. There is no limitation on the mixing method as long as the neutralized solution of the component (iii) and the dispersion liquid of the component (ii) can be mixed with each other.

In addition, this embodiment may further include, after the step c1, a step d1 of mixing the solution prepared in the step c1 and a water-insoluble (meth)alkyl ester copolymer with each other, and further a step e1 of holding, after the step b1, c1, or d1, the solution at the third temperature T3 lower than the cloud point of the component (i).

(2) The embodiment 3-1b relates to a method of preparing an enteric hard capsule-preparing solution containing film components containing a component (i), a component (ii), and a component (iii) and a solvent. The method includes: a step a2 of preparing a neutralized solution of the component (iii); a step c2 of mixing the neutralized solution of the component (iii) and the dispersion liquid of the component (ii) with each other; and a step b2 of partially dissolving the component (i) in the solution obtained in the step c2.

The descriptions of the neutralized solution of the component (ii), the cloud point T0, the temperature T1, the temperature T2, and the temperature T3 in the embodiment 3-1 are incorporated herein.

The step a2 is a step of preparing the neutralized solution of the component (iii), and the step a2 conforms to the step A in the third embodiment.

In the step c2, the neutralized solution of the component (iii) and the dispersion liquid of the component (ii) are mixed with each other. There is no limitation on the mixing method as long as the neutralized solution of the component (iii) and the dispersion liquid of the component (ii) may be mixed with each other.

In the step b2, a dispersion liquid is prepared by dispersing the component (i) in a liquid prepared in the step c2 at the first temperature T1 equal to or higher than the cloud point T0 and decreasing the temperature to partially dissolve the component (i) at the second temperature T2 lower than the cloud point. Specifically, a dispersion liquid in which the component (i) is partially dissolved may be prepared by suspending the component (i) in the liquid prepared in the step c2 at a temperature equal to or higher than the cloud point T0, and decreasing the temperature to the second temperature T2.

In addition, this embodiment may further include, after the step b2, a step d2 of adding a dispersion liquid of a water-insoluble (meth)alkyl ester copolymer to the solution obtained in the step b2, and further a step e2 of holding, after the step b2, c2, or d2, the solution at the third temperature T3 lower than the cloud point of the component (i). It is preferred to add at least one kind selected from the group consisting of polyvinyl alcohol, a plasticizer, and a surfactant, which serves as the component (v), in a process after an increase in solution temperature to the temperature T1 in the step B until the solution is held at the temperature T3 in the step E.

The embodiment 3-2 according to the present disclosure relates to a method of preparing an enteric hard capsule-preparing solution containing film components containing a component (i), a component (ii), and a component (iv) and a solvent. The method includes: a step A' of preparing a partially neutralized solution of the component (ii); a step B' of preparing a partially dissolved solution of the component (i); and a step C' of mixing a dispersion liquid of the component (iv) and the solution prepared in the step A' or B' with each other. The above-mentioned method of preparing a capsule-preparing solution is suitable, in particular, for the case in which γ'=0 is established, that is, the case in which the enteric polymer is formed of only the enteric methacrylic acid copolymer.

The component (iv) is a dispersion liquid of a water-insoluble (meth)acrylic acid alkyl ester copolymer.

In the following, the descriptions of the cloud point T0, the temperature T1, the temperature T2, and the temperature T3 in the embodiment 3-1 are incorporated herein.

Regarding the methacrylic acid copolymer serving as the component (ii), it is originally preferred to use a colloid dispersion liquid enabling an additional dispersion step through neutralization to be omitted. However, in order to prevent undesirable aggregation and deposition caused by mixing with the component (i) or the partially dissolved dispersion liquid of the component (i), to thereby stabilize the dispersion state of the capsule-preparing solution, it is desired to perform mixing with the component (i) in the presence of a minimum amount of the basic neutralizer.

Therefore, in the step A', the partially neutralized solution of the component (ii) is prepared by adding the basic neutralizer that is pharmaceutically acceptable or is acceptable as a food additive to the component (ii) in advance, and the degree of neutralization thereof is set to be relatively low, preferably from 2% to 20%, more preferably from 5% to 15%. After that, in the step B', a partially dissolved solution is prepared by adding the component (i) to the solution containing the basic neutralizer and the component (ii), to thereby partially dissolve the component (i). The step B' is a step of preparing a dispersion liquid by adding the component (i) to the neutralized solution containing the component (ii) or a mixed solution of the neutralized solution of the component (ii) and the dispersion liquid of the component (iv) at the first temperature T1 equal to or higher than the cloud point T0 of the component (i) and partially dissolving the component (i) at the second temperature T2 lower than the cloud point.

Further, the embodiment 3-2 may further include a step E' of holding the solution obtained in the step B' or C' at the third temperature T3 lower than the cloud point of the component (i). In addition, it is preferred that the third temperature T3 be higher than T2 and be not lower than the cloud point T0 by 10° C. or more. With this, the partially dissolved state of the component (i) can be stably kept. For example, the third temperature T3 may be set within a range of from 30° C. to 65° C. When the nonionic water-soluble cellulose compound is HPMC, in particular, HPMC of substitution types 2910 and 2906, the temperature T3 may be set within a range of from 40° C. to 65° C. The temperature T3 may be set preferably within a range of from 45° C. to 60° C., more preferably within a range of from 50° C. to 60° C. With this, a temperature difference of about 10° C. or more can be ensured between the temperature T3 and the temperature T4 at which an abrupt increase in viscosity caused by cold gelation starts. Thus, the foregoing is preferred from the viewpoint of stably keeping the preparing solution. When the nonionic water-soluble cellulose compound is MC or HPC, the temperature T3 may be set preferably within a range of from 30° C. to 40° C.

In the preparing solution according to the present disclosure and a preparation step C' of the preparing solution according to the present disclosure, the (meth)acrylic acid alkyl ester copolymer serving as the component (iv) hardly interacts with any of the component (i) and the component (ii), and may be added as a water dispersion liquid subsequently after any one of the step A' and the step B' or after each of the steps in a divided manner. This embodiment may further include, after the step C', a step E' of holding the solution obtained in the step C' at the third temperature T3 lower than the cloud point of the component (i).

It is preferred to add at least one kind selected from the group consisting of polyvinyl alcohol, a plasticizer, and a surfactant, which serves as the component (v), in a process after an increase in solution temperature to the temperature T1 in the step B' until the solution is held at the temperature T3 in the step E'.

Further, in all the steps of preparation in the third embodiment, it is desired to continuously perform stirring. For example, when a preparation step is performed through use of a cylindrical container, it is preferred that stirring be performed by rotating a propeller-like stirring blade at 1 rpm to hundreds of rpm.

4. Method of Preparing Enteric Hard Capsule

A fourth embodiment according to the present disclosure relates to a method of preparing an enteric hard capsule. According to the present disclosure, an enteric hard capsule can be prepared through use of another capsule preparation machine configured to prepare a hard capsule. The enteric hard capsule according to the present disclosure has a feature of being formed by an immersion method, in particular, "cold pin immersion method". The "cold pin immersion method" has a feature in that the surface temperature of a molding pin at a time of immersion is lower than the temperature of a capsule-preparing solution.

There is no particular limitation on a method of preparing (molding) an enteric hard capsule as long as the method includes a step of preparing a capsule through use of the enteric hard capsule-preparing solution according to the present disclosure. In general, regarding an enteric hard capsule, a mold pin (pin for molding a capsule) serving as a mold for a capsule is immersed in an enteric hard capsule-preparing solution, and a film adhering to the mold pin when the mold pin is pulled up is cured and dried, to thereby obtain a desired capsule shape and thickness (dipping method). Specifically, the method of preparing an enteric hard capsule includes a step of preparing an enteric hard capsule-preparing solution by the above-mentioned method or preparing an enteric hard capsule-preparing solution, for example, through purchase thereof and a preparation step of immersing a mold pin in the enteric hard capsule-preparing solution, pulling up the mold pin, inverting the mold pin upside down, and drying the solution adhering to the mold pin.

More specifically, the enteric hard capsule to be used in the present disclosure may be produced through the following molding steps:

(1) a step of immersing a mold pin in an enteric hard capsule-preparing solution (immersion step);

(2) a step of pulling up the mold pin from the enteric hard capsule-preparing solution (immersion liquid) and drying the enteric hard capsule-preparing solution adhering to an outer surface of the mold pin (drying step); and (3) a step of removing the dried capsule film (film) from the pin for molding a capsule (removal step).

In this case, the enteric hard capsule-preparing solution is held at a temperature T5 that is lower than the cloud point of the nonionic water-soluble cellulose compound and higher than room temperature (20° C. to 25° C.) when the mold pin is immersed. The temperature T5 is preferably a temperature that is not lower than the cloud point T0 by 10° C. or more, more preferably a temperature higher than T2. The temperatures T3 and T5 may also be set to be the same. With this, the partially dissolved state of the component (i) can be stably kept. For example, when the water-soluble cellulose compound is HPMC or MC, T5 is set preferably within a range of from 30° C. to 65° C., more preferably within a range of from 35° C. to 60° C., still more preferably within a range of from 40° C. to 60° C. When the nonionic water-soluble cellulose compound is HPC, the temperature T5 is preferably within a range of from 30° C. to 40° C.

The viscosity of the capsule-preparing solution at a time of immersion at the retention temperature T5 thereof is preferably 100 mPa·s or more, more preferably 500 mPa·s or more, still more preferably 1,000 mPa·S or more.

In addition, the viscosity of the capsule-preparing solution at a time of immersion at the retention temperature T5 is preferably 10,000 mPa·s or less, more preferably 5,000 mPa·s or less, still more preferably 3,000 mPa·S or less.

The viscosity of the capsule-preparing solution may be measured through use of a single cylinder-type rotational viscometer (Brookfield type viscometer, B-type viscometer). For example, the viscosity may be measured as described below. A capsule-preparing solution (liquid amount: 600 ml) is prepared in a 1 L beaker. M3 rotor (measurement range: 0 mPa·s to 10,000 mPa·s) is placed in the capsule-preparing solution maintained at T5, and the viscosity is measured at a rotor rotation number of 12 r.p.m. for a measurement time of 50 seconds.

In contrast, it is preferred that a surface temperature T6 of the mold pin at a time of immersion be lower than the liquid temperature T5 of the enteric hard capsule-preparing solution and further be lower than the temperature T4 at which an abrupt increase in viscosity caused by cold gelation occurs. The surface temperature T6 is, for example, within a range of from 20° C. to 30° C., more preferably within a range of from 20° C. to 28° C.

There is no particular limitation on the drying step (2), and drying may be performed at room temperature (20° C. to 30° C.). Usually, drying is performed by blowing in air at room temperature.

The capsule film prepared as described above is cut to be adjusted to a predetermined length and can be provided as an enteric hard capsule under a state in which a body portion and a cap portion are fitted with each other as a pair or a state in which the body portion and the cap portion are not fitted with each other.

The film thickness of the enteric hard capsule is usually set within a range of from 50 μm to 250 μm. In particular, the thickness of a side wall portion of the capsule is usually from 75 μm to 150 μm, more preferably from 80 μm to 120 μm in the case of a capsule that is currently commercially available. As the size of the enteric hard capsule, there are given No. 00, No. 0, No. 1, No. 2, No. 3, No. 4, No. 5, and the like. In the present disclosure, an enteric hard capsule of any size may be prepared.

5. Enteric Hard Capsule Formulation

A filling material, such as a common food, a food with health claims (a food with function claims, a food with nutrient function claims, or a food for specified health use), a quasi-drug, or a pharmaceutical, may be filled into the enteric hard capsule according to the present disclosure. Examples of the filling material may include: active ingredients, such as ingredients derived from plants (including a green unicellular alga) (e.g., raw plants, partially dried microorganisms, completely dried plants, plant processed products, and plant extracts), microorganisms (e.g., bacteria, yeast, and *Euglena*) or ingredients derived from the microorganisms (e.g., raw microorganisms, partially dried microorganisms, completely dried microorganisms, microorganism processed products, and microorganism extracts), nutritional fortification healthcare agents, antipyretic, analgesic, and anti-inflammatory agents, psychotropic agents, anxiolytic agents, antidepressants, hypnosedatives, anticonvulsive agents, central nervous effect agents, brain metabolism-improving agents, brain circulation-improving agents, antiepileptic agents, sympathomimetic stimulants, gastrointestinal agents, antacids, anti-ulcer agents, antitussive and expectorant agents, antiemetic agents, anapnoics, bronchodilators, anti-allergic agents, agents for dental and oral use, antihistamines, cardiotonic agents, agents for arrhythmia, diuretic agents, hypotensive agents, vasoconstrictive agents, coronary vasodilators, peripheral vasodilators, agents for hyperlipidemia, cholagogues, antibiotics, chemotherapeutic agents, agents for diabetes, agents for osteoporosis, antirheumatic agents, skeletal muscle relaxants, spasmolytic agents, hormonal agents, alkaloidal narcotics, sulfa drugs, arthrifuges, blood anticoagulants, and antineoplastic agents; and compositions containing the active ingredients. There is no particular limitation on those filling materials, and there may be widely given known filling materials. Those ingredients may be used alone or as a compound drug with another compound. The filling material may have any form such as a solid, a powder, a granule, a pulverized product, a liquid, and a gel. In addition, those ingredients are each filled into a capsule in a predetermined known appropriate amount in accordance with the condition, age, and the like of a target for administration Examples of the nutritional fortification healthcare agents include: vitamins, such as vitamin A, vitamin D, vitamin E (e.g., d-α-tocopherol acetate), vitamin B1 (e.g., dibenzoyl thiamine or fursultiamine hydrochloride), vitamin B2 (e.g., riboflavin butyrate), vitamin B6 (e.g., pyridoxine hydrochloride), vitamin C (e.g., ascorbic acid and sodium L-ascorbate), and vitamin B12 (e.g., hydroxocobalamin acetate or cyanocobalamin); minerals, such as calcium, magnesium, and iron; proteins; amino acids; oligosaccharides; and crude drugs.

Examples of the antipyretic, analgesic, and anti-inflammatory agents include, but not limited to, aspirin, acetaminophen, ethenzamide, ibuprofen, diphenhydramine hydrochloride, chlorpheniramine dl-maleate, dihydrocodeine phosphate, noscapine, methylephedrine hydrochloride, phenylpropanolamine hydrochloride, caffeine, caffeine anhydride, serrapeptase, lysozyme chloride, tolfenamic acid, mefenamic acid, diclofenac sodium, flufenamic acid, salicylamide, aminopyrine, ketoprofen, indomethacin, bucolome, and pentazocine.

In particular, the application of the enteric hard capsule is highly useful when there is a risk in that a capsule is dissolved in the stomach to cause a side effect on the stomach or when a capsule is required to be absorbed in the intestines without being dissolved in the stomach because the capsule is unstable to an acid. Specifically, regarding a formulation in which the efficacy of an active ingredient may be deteriorated with gastric acid, the enteric hard capsule formulation according to the present disclosure can protect the active ingredient from a gastric acid and cause the active ingredient to effectively pass through the stomach to be delivered to the intestines. Thus, the enteric hard capsule formulation according to the present disclosure is particularly useful.

For example, it has been known that aspirin administered in a large amount in the form of uncoated granules has a side effect causing a gastric ulcer-like symptom, and hence aspirin is one of typical drugs to which the enteric hard capsule is desired to be applied.

Meanwhile, examples of the medicinal ingredients unstable to an acid include omeprazole, lansoprazole, rabeprazole sodium, and esomeprazole magnesium hydrate, each known as a proton-pump inhibitor (PPI). The PPI reaches a parietal cell through the blood, and is brought into contact with a hydrogen ion at a high concentration in the secretory canaliculus of the parietal cell to be activated. However, the PPI is an agent that is significantly unstable under an acidic environment, and hence cannot exhibit a sufficient effect when being exposed to an acid before reaching the parietal cell. Therefore, in order for the PPI to exhibit a strong effect of suppressing acid secretion, the PPI is usually formed into an enteric formulation.

Duloxetine that is one of antidepressant drugs called serotonin noradrenaline reuptake inhibitors is also weak to an acid, and hence is an exemplary active pharmaceutical ingredient that is desired to be formed into an enteric formulation.

As the common food, the food with health claims (the food with function claims, the food with nutrient function claims, or the food for specified health use), fucoidan, heme iron, polyphenols, peptides, amino acids (e.g., royal jelly, ornithine, citrulline, aminolevulinic acid, black vinegar, or methionine, valine, leucine, or isoleucine serving as a hydrophobic amino acid), proteins (e.g., a milk protein, such as lactoferrin, collagen, and placenta), glycoproteins, enzyme-fermented foods (e.g., nattokinase), coenzymes (e.g., coenzyme Q10), vitamins (e.g., β-carotene), minerals, viable microorganisms (e.g., *Euglena, Chlorella*, yeast, *Lactobacillus*, and *Bifidobacterium*), plant extracts (e.g., crude drugs and herbs, such as turmeric extract, carrot extract, Japanese plum extract, ginkgo leaf extract, blueberry extract, and *Rubus suavissimus* extract), and natural organic substances, such as propolis, or any combination thereof, but not limited thereto, may be filled into the enteric hard capsule according to the present disclosure.

The filling of such content into the enteric hard capsule may be performed with a known capsule filling machine, such as a fully automatic capsule filling machine (model name: LIQFIL super 80/150, manufactured by Qualicaps Co., Ltd.) or a capsule filling and sealing machine (model name: LIQFIL super FS, manufactured by Qualicaps Co., Ltd.). A body portion and a cap portion of the hard capsule obtained as described above are joined to each other by covering the body portion with the cap portion to fit the body portion and the cap portion with each other after a content is filled into the body portion. Then, the filled capsule may be made tamper-resistant through use of an appropriate technology of permanently sealing a joint line, as required. Typically, a sealing or banding (hereinafter referred to as "sealing") technology may be used, and herein, those technologies are well known to a person skilled in the art of a capsule. As a specific example, a sealing agent (hereinafter sometimes referred to as "seal-preparing solution") of a polymer solution is applied to the surface of the body portion and the surface of the cap portion at a constant width with an end edge portion of the cap portion being the center in a circumferential direction of the body portion and the cap portion once or a plurality of times, preferably once or twice. With this, the fitted portion may be sealed to obtain an enteric hard capsule formulation. As the polymer solution, a diluted aqueous solution of an enteric polymer to be used in a capsule film or a solution in which the enteric polymer is dissolved in a water/ethanol or water/isopropanol solvent may be used. In addition, when the diluted aqueous solution or the solution in which the enteric polymer is dissolved in a water/ethanol or water/isopropanol solvent is used, those solutions may also be used under a state in which the enteric polymer is partially neutralized and dissolved with the basic neutralizer as described above.

It is preferred that the polymer contained in the seal-preparing solution be formed of the same enteric polymer or nonionic water-soluble cellulose compound as that contained in the enteric hard capsule film to which the seal is applied. With this, the adhesiveness with the capsule film is excellent, and unnecessary additive components are prevented from being contained in the capsule formulation. In addition, in this case, the viscosity value of the nonionic water-soluble cellulose compound may be 100 mPa·s.

At a time of capsule sealing, the seal-preparing solution may be used generally at room temperature or under heating. From the viewpoint of preventing liquid leakage of the hard capsule, it is desired to use the seal-preparing solution within a temperature range of preferably from about 23° C. to about 45° C., more preferably from about 23° C. to about 35° C., most preferably from about 25° C. to about 35° C. The temperature of the seal-preparing solution may be regulated by a method known per se, such as a panel heater or a hot-water heater. For example, it is preferred to regulate the temperature with a circulating hot-water heater or a seal-pan unit of the above-mentioned integrated capsule filling sealing machine which is remodeled into a circulating hot-water heater type because the temperature width can be minutely regulated.

The enteric hard capsule formation according to the present disclosure thus obtained is designed so as to exhibit acid resistance in the stomach, and to be mainly transferred to the intestines to release its content through the dissolution of the capsule film when being administered and ingested into the body of a human or an animal. Therefore, the enteric hard capsule formulation according to the present disclosure is preferred as a formulation filled with a pharmaceutical or food that is not desired to be released in the stomach.

In the present disclosure, in order to enhance the enteric function, impart a further drug delivery control function, or control permeability of a gas and moisture, the capsule film may be coated from outside with additional one or more polymer layers.

Unless otherwise stated, a functional polymer layer means a layer containing a functional polymer that imparts specific mechanical or chemical characteristics to a coated capsule film. The functional polymer is, for example, an enteric polymer and/or a colon-release polymer that has hitherto been used for coating a pharmaceutical solid dosage form (that is, a polymer used for disintegrating a coated dosage form in the colon region of a test subject).

6. Hard Capsule Formulation

As a novel application example using the enteric hard capsule according to the present disclosure, there is given a hard capsule formulation having a feature in that the enteric hard capsule according to the present disclosure is contained in a hard capsule dissolvable under an acidic condition. As the hard capsule dissolvable under an acidic condition, there are given a gelatin capsule and a hypromellose capsule, or a pullulan capsule, but the present invention is not limited thereto. In particular, in the case of a hypromellose hard capsule, those containing water-soluble cellulose having a labeled viscosity (viscosity grade) value of from 3 mPa·s to 15 mPa·s have been used (JP 08-208458 A, JP 2001-506692 A, JP 2010-270039 A, and JP 2011-500871 A). In those, water-soluble cellulose, in particular, HPMC accounts for substantially 100% in a film (containing about 0 mass % to about 5 mass % of a gelling agent, a gelling aid, a light-shielding agent, a colorant, and the like, and about 0 mass % to about 10 mass % of residual moisture in some cases). An active ingredient B is filled into the enteric hard capsule according to the present disclosure in advance, and a medicinal ingredient A and the filled enteric hard capsule are filled into a hard capsule dissolvable under an acidic condition. Such double-capsule formulation enables the delivery of selective and different medicinal ingredients to a plurality of sites in such a manner as to release the active ingredient A in the stomach and then release a medicinal ingredient B after reaching the intestines. As the active ingredient A and the active ingredient B, there may be given the active ingredients described in the above-mentioned section 5.

EXAMPLES

I. Materials to be Used

Materials to be used in Examples, Reference Examples, and Comparative Examples are as described below.

1. Nonionic Water-Soluble Cellulose Compound

As methylcellulose (MC) and hydroxypropyl methylcellulose (HPMC), METOLOSE (trademark) series or TC-5 (trademark) series manufactured by Shin-Etsu Chemical Co., Ltd. were used, and as hydroxypropyl cellulose (HPC), NISSO HPC series manufactured by Nippon Soda Co., Ltd. were used. Specific product names, substitution types, and "viscosity values" (labeled viscosities or viscosity grades) are as shown in Table 2.

TABLE 2

| | Product name | Substitution type | Labeled viscosity (mPa · s) | Representation in the following examples (in conformity with product number represented by the manufacturer) |
|---|---|---|---|---|
| MC | SM | — | 25 | SM** |
| | | | 100 | **is labeled |
| | | | 4,000 | viscosity |
| HPMC | 60SH | 2910 | 50 | 60SH** |
| | | | 4,000 | **is labeled |
| | | | 10,000 | viscosity |
| HPMC | 65SH | 2906 | 50 | 65SH** |
| | | | 400 | **is labeled |
| | | | 1,500 | viscosity |
| | | | 4,000 | |
| HPMC | 90SH | 2208 | 100 | 90SH**SR |
| | | | 4,000 | **is labeled |
| | | | | viscosity |
| HPMC | TC-5 | 2910 | 4.5 | M, R, and S |
| | | | 6 | correspond to |
| | | | 15 | labeled viscosities of 4.5, 6, and 15, respectively |
| HPC | HPC H | — | 1,000 to 4,000 | HPC-H |

2. Enteric Polymer (1) Hydroxypropyl Cellulose Phthalate (HPMCP)

Hydroxypropyl cellulose phthalate sold under the trade name HP50 grade (hereinafter represented as "HP50") of HPMCP (trademark) series manufactured by Shin-Etsu Chemical Co., Ltd. was used.

(2) Hydroxypropyl Methylcellulose Acetate Succinate (HPMCAS)

MF or MG grade (hereinafter represented as "HPMCAS-MF") of AQOAT (trademark) series manufactured by Shin-Etsu Chemical Co., Ltd. was used as hydroxypropyl methylcellulose acetate succinate.

In neutralization of each of those non-salified enteric cellulose compounds with a basic neutralizer, a substantially complete neutralization state was obtained through use of a center value within a NaOH equivalent range recommended by the manufacturer. The amount of the basic neutralizer for complete neutralization was set within an error range of less than 100±1% with respect to the equivalent. The pH of the solution in this case was from about 5 to about 7.

Specifically, the equivalent of the basic neutralizer was 0.065 g/g for HP50, 0.048 g/g for HMPCAS-MF or HMP-CAS-MG, 0.215 g/g for L30D55, and 0.0404 g/g for FS30D. In particular, HP50, which had a relatively large particle diameter and thus provided a rough film, was used by being completely neutralized to the extent possible. Meanwhile, HPMCAS-MF, which had a relatively small particle diameter, provided a substantially transparent solution when the degree of neutralization was 50% or more, more preferably 80% or more.

In addition, the neutralization equivalent of ammonia is 0.0274 g/g for HP50, 0.0202 g/g for HMPCAS-MF or HMPCAS-MG, 0.0914 g/g for L30D55, and 0.0172 g/g for FS30D. In the case of ammonia, volatilization occurs in processes of preparing a preparing-solution and a capsule, and hence ammonia was added in excess of the equivalent.

(3) Methacrylic Acid Copolymer

L30D55 and FS30D of EUDRAGIT (trademark) series manufactured by Evonik Industries AG were used as a methacrylic acid copolymer. L30D55 and FS30D are each a water dispersion liquid having a solid content of 30 mass %. In addition, L10055 obtained by drying and finely powdering L30D55 was dispersed in purified water and stirred, and after that, NaOH (10% aqueous solution) was added thereto so that a predetermined degree of neutralization was achieved. With this, a water dispersion liquid including particles that were slightly coarser than colloid particles of L30D55 but formed into fine particles was obtained.

(4) (Meth) acrylic Acid Alkyl Ester Copolymer

NE30D of Eudragit (trademark) series manufactured by Evonik Industries AG was used as a (meth) acrylic acid alkyl ester copolymer. NE30D was provided as a water dispersion liquid having a solid content of 30 mass %.

3. Polyvinyl Alcohol and Plasticizer

EG48P of GOHSENOL (trademark) series manufactured by The Nippon Synthetic Chemical Industry Co., Ltd. was used as a polyvinyl alcohol and plasticizer. The degree of saponification thereof is from 86.5% to 89.0%, and an estimated degree of polymerization thereof is 2,500. PEG35000 (polyethylene glycol) was purchased from Sigma-Aldrich. PG (propylene glycol) was purchased from Wako Pure Chemical Corporation.

4. Others

Sodium hydroxide (granular, special grade chemical) and ammonia water (28%, special grade chemical) were purchased from Wako Pure Chemical Corporation. Titanium oxide (TIPAQUE A100) was purchased from Ishihara Sangyo Kaisha, Ltd.

II. Measurement and Test Method

1. Dissolution Test of Capsule

In the present disclosure, in principle, a dissolution test specified in the Japanese Pharmacopoeia, Revised Seventeenth Edition was applied. However, the Japanese Pharmacopoeia does not specify the solubility of an empty hard capsule itself, and hence the solubility (dissolution characteristics) of a capsule itself was evaluated by evaluating dissolution of fast-dissolving acetaminophen. 40 mg of acetaminophen, 140 mg of lactose, and 20 mg of sodium starch glycolate (hereinafter referred to as "acetaminophen mixed powder") were filled into one capsule, and the obtained enteric hard capsule formulation was tested in accordance with a dissolution test method (the Japanese Pharmacopoeia, Seventeenth Edition, 6.10-1.2 Paddle Method (paddle revolution number: 50 revolutions/min), with a sinker corresponding to FIG. 6.10-2a being used) specified in the Japanese Pharmacopoeia, to thereby measure a change over time of a dissolution rate of acetaminophen. A bath-type dissolution tester Model 2100 manufactured by Distek Ltd. was used for the dissolution test. The absorbance at 244 nm when the same volume of acetaminophen was separately dissolved in an entire amount in the solution in the dissolution tester bath was set to 100%, and a dissolution rate was determined based on the absorbance at 244 nm in the solution in the dissolution tester bath, which increased in association with dissolution of acetaminophen from the capsule. The sample size "n" were set to from 1 to 6. Herein, as a first liquid and a second liquid, the following aqueous solutions were used. In any of the cases, the temperature of the solution in the bath was set to 37° C.

The first liquid: 7.0 mL of hydrochloric acid and water were added to be dissolved in 2.0 g of sodium chloride, to thereby obtain 1,000 mL of a solution (pH: about 1.2, hereinafter sometimes referred to as "acidic solution").

Second liquid: 3.40 g of potassium dihydrogen phosphate and 3.55 g of anhydrous disodium hydrogen phosphate were dissolved in water to obtain 1,000 mL of a phosphate buffer, and 1 volume of water was added to 1 volume of the phosphate buffer (pH: about 6.8, hereinafter sometimes referred to as "neutral solution").

2. Measurement of Dynamic Viscoelasticity of Capsule-Preparing Solution

The dynamic viscoelasticity of a capsule-preparing solution was measured with a rheometer (MCR102) manufactured by AntonPaar Ltd. For measurement, a double cylindrical tube measurement jig (model No. CC27/T200/SS) and a temperature control system C-PTD200 were used. The liquid amount was set to about 19 mL. In addition, in order to prevent evaporation of water during measurement, about 1 mL of cotton seed oil was dropped onto the outermost surface of the sample liquid in the cylindrical tube. The temperature dependency was measured by decreasing a temperature from 60° C. to 20° C. at 1° C./min, and simultaneously, linearly decreasing an oscillation angle of strain from 1% to 0.1%. The angular frequency ω (rad/sec) is 2 n/sec. As the dynamic viscoelasticity, a storage elastic modulus $G'$ (Pa), a loss elastic modulus $G''$ (Pa), a complex viscosity $|\eta^*|=|G^*|/\omega=\sqrt{(G'^2+G''^2)}/\omega$ (Pa·s), and a viscosity $\eta''=G''/\omega$ (Pa·s) were measured.

3. Viscosity of Capsule-Preparing Solution

The viscosity of a capsule-preparing solution (55° C.) was measured with a Brookfield type viscometer (TVB-10M (Toki Sangyo Co., Ltd.)). For measurement, M3 rotor (measurement range: 0 mPa·s to 10,000 mPa·s) was used. A capsule-preparing solution was prepared (liquid amount: 600 ml) in a 1 L beaker at a rotor rotation number of 12 r.p.m., and after that, the rotor was placed in the beaker, to thereby measure the viscosity for a measurement time of 50 seconds.

4. Observation of Film Structure

For observation of a film structure, a scanning electron microscope (SEM) and microscopic Raman were used.

(1) SEM

As the scanning electron microscope, Ultra55 manufactured by Carl Zeiss was used.

In order to observe a cross section of a capsule film, the prepared capsule film was cut to a small piece sliced into a ring, and the small piece was embedded into an epoxy resin. After that, the resultant was thinly cut with a microtome to produce a section for observation (having a size of about 300

μm to about 400 μm in each side and a thickness of from 2 μm to 3 μm). The section was subjected to vapor deposition treatment with PtPd. The section was scanned through irradiation with an electron beam at an acceleration voltage of 3 kV.

(2) Microscopic Raman

As a microscopic Raman device, Nicolet Almega XR manufactured by Thermo Fisher Scientific K.K. was used. An excitation wavelength was set to 532 nm. A resolution was set to about 10/cm (10 kaysers). An irradiation diameter was set to 1 μmφ (100× objective lens, 25 μm pinhole: information on a columnar inner portion having dimensions of 1 μmφ (planar direction)×2 μm (depth direction (=section thickness)) is obtained). An excitation output was set to 100% (10 mW or less at a sample position). An exposure time and the number of scans were set to 10 sec and 2, respectively.

The small capsule piece sliced into a ring was embedded into an epoxy resin and thinly cut with a microtome, to thereby produce a section having a thickness of 2 μm. The section was placed on a metal plate and observed.

5. Observation of Preparing Solution

A preparing solution was observed with an optical microscope (BX53 manufactured by Olympus Corporation) having a temperature regulation function of a stage. Transmission observation was performed through use of a 10× eyepiece lens and a 10× objective lens. The preparing solution at 55° C. was dropped onto a slide glass preheated on a stage also at 55° C., and further the preparing solution was covered with a cover glass preheated also to 55° C.

6. Concentration of Residual Salt in Film

A salt (sodium) in a capsule film was subjected to dry ashing treatment in accordance with the following procedure, and thereafter, was quantified by atomic absorption spectrophotometry (AAS). A sample was precisely weighed into a platinum crucible, and concentrated sulfuric acid was added thereto. After that, the resultant was heated until an organic substance was eliminated in an electric furnace at 650° C. Remaining ash was dissolved in diluted hydrochloric acid, appropriately diluted, and quantified with an atomic absorption spectrophotometer (Spectr AA-220 manufactured by Varian Medical Systems, Inc.).

7. Moisture Content (Water Content)

<Method of Measuring Water Content in Capsule Film by Loss-On-Drying Method>

A potassium carbonate saturated aqueous solution was loaded into a desiccator to obtain an atmosphere in a constant-humidity state, and a sample (hard capsule or film) was placed in the atmosphere in this state. The desiccator was sealed, and humidity therein was controlled at 25° C. for 1 week. The following saturated salt (aqueous solution) was used for humidity control. Specifically, in the presence of a potassium acetate saturated salt, a potassium carbonate saturated salt, and an ammonium nitrate saturated salt, atmospheres having a relative humidity of about 22%, about 43%, and about 60% were created, respectively. After the mass (wet mass) of the sample after humidity control was measured, the sample was then dried by heating at 105° C. for 2 hours, and the mass (dry mass) of the sample was measured again. From the difference between the mass before drying (wet mass) and the mass after drying (dry mass), the ratio of a moisture amount (water content) decreased by heating and drying at 105° C. for 2 hours was calculated in accordance with the following equation and was defined as the moisture content (mass %).

$$\text{Water content (\%)} = \frac{\text{(Wet mass of sample)} - \text{(Dry mass of sample)}}{\text{Wet mass of sample}} \times 100$$

8. Mechanical Strength of Capsule Film (Measurement of Elastic Modulus and Elongation at Break)

When the mechanical strength of a hard capsule film is evaluated, it is important to compare test films having the same thickness. Therefore, the mechanical strength of the film, which depended on the component composition of a hard capsule, was evaluated for a cast film produced by a casting method through use of a preparing solution having the same component composition as the component composition of a hard capsule-preparing solution instead of a hard capsule molded by a dipping method. Such film is excellent in uniformity of thickness and reproducibility of evaluation, and well reflects the mechanical strength as the capsule film.

The cast film was produced as described below. A metal applicator was set on a glass surface or a PET film held at room temperature. A preparing solution at 50° C. to 60° C. was poured onto the glass surface or the PET film, and the metal applicator was moved at a constant speed, to thereby produce a uniform film of 100 μm. After that, the film was dried at a temperature of from room temperature to 30° C. for about 10 hours.

In order to obtain the film having a uniform thickness of 100 μm, applicators having different gaps of from 0.4 mm to 1.5 mm were appropriately used.

The produced film was cut into a dumbbell shape of 5 mm×75 mm (specified in JIS K-7161-2-1BA), and then subjected to a tensile test with a compact tabletop testing machine (EZ-LX manufactured by Shimadzu Corporation). Both ends of the film were set on a holder (gap length: 60 mm) and pulled at a tensile rate of 10 mm/min. Then, an elongation of the film and a curve between a stress (tensile stress) that occurred in the film and an elongation rate (strain) were determined. An elastic modulus that is an indicator of hardness was obtained from the inclination of the curve in an elastic deformation region at a time of a low stress in FIG. 5, and an elongation rate at a breakpoint was determined as an elongation at break (Non-patent Literature 1, Chapter 4).

First, humidity control was performed for 1 week or more under humidity control conditions of 25° C. and a relative humidity of 22% or 60% through use of the same saturated salt as that in measurement of the moisture content described above, and after that, the tensile test was performed to evaluate the mechanical strength. The tensile test was performed at the same temperature and humidity as in each of the humidity control conditions. Under a low relative humidity of a relative humidity of 22%, in particular, a decrease in elongation at break becomes a problem. Under a high relative humidity of a relative humidity of 60%, a decrease in elastic modulus becomes a problem. The elastic modulus and the elongation at break at a relative humidity of 43% are each a substantially intermediate value between the value in the case of a relative humidity of 22% and the value in the case of a relative humidity of 60%.

III. Method of Preparing Preparing Solution

A capsule-preparing solution was prepared in accordance with the following procedure. All the operations were performed with stirring of a solution. In the following, solid contents of the components (i) to (v) are referred to as "polymer solid content". In addition, a total solution mass corresponds to a total mass of the polymer solid content, a basic neutralizer, and other solid contents (plasticizer, light-shielding agent, etc.) in addition to purified water that is a solvent. The polymer solid content concentration refers to a ratio (mass %) of a total mass of the polymer solid content to the total solution mass.

III-1. Method of Preparing Preparing Solution (Corresponding to Embodiment 3-1)

a. Purified water at room temperature was prepared in such an amount that the polymer solid content concentration finally reached a predetermined concentration (about 20%) in consideration of moisture amounts of a water dispersion liquid (solid content concentration: 30 mass %) of a methacrylic acid copolymer and a dispersion liquid of titanium oxide (concentration: 22 mass %) serving as a light-shielding agent to be added later.

b. An enteric cellulose compound was loaded into the purified water at room temperature and uniformly dispersed so as not to form lumps. After that, a basic neutralizer was loaded into the resultant to dissolve the enteric cellulose. Unless otherwise stated, the basic neutralizer was used in an amount (equivalent) required for completely neutralizing the enteric cellulose compound in the following examples.

c. This solution was increased in temperature to 83° C. Then, a nonionic water-soluble cellulose compound was loaded into the solution and uniformly dispersed therein so as not to form lumps, to thereby prepare a suspension liquid.

d. The dispersion liquid of the nonionic water-soluble cellulose compound was decreased in temperature to a temperature T2 equal to or lower than a dissolution temperature (cloud point) to partially dissolve the nonionic water-soluble cellulose compound, to thereby prepare a dispersion liquid. The partial dissolution temperature T2 was appropriately adjusted between 30° C. and 55° C.

e. The dispersion liquid prepared in the step d was held at a preparing solution temperature T3 (from 30° C. to 50° C. in the case of MC, from 45° C. to 60° C. in the case of HPMC, and from 30° C. to 40° C. in the case of HPC). As a result, the viscosity measured with a Brookfield type viscometer fell within a range of from about 1,000 mPa·s to about 3,000 mPa·s. The final polymer solid content concentration was finely adjusted through addition of hot pure water and evaporation so that the viscosity fell within the above-mentioned range.

f. The dispersion liquid of a methacrylic acid copolymer was added in any stage after the neutralization in the step b or after the completion of the partially dissolved solution of the nonionic water-soluble cellulose compound in the step e. Further, when titanium oxide was loaded, a water dispersion liquid was prepared in advance and then loaded before the operation in the step c. In all the above-mentioned steps, stirring is performed at 100 rpm to 1,000 rpm through use of a propeller stirring blade.

In this case, in the step d, it can be determined whether or not the dissolution of the nonionic water-soluble cellulose compound started based on a change in viscosity of the dispersion liquid as an indicator. Specifically, the viscosity of the dispersion liquid, which was substantially the same viscosity as that of water until then, is abruptly increased at a time when the dissolution starts. In addition, the white turbid dispersion liquid becomes an opaque white semi-transparent solution in association with the dissolution of part of particles. Accordingly, for a dispersion liquid of the nonionic water-soluble cellulose compound alone, a temperature T4 at which viscoelasticity was abruptly increased was measured in advance through evaluation of dynamic viscoelasticity, or an approximate temperature T4 at which the dispersion liquid became semi-transparent was measured in advance, and T2 and T3 were set to be higher (high temperature side) than T4.

III-2. Method of Preparing Preparing Solution (Corresponding to Embodiment 3-2)

a. Purified water at room temperature was prepared in such an amount that the polymer solid content concentration reached a predetermined concentration (about 20%) in consideration of moisture amounts of a water dispersion liquid (solid content concentration: 30 mass %) of a methacrylic acid copolymer, a dispersion liquid of a (meth)acrylic acid alkyl ester copolymer (solid content concentration: 30 mass %), and a dispersion liquid of titanium oxide serving as a light-shielding agent (concentration: 22 mass %) to be added later.

b. The dispersion liquid of a methacrylic acid copolymer was loaded into a predetermined amount of the above-mentioned purified water at room temperature. After that, sodium hydroxide (NaOH) serving as a basic neutralizer was loaded into the resultant to prepare a partially neutralized solution. Unless otherwise stated, NaOH was used in an amount required for partially neutralizing about 8% of a carboxyl group of the methacrylic acid copolymer in the following examples.

c. This partially neutralized solution was increased in temperature to 83° C. Then, the dispersion liquid of titanium oxide was loaded into the solution and sufficiently stirred with a three-one motor. After that, a nonionic water-soluble cellulose compound was loaded into the resultant and uniformly dispersed therein so as not to form lumps, to thereby prepare a suspension liquid. The suspension liquid was degassed. After that, PVA or a plasticizer was further loaded and dissolved in the resultant.

d. In the presence of NaOH, the dispersion liquid in which the nonionic water-soluble cellulose compound and the methacrylic acid copolymer were mixed (solution further containing titanium oxide and PVA) was decreased in temperature to a temperature T2 equal to or lower than a dissolution temperature (cloud point) of the nonionic water-soluble polymer, to thereby prepare a dispersion liquid in which the nonionic water-soluble cellulose compound was partially dissolved. The temperature T2 was appropriately adjusted between 30° C. and 55° C.

e. A dispersion liquid of NE30D was loaded into the dispersion liquid prepared in the step d while the dispersion liquid prepared in the step d was held at a preparing solution temperature T3 (from 35° C. to 40° C. in the case of MC, and from 30° C. to 65° C. in the case of HPMC). As a result, the viscosity measured with a Brookfield type viscometer fell within a range of from about 1,000 mPa·s to about 3,000 mPa·s. The final total solid content concentration was finely adjusted through addition of hot pure water and evaporation so that the viscosity fell within the above-mentioned range. In addition, in all the above-mentioned steps, stirring was performed at 100 rpm to 1,000 rpm through use of a propeller blade.

In this case, in the step d, it can be determined whether or not the dissolution of the nonionic water-soluble cellulose compound started based on a change in viscosity of the dispersion liquid as an indicator. Specifically, the viscosity of the dispersion liquid, which was substantially the same viscosity as that of water until then, is abruptly increased at a time when the dissolution starts. In addition, the while turbid dispersion liquid becomes an opaque white semi-transparent solution in association with the dissolution of part of particles. Accordingly, for a dispersion liquid of the nonionic water-soluble cellulose compound alone, a temperature T4 at which viscoelasticity was abruptly increased was measured in advance through evaluation of dynamic viscoelasticity, or an approximate temperature T4 at which the dispersion liquid became semi-transparent was measured in advance, and T2 and T3 were set to be higher (high temperature side) than T4.

IV. Method of Molding Capsule

A hard capsule was prepared by a cold pin immersion method through use of the capsule-preparing solution prepared in the above-mentioned section III. A mold pin (size: No. 2) left to stand at room temperature (about 25° C.) was immersed for several seconds in the capsule-preparing solution kept at a substantially constant temperature with the holding temperature T5 being set to substantially the same as T3, and the mold pin was pulled up into the atmosphere. The mold pin having the capsule-preparing solution adhering thereto was inverted upside down and dried at a room atmosphere temperature for 2 hours to 10 hours or more. The immersion time, the pull-up speed, and the like of the mold pin were appropriately adjusted so that the film thickness of a tubular capsule side surface became about 100 μm. After that, a capsule portion was pulled out of the mold pin and cut so that the length of the tubular portion became a predetermined length. The above-mentioned operation was performed for each of a cap and a body.

In the following, $\alpha'$, $\beta'$, $\gamma'$, $\sigma'$, $\varphi'$, $\delta'$, and $\varepsilon'$, which were composition ratios of the components of the preparing solution, were assumed to be directly the same as $\alpha$, $\beta$, $\gamma$, $\sigma$, $\varphi$, $\delta$, and $\varepsilon$, which were composition ratios of the components of the film.

V. Preparation Example

V-1. Preparation Example (Preparation Method of Embodiment 3-1)

In the following Examples 1 to 5 and Comparative Examples, each capsule-preparing solution was prepared in accordance with the preparation example III-1 (preparation method of the embodiment 3-1), and molding was performed by the molding method IV. When a total mass of solid contents (total polymer solid content mass) of the component (i) (first component), the component (ii) (second component), and the component (iii) (third component) was set to 100 mass %, the ratios of the component (i), the component (ii), and the component (iii) in terms of mass % were represented by $\alpha$, $\beta$, and $\gamma$, respectively. Mass ratios of a basic neutralizer (NaOH) and titanium oxide (light-shielding agent) with respect to the above-mentioned total polymer solid content mass were represented by $\delta$ (%) and $\varepsilon$ (%), respectively. In addition, a mass ratio of the solid contents of the components (i) to (iii) with respect to a total mass of purified water serving as a solvent and the solid contents of the components (i) to (iii) was defined as a polymer solid content concentration (%). Each specific composition is shown in Tables 3 to 7. In addition, the degree of neutralization (with respect to the component (iii)) in those tables refers to a degree of neutralization of the neutralization and dissolution of the component (iii) in the step A of the preparation method. Basically, the case in which the degree of neutralization of the component (iii) in the step A is 100% is defined as complete neutralization. Only in the case of Example 2-10 in which ammonia is used as a basic neutralizer, ammonia is added in excess in consideration of volatility, but a residue in the final film is estimated to be significantly smaller than 100%.

The degree of neutralization (with respect to the enteric polymer) refers to a degree of neutralization of the component (ii) and the component (iii) with respect to the entire enteric polymer. A dispersion liquid of an enteric methacrylic acid copolymer is used as the component (ii), and a basic neutralizer is added only in a neutralization process of the component (iii) in the step A in terms of the preparation step. Therefore, the degree of neutralization only refers to an apparent degree of neutralization with respect to the enteric polymer of the entire preparing solution. It is unclear at which ratio each of the component (ii) and the component (iii) after being mixed is neutralized, but in order to obtain a sufficiently fine dispersion liquid, complete neutralization is required in the neutralization of the component (iii). The degree of neutralization with respect to the entire enteric polymer was able to be set to less than 50% through mixing with the water dispersion liquid of the component (iii). With this, an adverse effect caused by an excess residual salt in the capsule film can be prevented.

1. Example 1

Capsules were prepared in accordance with the procedure of the above-mentioned section III-1. through use of methylcellulose (MC) having a "viscosity value" of 100 mPa·s or more as a nonionic water-soluble cellulose compound and the capsule-preparing solutions having the compositions of Examples 1-1 to 1-7 shown in Table 3. Each of the capsule-preparing solutions became a while turbid (suspended) dispersion liquid at the temperature T5 at a time of immersion of a molding pin. In addition, it was separately confirmed that the capsule-preparing solution became a white turbid or semi-transparent dispersion liquid even before loading of titanium oxide.

Further, a hard capsule having a size of No. 2 was created by the method of the above-mentioned section IV.

Then, each of the obtained capsules was subjected to a dissolution test in a first liquid and a second liquid in accordance with the above-mentioned section II.1. The dissolution rate of any of the capsules after 2 hours from immersion in the first liquid was less than 10%, and thus poor solubility in an acidic solution was exhibited. Meanwhile, the dissolution rate of any of the capsules after 30 minutes from immersion in the second liquid was 70% or more. All the capsules were verified to be readily soluble in a neutral solution.

The hard capsule of Example 1-3 had satisfactory dissolution characteristics in the dissolution test. However, the degree of neutralization thereof with respect to the entire enteric polymer was as high as 50% or more, and hence not only the solubility in a neutral test solution but also the solubility in, in particular, pure water was high. In addition, there was a concern about yellowing of the film at a time of storage.

TABLE 3

| | First Component MC | Second Component Methacrylic acid copolymer | α (%) | Third Component Enteric cellulose compound | β (%) | Basic neutralizer Substance name | Y (%) | Degree of neutralization (%) With respect to third component δ (%) |
|---|---|---|---|---|---|---|---|---|
| Example 1-1 | SM4000 | 26.10 | L30D55 | 36.95 | HP50 | 36.95 | NaOH | 2.40 | 99.9 |
| Example 1-2 | SM4000 | 27.65 | L30D55 | 20.67 | HP50 | 51.68 | NaOH | 3.36 | 100.0 |
| Example 1-3 | SM100 | 37.98 | L30D55 | 10.34 | HP50 | 51.68 | NaOH | 3.36 | 100.0 |
| Example 1-4 | SM100 | 36.88 | L30D55 | 31.56 | HP50 | 31.56 | NaOH | 2.05 | 99.9 |
| Example 1-5 | SM4000 | 29.14 | L30D55 | 35.43 | HPMCAS-MF | 35.43 | NaOH | 1.24 | 72.9 |
| Example 1-6 | SM4000 | 49.18 | L30D55 | 25.41 | HP50 | 25.41 | NaOH | 1.65 | 99.9 |
| Example 1-7 | SM4000 | 49.28 | L30D55 | 25.36 | HPMCAS-MF HP50 | 12.68 12.68 | NaOH | 1.43 | 100.0 |

| | Degree of neutralization (%) With respect to enteric polymer | Others Substance name | ε (%) | Polymer solid content concentration (%) | pH 1.2 Dissolution rate after 2 hours (%) | pH 6.8 Time (min) | Dissolution rate (%) |
|---|---|---|---|---|---|---|---|
| Example 1-1 | 23.2 | Titanium oxide | 3.2 | 22.7 | <1.0 | 30 | 100 |
| Example 1-2 | 43.1 | None | 0 | 21.3 | 2.7 | 30 | 100 |
| Example 1-3 | 60.2 | None | 0 | 21.3 | 9.2 | 30 | 100 |
| Example 1-4 | 23.2 | Titanium oxide | 3.2 | 20.0 | 3.2 | 30 | 100 |
| Example 1-5 | 13.3 | None | 0 | 19.8 | 4.7 | 30 | 94 |
| Example 1-6 | 23.2 | None | 0 | 19.7 | 6.2 | 45 | 83.3 |
| Example 1-7 | 20.8 | None | 0 | 18.7 | 6.8 | 30 | 70.3 |

2. Example 2

Capsules were prepared in accordance with the procedure of the above-mentioned section III-1. through use of hydroxypropyl methylcellulose (HPMC) having a "viscosity value" of 100 mPa·s or more as a nonionic water-soluble cellulose compound and the capsule-preparing solutions having the compositions of Examples 2-1 to 2-10 shown in Table 4. Each of the capsule-preparing solutions of Example 2 became a white turbid dispersion liquid at a temperature of 55° C. at a time of immersion of a molding pin.

Further, a hard capsule having a size of No. 2 was created by the method of the above-mentioned section IV.

Then, each of the obtained capsules was subjected to a dissolution test in a first liquid and a second liquid in accordance with the above-mentioned section II.1. The dissolution rate of any of the capsules prepared from the capsule-preparing solutions of Examples 2-1 to 2-3 and 2-5 to 2-10 after 2 hours from immersion in the first liquid was less than 10%. The dissolution rate of the capsule prepared from the capsule-preparing solution of Example 2-4 was 16.4%. Meanwhile, the dissolution rate of any of the capsules prepared from the capsule-preparing solutions of Examples 2-1 to 2-4 and 2-6 to 2-10 after 30 minutes from immersion in the second liquid was 70% or more. In general, when it is preferred that the capsule be rapidly disintegrated after reaching the intestines, the characteristics of Examples 2-1 to 2-4 and 2-10 are desired. Meanwhile, when it is desired that the capsule further reach a lower part of the intestinal tract, and a drug be gradually released, the characteristics of Examples 2-7 to 2-9 may be appropriately selected.

Next, a transverse section of a film of the capsule prepared from the capsule-preparing solution of Example 2-2 was cut out and observed with a scanning electron microscope. As a result, as shown in FIG. 2, a structure formed of an elongated island phase and a sea phase was observed. When a component of each phase was analyzed by microscopic Raman analysis, it was found that a layer in which coarse particles were present in FIG. 2 formed the sea phase, and the coarse particles were an aggregate of titanium oxide. Each particle diameter was large, or the particles were aggregated, and hence it is estimated that the particles were not able to enter the island portion of undissolved HPMC. The composition of residual sodium in the capsule film measured with an atomic absorption spectrophotometer was substantially the same as the concentration of NaOH in a jelly solution. From this, it was estimated that substantially the entire amount of NaOH reacted and reacted with any one of the second component and the third component to form a salt (—COONa) to be taken in the film. The capsule was stored at 60° C. for 3 days in a dry oven, but a change such as yellowing was not observed. In addition, the dissolution test results were hardly changed. It is considered that an adverse effect on the film caused by the salt was not observed because the partial neutralization amount of the enteric cellulose compound and the methacrylic acid copolymer with respect to the entire enteric polymer was sufficiently low, i.e., less than 50%. In addition, it was able to be confirmed by a Raman analysis method that the composition of polymer components in the preparing solution was almost kept also in the capsule film.

Next, the preparing solution used in Example 2-2 was dropped onto a slide glass on a stage kept at a temperature of 55° C., and further the preparing solution was sealed with a cover glass preheated to 55° C. The preparing solution was observed with an optical microscope. A transmission image in this case is shown in FIG. 3. Whitish portions in FIG. 3 correspond to solid particles of partially dissolved HPMC. A blackish region on the periphery corresponds to an aqueous solution containing the enteric polymer as a main component and looks black because the aqueous solution contains titanium oxide.

Further, changes in storage elastic modulus G' (Pa) and loss elastic modulus G" (Pa) when the preparing solution used in Example 2-2 was decreased in temperature from the temperature T1 to room temperature are shown in FIG. 4. The storage elastic modulus G' (Pa) exceeds the loss elastic modulus G" (Pa) between 40° C. to 35° C., and thus, the preparing solution used in Example 2-2 was verified to be suitable for preparing a hard capsule by a cold gelation method.

TABLE 4

| | First Component | Second Component Methacrylic acid copolymer | | Third Component Enteric cellulose compound | | Basic neutralizer | | Degree of neutralization (%) With respect to third component |
|---|---|---|---|---|---|---|---|---|
| | HPMC | α (%) | | β (%) | | Substance name | δ (%) | |
| | | | | | γ (%) | | | |
| Example 2-1 | 65SH4000 | 26.10 | L30D55 | 36.95 | HP50 36.95 | NaOH | 2.41 | 100.3 |
| Example 2-2 | 65SH400 | 36.88 | L30D55 | 31.56 | HP50 31.56 | NaOH | 2.05 | 99.9 |
| Example 2-3 | 65SH400 | 36.44 | L30D55 | 21.19 | HP50 42.37 | NaOH | 2.75 | 99.9 |
| Example 2-4 | 65SH400 | 47.58 | L30D55 | 26.21 | HP50 26.21 | NaOH | 1.71 | 100.4 |
| Example 2-5 | 65SH400 | 26.85 | L30D55 | 52.24 | HP50 20.91 | NaOH | 1.36 | 100.1 |
| Example 2-6 | 60SH4000 | 26.10 | L30D55 | 36.95 | HP50 36.95 | NaOH | 2.41 | 100.3 |
| Example 2-7 | 60SH4000 | 36.88 | L30D55 | 31.56 | HP50 31.56 | NaOH | 2.05 | 99.9 |
| Example 2-8 | 60SH10000 | 38.96 | L30D55 | 30.52 | HPMCAS-MF 15.26 HP50 15.26 | NaOH | 1.72 | 99.7 |
| Example 2-9 | 60SH4000 | 26.10 | FS30D | 36.95 | HP50 36.95 | NaOH | 2.41 | 100.3 |
| Example 2-10 | 65SH400 | 38.14 | L30D55 | 30.93 | HP50 30.93 | Ammonia | 1.55 | 182.9 |

| | Degree of neutralization (%) With respect to enteric polymer | Others Substance name | ε (%) | Polymer solid content concentration (%) | pH 1.2 Dissolution rate after 2 hours (%) | pH 6.8 Time (min) | pH 6.8 Dissolution rate (%) |
|---|---|---|---|---|---|---|---|
| Example 2-1 | 23.3 | Titanium oxide | 3.2 | 20.8 | <1.0 | 30 | 99.4 |
| Example 2-2 | 23.2 | Titanium oxide | 3.2 | 19.0 | 4.3 | 30 | 99.4 |
| Example 2-3 | 37.6 | Titanium oxide | 3.2 | 18.9 | 4.5 | 30 | 100 |
| Example 2-4 | 23.3 | Titanium oxide | 3.1 | 15.3 | 16.4 | 30 | 74.8 |
| Example 2-5 | 10.8 | Titanium oxide | 3.1 | 19.6 | <1.0 | — | — |
| Example 2-6 | 23.3 | Titanium oxide | 3.2 | 20.8 | <1.0 | 30 | 100 |
| Example 2-7 | 23.2 | Titanium oxide | 3.2 | 19.0 | <1.0 | 60 | 46.2 |
| Example 2-8 | 20.8 | None | 0 | 16.7 | 4.6 | 60 | 61.6 |
| Example 2-9 | 61.9 | Titanium oxide | 3.2 | 20.8 | 9.5 | 60 | 98.8 |
| Example 2-10 | 42.2 | Titanium oxide | 3.1 | 18.5 | 7.5 | 30 | 80.1 |

In Table 4, the symbol "-" indicates that measurement was not performed.

3. Example 3

A capsule was prepared in accordance with the procedure of the above-mentioned section III-1. through use of hydroxypropyl cellulose (HPC) having a "viscosity value" of 100 mPa·s or more as a nonionic water-soluble cellulose compound and the capsule-preparing solution having the composition of Example 3-1 shown in Table 5. The capsule-preparing solution of Example 3 became a while turbid dispersion liquid at a temperature of 55° C. at a time of immersion of the molding pin.

Further, a hard capsule having a size of No. 2 was created by the method of the above-mentioned section IV.

Then, the obtained capsule was subjected to a dissolution test in a first liquid and a second liquid in accordance with the above-mentioned section II.1. The dissolution rate of the capsule prepared from the capsule-preparing solution of Example 3-1 after 2 hours from immersion in the first liquid was 1.4%. In addition, the dissolution rate thereof after 30 minutes from immersion in the second liquid was 100%. The capsule prepared from the preparing solution of Example 3-1 was verified to be readily soluble in a neutral solution.

TABLE 5

| | First Component | Second Component | | Third Component | | Basic neutralizer | | Degree of neutralization (%) | |
|---|---|---|---|---|---|---|---|---|---|
| | | Methacrylic acid copolymer | | Enteric cellulose compound | | | | With respect to third component | With respect to enteric polymer |
| | HPC | | α (%) | | β (%) | Substance name | γ (%) | δ (%) | |
| Example 3-1 | HPC-H | L30D55 | 26.10 | HP50 | 36.95 | NaOH | 37 | 2.41 | 100.3 | 23.3 |

| | Others | | Polymer solid content concentration (%) | pH 1.2 Dissolution rate after 2 hours (%) | pH 6.8 | |
|---|---|---|---|---|---|---|
| | Substance name | ε (%) | | | Time (minute) | Dissolution rate (%) |
| Example 3-1 | Titanium oxide | 3.2 | 20.8 | 1.4 | 30 | 100 |

4. Example 4 and Comparative Example 4

Capsules were prepared in accordance with the procedure of the above-mentioned section III-1. through use of hydroxypropyl methylcellulose (HPMC) having various "viscosity values" as a nonionic water-soluble cellulose compound and the capsule-preparing solutions having the compositions of Examples 4-1 to 4-3 and Comparative Examples 4-1 to 4-4 shown in Table 6.

Each of the capsule-preparing solutions was measured for viscosity with a Brookfield type viscometer and dynamic viscoelasticity behavior at a time of a decrease in temperature with a rheometer through use of the above-mentioned apparatus in accordance with the above-mentioned procedure. The characteristics to be evaluated are the following three points: i. whether or not the viscosity at the preparing solution holding (immersion) temperatures T3 and T5 of about 55° C. in FIG. 1 falls within a preferred range; ii. whether or not the viscosity is abruptly increased due to the structural viscosity or the start of cold gelation within a range of T4 of from about 30° C. to about 50° C. in FIG. 1 at a time of cooling; and iii. whether or not the capsule-preparing solution is finally gelled when G'>G" is established at a drying temperature in the vicinity of room temperature (from 20° C. to 30° C.). In Table 6, there are shown the composition of each capsule-preparing solution, the viscosity of each preparing solution at T5 (Brookfield type viscometer), measurement results of dynamic viscoelasticity at a time of a decrease in temperature, that is, presence or absence of gelation in the vicinity of room temperature (the preparing solution is judged as being gelled when G'>G" is established in rheometer measurement), and presence or absence of an abrupt increase in viscosity at about 30° C. to about 50° C. When the "viscosity value" of HPMC was 100 mPa·s or more (Examples 4-1, 4-2, and 4-3), the viscosity of the preparing solution reached about 1,000 mPa·s to about 3,000 mPa·s, and an abrupt increase in viscosity at 30° C. to 50° C., that is, a gelation requirement in the vicinity of room temperature was satisfied. Meanwhile, when the "viscosity value" of HPMC was less than 100 mPa·s (Comparative Examples 4-1, 4-2, and 4-3), it was shown that an increase in viscosity at about 30° C. to about 50° C. was gentle, and gelation in the vicinity of room temperature was not observed.

Thus, it was shown that the "viscosity value" of the nonionic water-soluble cellulose compound to be used in the capsule-preparing solution assumed to be applied to the cold pin immersion method was preferably 100 mPa·s or more.

TABLE 6

| | Component (i) HPMC | Component (ii) Methacrylic α (%) acid copolymer | | Component (iii) Enteric β (%) cellulose compound | | Basic neutralizer Y (%) Substance name | | δ (%) |
|---|---|---|---|---|---|---|---|---|
| Example 4-1 | 65SH400 | 38.8 | L30D55 | 30.6 | HP50 | 30.6 | NaOH | 1.99 |
| Example 4-2 | 60SH4000 | 38.8 | L30D55 | 30.6 | HP50 | 30.6 | NaOH | 1.99 |
| Example 4-3 | 65SH4000 | 38.8 | L30D55 | 30.6 | HP50 | 30.6 | NaOH | 1.99 |
| Comparative Example 4-1 | TC-5R (Labeled viscosity: 6) | 38.8 | L30D55 | 30.6 | HP50 | 30.6 | NaOH | 1.99 |
| Comparative Example 4-2 | TC-5S (Labeled viscosity: 15) | 38.8 | L30D55 | 30.6 | HP50 | 30.6 | NaOH | 1.99 |
| Comparative Example 4-3 | 60SH50 | 38.8 | L30D55 | 30.6 | HP50 | 30.6 | NaOH | 1.99 |
| Comparative Example 4-4 | 65SH50 | 38.8 | L30D55 | 30.6 | HP50 | 30.6 | NaOH | 1.99 |

| | Degree of neutralization (%) With respect to Component (iii) | With respect to enteric polymer | Polymer solid content concentration (%) | Preparing solution viscosity (mPa · s) | Gelation in the vicinity of room temperature Represented by Symbol "○" when G' > G" is established | Abrupt increase in viscosity at 30° C. to 50° C. |
|---|---|---|---|---|---|---|
| Example 4-1 | 100.1 | 23.2 | 19.6 | 1,910 | ○ | ○ |
| Example 4-2 | 100.1 | 23.2 | 19.6 | 3,110 | ○ | ○ |
| Example 4-3 | 100.1 | 23.2 | 19.6 | 2,690 | ○ | ○ |
| Comparative Example 4-1 | 100.1 | 23.2 | 19.6 | 180 | x | x |
| Comparative Example 4-2 | 100.1 | 23.2 | 19.6 | 303 | x | x |
| Comparative Example 4-3 | 100.1 | 23.2 | 19.6 | 2,430 | x | x |
| Comparative Example 4-4 | 100.1 | 23.2 | 19.6 | 3,500 | x | x |

5. Example 5 and Reference Example 1

In order to confirm that the component (i), the component (ii), and the neutralized component (iii) are all required in the preparing solutions of the method of preparing a preparing solution of the embodiment 3-1 and the cold pin immersion method according to the present disclosure, various solutions were prepared by eliminating any one of the components and simply substituting the mass corresponding to the eliminated component with purified water, and the suitability as a capsule-preparing solution was confirmed. In Table 7, there are shown a composition of each preparing solution (not containing titanium oxide in any case), measurement results of dynamic viscoelasticity at a time of a decrease in temperature with a rheometer, that is, presence or absence of gelation in the vicinity of room temperature (the preparing solution is judged as being gelled when G'>G" is established in rheometer measurement, this case is represented by Symbol "○". Even in the case where G'<G" is established or G'>G" is apparently established, when G' is significantly small, and solidification is actually impossible, this case is represented by Symbol "x"), and presence or absence of an abrupt increase in viscosity at about 30° C. to about 50° C. In addition, as "independent dried film formation", whether or not an independent film was obtained by a casting method was evaluated. This evaluation indicates whether or not an independent film was able to be formed without using another support member, and further whether or not an obtained film had appropriate mechanical strength as an empty hard capsule film. In this case, in order to obtain a cast film having a thickness of about 100 μm, a polymer solid content concentration was appropriately adjusted while a ratio between the polymer components was kept in addition to simple substitution of a characteristic component with water in some cases. The case in which an independent film was able to be formed is represented by Symbol "○" in Table 7. The following case is represented by Symbol "x". Specifically, even when a polymer solid content concentration was slightly adjusted in a casting method, a resultant film was too brittle or too soft when the film was peeled from a substrate to which the preparing solution was applied, with the result that it was difficult to peel the film as an independent film.

Regarding the capsule-preparing solution (Example 5) according to the present disclosure containing all the three kinds of components: HPMC serving as the component (i), the dispersion liquid of Eudragit (L30D55) serving as the component (ii), and HP50 (neutralized with NaOH) serving as the component (iii), and solutions of Reference Examples 1-1 to 1-8 lacking in any one of the components, dynamic viscoelasticity behaviors at a time of a decrease in temperature were compared with each other. In Example 5 containing all the components, substantially the same conditions as those in the case of eliminating titanium oxide in Example 2-2 are established. The cases in which an eliminated component was simply substituted with water in the same mass as that of the eliminated component based on the case in which titanium oxide was eliminated from Example 2-2 were defined as Reference Examples 1-1 to 1-8.

In the case of the dispersion liquid alone in which the component (i) was partially dissolved (Reference Example 1-1) and the case in which only the dispersion liquid of the component (i) and the neutralized solution of the component (iii) were contained (Reference Example 1-4), an abrupt increase in viscosity was observed, but G'<G" was finally established in the vicinity of room temperature, with the result that gelation did not occur.

In the solution of the component (iii) (and NaOH) alone (Reference Example 1-2), the dispersion liquid of the component (ii) alone (Reference Example 1-3), and the case in which only the neutralized solution of the component (iii) and the dispersion liquid of the component (ii) were contained (Reference Example 1-5), liquid behavior was substantially completely exhibited over the entire temperature region, and G' and G" were both significantly small and less than about 100 mPa·s over a temperature range of from 55° C. to room temperature.

When only the component (i) and the dispersion liquid of the component (ii) were contained (without containing a neutralizer) (Reference Example 1-6), significant aggregation occurred immediately after mixing of both the components, and hence this case was unsuitable as a capsule-preparing solution. When the component (i), the component (ii), and the component (iii) were contained, but the component (ii) and the component (iii) were completely neutralized in an entire amount with a neutralizer (Reference Example 1-7), an abrupt increase in viscosity was observed, but the temperature in this case was lower than 30° C., and gelation (G'>G") did not occur in the vicinity of room temperature. From the foregoing, it was considered that it was important that all the component (i), the component (ii), and the neutralized component (iii) were contained in a capsule-preparing solution for preparing an enteric hard capsule. In particular, when the component (i) and the component (ii) were mixed with each other, the basic neutralizer used for neutralization of the component (iii) was effective for preventing aggregation of the dispersion liquid. Meanwhile, when the entire enteric polymer was neutralized (that is, when the component (ii) as well as the component (iii) was completely neutralized), preferred cold gelation characteristics were lost. In addition, with the component (i) and the component (ii) (partially neutralized) (Reference Example 1-8), mixing and film formation were possible, but only a significantly brittle film was formed, and it was difficult to obtain an independent dried film. Due to the presence of the component (iii), the appropriate mechanical strength as an independent hard capsule can be realized.

TABLE 7

| | Content | Component (i) HPMC | α (%) | Component (ii) Methacrylic acid copolymer | β (%) | Component (iii) Enteric cellulose compound | γ (%) | Basic neutralizer Substance name | δ (%) |
|---|---|---|---|---|---|---|---|---|---|
| Example 5 | All components | 65SH400 | 38.81 | L30D55 | 30.60 | HP50 | 30.60 | NaOH | 1.99 |
| Reference Example 1-1 | Dispersion liquid of component (i) | 65SH400 | 38.81 | Substituted with water | 30.60 | Substituted with water | 30.60 | None | 0 |
| Reference Example 1-2 | Neutralized solution of component (iii) | Substituted with water | 38.81 | Substituted with water | 30.60 | HP50 | 30.60 | NaOH | 1.99 |
| Reference Example 1-3 | Dispersion liquid of component (ii) | Substituted with water | 38.81 | L30D55 | 30.60 | Substituted with water | 30.60 | NaOH | 0 |
| Reference Example 1-4 | Component (i) + neutralized liquid of component (iii) | 65SH400 | 38.81 | Substituted with water | 30.60 | HP50 | 30.60 | NaOH | 1.99 |
| Reference Example 1-5 | Dispersion liquid of component (ii) + neutralized solution of component (iii) | Substituted with water | 38.81 | L30D55 | 30.60 | HP50 | 30.60 | NaOH | 1.99 |
| Reference Example 1-6 | Component (i) + dispersion liquid of component (ii) (without neutralizer) | 65SH400 | 38.81 | Substituted with water | 30.60 | Substituted with water | 30.60 | NaOH | 0 |
| Reference Example 1-7 | Component (i) + components (ii) and (iii) (completely neutralized and dissolved) | 65SH400 | 38.81 | L30D55 | 30.60 | HP50 | 30.60 | NaOH | 8.57 |
| Reference Example 1-8 | Component (i) + dispersion liquid of component (ii) (partially neutralized) | 65SH400 | 38.81 | L30D55 | 30.60 | Substituted with water | 30.60 | NaOH | 1.99 |

TABLE 7-continued

| | Degree of neutralization (%) | | | Abrupt | | |
|---|---|---|---|---|---|---|
| | With respect to component (iii) | With respect to enteric polymer | Polymer solid content concentration (%) | Gelation in the vicinity of room temperature | increase in viscosity at 30° C. to 50° C. | Independent dried film formation |
| Example 5 | 100.1 | 23.2 | 19.61 | ○ | ○ | ○ |
| Reference Example 1-1 | 0.0 | 0.0 | | x | ○ | ○ |
| Reference Example 1-2 | 100.1 | 100.1 | | x | x | ○ |
| Reference Example 1-3 | 0.0 | 0.0 | | x | x | x |
| Reference Example 1-4 | 100.1 | 100.1 | | x | ○ | ○ |
| Reference Example 1-5 | 100.1 | 23.2 | | x | x | ○ |
| Reference Example 1-6 | 0.0 | 0.0 | | Aggregation immediately after mixing | | |
| Reference Example 1-7 | 430.9 | 100.0 | 19.6 | x | ○ | x |
| Reference Example 1-8 | | 30.2 | | ○ | ○ | x |

V-2. Preparation Example (Preparation Method of Embodiment 3-2)

In the following Examples 6 and 7, each capsule-preparing solution was prepared in accordance with the preparation example III-2 (preparation method of the embodiment 3-2), and molding was performed by the molding method IV. When a total mass of solid contents (total polymer solid content mass) of the component (i) (first component), the component (ii) (second component), the component (iv) (fourth component), and the component (v) (fifth component) was set to 100 mass %, the ratios of the component (i), the component (ii), the component (iv), and the component (v) in terms of mass % were represented by α, β, σ, and β, respectively. Mass ratios of a basic neutralizer and titanium oxide (light-shielding agent) with respect to the above-mentioned total polymer solid content mass were represented by δ (%) and ε (%), respectively. In addition, a mass ratio of the solid contents of the component (i), the component (ii), the component (iv), and the component (v) with respect to a total mass of purified water serving as a solvent and the solid contents of the component (i), the component (ii), the component (iv), and the component (v) was defined as a polymer solid content concentration (%). In Tables 8 and 9, the degree of neutralization refers to a degree of neutralization of a basic neutralizer to be added to the dispersion liquid of L30D55 with respect to the mass of a solid content of L30D55 in the step A' of preparation. In this case, the basic neutralizer is added in order to prevent aggregation from occurring immediately after mixing of the component (i) and the component (ii), and is not added in order to obtain fine particles through dissolution of the component (ii) itself. The degree of neutralization thereof may be sufficiently as low as about 8%.

In Example 6-8, a dispersion liquid of fine particles obtained by neutralizing and dissolving L10055 which was dried and formed into solid powder at a degree of neutralization of about 8% was used also in the step A' instead of a colloid dispersion liquid of L30D55.

1. Example 6

Capsule-preparing solutions were prepared in accordance with the procedure of the above-mentioned section III-2. through use of hydroxypropyl methylcellulose (HPMC) having a "viscosity value" of 100 mPa·s or more as a nonionic water-soluble cellulose compound and the capsule-preparing solutions having the compositions of Examples 6-1 to 6-10 shown in Table 8. Each of the capsule-preparing solutions became a white turbid dispersion liquid at the temperature T5 at a time of immersion of a molding pin. In addition, it was separately confirmed that the capsule-preparing solution became a white turbid (suspended) or semi-transparent dispersion liquid even before loading of titanium oxide.

TABLE 8

| | First component | | Second component Methacrylic acid copolymer | | Fourth component Methacrylic acid alkyl ester copolymer | | Fifth component | | Basic neutralizer | |
|---|---|---|---|---|---|---|---|---|---|---|
| | HPMC | α (%) | | β (%) | | σ (%) | PVA or plasticizer | φ (%) | Substance name | δ (%) |
| Example 6-1 | 60SH10000 | 16.7 | L30D55 | 62.5 | NE30D | 20.8 | None | 0 | NaOH | 1.04 |
| Example 6-2 | 90SH4000SR | 8.4 | L30D55 | 62.5 | NE30D | 20.8 | EG48P | 8.3 | NaOH | 1.04 |
| Example 6-3 | 90SH100SR | 8.4 | L30D55 | 62.5 | NE30D | 20.8 | EG48P | 8.3 | NaOH | 1.04 |
| Example 6-4 | 90SH100000SR | 5 | L30D55 | 62.5 | NE30D | 20.8 | EG48P | 11.7 | NaOH | 1.04 |

TABLE 8-continued

| | | | | | | | | | | |
|---|---|---|---|---|---|---|---|---|---|---|
| Example 6-5 | 60SH10000 | 3.1 | L30D55 | 62.5 | NE30D | 20.9 | PEG 35000 | 10.4 | NaOH | 1.04 |
| | 90SH100000SR | 3.1 | | | | | | | | |
| Example 6-6 | 90SH4000SR | 8.45 | L30D55 FS30D | 41.5 20.8 | NE30D | 20.8 | EG48P | 8.45 | NaOH | 0.76 |
| Example 6-7 | SM100 | 37.7 | L30D55 | 41.5 | NE30D | 20.8 | None | 0 | NaOH | 0.70 |
| Example 6-8 | 60SH10000 | 16.7 | L10055 | 62.5 | NE30D | 20.8 | None | 0 | NaOH | 1.04 |
| Example 6-9 | 60SH10000 | 17.0 | L30D55 | 41.5 | NE30D | 41.5 | None | 0 | NaOH | 0.70 |
| Example 6-10 | 65SH400 | 37.7 | L30D55 | 41.5 | None | 0 | PG | 20.8 | NaOH | 0.70 |

| | Degree of neutralization With respect to second component | Others | | Polymer solid content concentration (%) | pH 1.2 Dissolution rate after 2 hours (%) | pH 6.8 | |
|---|---|---|---|---|---|---|---|
| | | Substance name | ε (%) | | | Time (minute) | Dissolution rate (%) |
| Example 6-1 | 7.7 | Titanium oxide | 3.1 | 22.1 | <1.0 | 45 | 100 |
| Example 6-2 | 7.7 | Titanium oxide | 3.1 | 17.8 | 2.2 | 45 | 100 |
| Example 6-3 | 7.7 | Titanium oxide | 3.1 | 19.2 | 2 | 45 | 100 |
| Example 6-4 | 7.7 | Titanium oxide | 3.1 | 19.2 | 10.1 | 45 | 100 |
| Example 6-5 | 7.7 | Titanium oxide | 3.1 | 25.0 | 0.1 | 45 | 100 |
| Example 6-6 | 7.8 | Titanium oxide | 3.1 | 17.8 | 2.2 | 45 | 100 |
| Example 6-7 | 7.8 | Titanium oxide | 3.1 | 18.3 | 2.1 | 45 | 99.0 |
| Example 6-8 | 7.7 | Titanium oxide | 3.1 | 22.1 | <1.0 | 30 | 98.4 |
| Example 6-9 | 7.8 | Titanium oxide | 3.1 | 23.9 | <1.0 | 45 | 90.1 |
| Example 6-10 | 7.8 | Titanium oxide | 3.1 | 15.4 | 3.2 | 40 | 97.2 |

Then, each of the obtained capsules was subjected to a dissolution test in a first liquid and a second liquid in accordance with the above-mentioned section II.1. The dissolution rate of any of the capsules after 2 hours from immersion in the first liquid was less than 10% except for the case of 10.1% in Example 6-4 in which 10 mass % or more of PVA serving as the fifth component was contained, and thus poor solubility in an acidic solution was exhibited. Meanwhile, the dissolution rate of any of the capsules after 45 minutes from immersion in the second liquid was 90% or more. All the capsules were verified to be readily soluble in a neutral solution.

In FIG. 6 and FIG. 7, there are shown an optical microscopic image of the capsule-preparing solution of Example 6-2, and a scanning electron microscopic image of a cross section of a capsule film. It was confirmed that the capsule-preparing solution was a dispersion liquid in which fine solid particles of HPMC serving as the component (i) were dispersed. In addition, it was confirmed that the capsule film after being dried had a sea-island structure in which an island phase contained HPMC as a main component. In addition, it was able to be confirmed by a Raman analysis method that the composition of polymer components in the preparing solution was substantially kept also in the capsule film.

2. Example 7 and Reference Example 2

In order to confirm that the component (i), the component (ii), the component (iv), and the basic neutralizer are all required in the preparing solution of the cold pin immersion method according to the present disclosure, various solutions were prepared by eliminating any one of the components and simply substituting the mass corresponding to the eliminated component with purified water in the preparation method of the embodiment 3-2, and the suitability as a capsule-preparing solution was confirmed. In Table 9, there are shown a composition of each preparing solution (not containing titanium oxide in any case), measurement results of dynamic viscoelasticity at a time of a decrease in temperature with a rheometer, that is, presence or absence of gelation in the vicinity of room temperature, and presence or absence of an abrupt increase in viscosity at about 30° C. to about 50° C. In addition, the possibility of "independent dried film formation" is also shown.

TABLE 9

| | | Component (i) | | Component (ii) Methacrylic acid copolymer | | Component (iv) Methacrylic acid alkyl ester copolymer | | Component (v) PVA or plasticizer | |
|---|---|---|---|---|---|---|---|---|---|
| | Content | HPMC | α (%) | | β (%) | | σ (%) | | φ (%) |
| Example 7 | All components | 90SH4000SR | 9.6 | L30D55 | 60.6 | NE30D | 20.2 | EG48P | 9.6 |
| Reference | Dispersion liquid of | 90SH4000SR | 9.6 | Substituted | 60.6 | Substituted | 20.2 | Substituted | 9.6 |

TABLE 9-continued

| | | | | | | | | | |
|---|---|---|---|---|---|---|---|---|---|
| Example 2-1 | component (i) | | | with water | | with water | | with water | |
| Reference Example 2-2 | Dispersion liquid of component (ii) | Substituted with water | 9.6 | L30D55 | 60.6 | Substituted with water | 20.2 | Substituted with water | 9.6 |
| Reference Example 2-3 | Dispersion liquid of component (iv) | Substituted with water | 9.6 | NE30D | 60.6 | Substituted with water | 20.2 | Substituted with water | 9.6 |
| Reference Example 2-4 | Solution of component (v) | Substituted with water | 9.6 | Substituted with water | 60.6 | Substituted with water | 20.2 | EG48P | 9.6 |
| Reference Example 2-5 | Dispersion liquid of component (ii) + dispersion liquid of component (iv) | Substituted with water | 9.6 | L30D55 | 60.6 | NE30D | 20.2 | Substituted with water | 9.6 |
| Reference Example 2-6 | Dispersion liquid of component (ii) + component (v) | Substituted with water | 9.6 | L30D55 | 60.6 | Substituted with water | 20.2 | EG48P | 9.6 |
| Reference Example 2-7 | Dispersion liquid of component (iv) + component (v) | Substituted with water | 9.6 | Substituted with water | 60.6 | NE30D | 20.2 | EG48P | 9.6 |
| Reference Example 2-8 | Dispersion liquid of component (ii) + dispersion liquid of component (iv) + component (v) | Substituted with water | 9.6 | L30D55 | 60.6 | NE30D | 20.2 | EG48P | 9.6 |
| Reference Example 2-9 | Component (i) + dispersion liquid of component (iv) | 90SH4000SR | 9.6 | Substituted with water | 60.6 | NE30D | 20.2 | Substituted with water | 9.6 |
| Reference Example 2-10 | Component (i) + component (v) | 90SH4000SR | 9.6 | Substituted with water | 60.6 | Substituted with water | 20.2 | EG48P | 9.6 |
| Reference Example 2-11 | Component (i) + dispersion liquid of component (iv) + component (v) | 90SH4000SR | 9.6 | Substituted with water | 60.6 | NE30D | 20.2 | EG48P | 9.6 |
| Reference Example 2-12 | Component (i) + dispersion liquid of component (ii) (without neutralizer) | 90SH4000SR | 9.6 | L30D55 | 60.6 | Substituted with water | 20.2 | Substituted with water | 9.6 |
| Reference Example 2-13 | Component (i) + component (ii) (completely neutralized and dissolved) | 90SH4000SR | 9.6 | L30D55 | 60.6 | Substituted with water | 20.2 | Substituted with water | 9.6 |
| Reference Example 2-14 | Component (i) + dispersion liquid of component (ii) (partially neutralized) | 90SH4000SR | 9.6 | L30D55 | 60.6 | Substituted with water | 20.2 | Substituted with water | 9.6 |
| Reference Example 2-15 | Component (i) + dispersion liquid of component (ii) (partially neutralized) + component (iv) | 90SH4000SR | 9.6 | L30D55 | 60.6 | NE30D | 20.2 | Substituted with water | 9.6 |
| Reference Example 2-16 | All components (component (ii) completely neutralized and dissolved) | 90SH4000SR | 9.6 | L30D55 | 60.6 | NE30D | 20.2 | EG48P | 9.6 |

| | Basic neutralizer | | Degree of neutralization (%) With respect to component (ii) | Polymer solid content concentration (%) | Gelation in the vicinity of room temperature | Abrupt increase in viscosity at 30° C. to 50° C. | Independent dried film formation |
|---|---|---|---|---|---|---|---|
| | Substance name | δ (%) | | | | | |
| Example 7 | NaOH | 1.0 | 7.8 | 18.3 | ○ | ○ | ○ |
| Reference Example 2-1 | NaOH | 0.0 | 0.0 | | x | ○ | ○ |
| Reference Example 2-2 | NaOH | 0.0 | 0.0 | | x | x | x |
| Reference Example 2-3 | NaOH | 0.0 | 0.0 | | x | x | ○ |
| Reference Example 2-4 | NaOH | 0.0 | 0.0 | | x | x | ○ |
| Reference Example 2-5 | NaOH | 0.0 | 0.0 | | x | x | ○ |
| Reference Example 2-6 | NaOH | 0.0 | 0.0 | | x | x | ○ |
| Reference Example 2-7 | NaOH | 0.0 | 0.0 | | x | x | ○ |
| Reference Example 2-8 | NaOH | 0.0 | 0.0 | | x | x | ○ |

TABLE 9-continued

| | | | | | | | |
|---|---|---|---|---|---|---|---|
| Reference Example 2-9 | NaOH | 0.0 | 0.0 | | x | x | ○ |
| Reference Example 2-10 | NaOH | 0.0 | 0.0 | | x | x | ○ |
| Reference Example 2-11 | NaOH | 0.0 | 0.0 | | x | x | ○ |
| Reference Example 2-12 | NaOH | 0.0 | 0.0 | Aggregation immediately after mixing | | | |
| Reference Example 2-13 | NaOH | 13.0 | 99.9 | | x | x | x |
| Reference Example 2-14 | NaOH | 1.0 | 7.8 | | ○ | ○ | x |
| Reference Example 2-15 | NaOH | 1.0 | 7.8 | | ○ | ○ | ○ |
| Reference Example 2-16 | NaOH | 13.0 | 99.9 | | x | x | ○ |

Regarding the capsule-preparing solution (Example 7) according to the present disclosure containing all the HPMC serving as the component (i), the dispersion liquid of Eudragit L30D55 serving as the component (ii), combination of two kinds of the components (iv), and the basic neutralizer, and solutions of Reference Examples 2-1 to 2-16 lacking in any one of the components, dynamic viscoelasticity behaviors at a time of a decrease in temperature were compared with each other. The conditions of Example 7 containing all the components are the same as in Example 6-2 except that titanium oxide is eliminated. The cases in which an eliminated component was simply substituted with water in the same mass as that of the eliminated component based on the case in which titanium oxide was eliminated from Example 6-2 were defined as Reference Examples 2-1 to 2-16.

In the case of the dispersion liquid in which the component (i) was partially dissolved (Reference Example 2-1), an increase in viscosity was observed at 30° C. to 50° C., but gelation (G'>G") in the vicinity of room temperature was not exhibited. In each of the cases of the dispersion liquid of the component (ii) alone (Reference Example 2-2), the dispersion liquid of the component (iv) alone (Reference Example 2-3), and the solution of the component (v) alone (Reference Example 2-4), liquid behavior was substantially completely exhibited over the entire temperature region, and G' and G" were both significantly small and less than about 100 mPa·s over a temperature range of from 55° C. to room temperature. Specifically, neither an appropriate increase in viscosity in a temperature decrease process nor cold gelation ability in the vicinity of room temperature was exhibited. Further, also in the mixed solution of the other two components excluding the component (i) (Reference Examples 2-5, 2-6, and 2-7) or the three components (Reference Example 2-8), the mixed solution of the component (i) and the component (iv) (Reference Example 2-9), the mixed solution of the component (i) and the component (v) (Reference Example 2-10), and the mixed solution of the component (i), the component (iv), and the component (v) (Reference Example 2-11), neither an appropriate increase in viscosity in a temperature decrease process nor cold gelation ability was exhibited.

When only the component (i) and the dispersion liquid of the component (ii) without a basic neutralizer (degree of neutralization: 0%) were contained (Reference Example 2-12), significant aggregation occurred immediately after mixing of both the components, and hence this case was unsuitable as a capsule-preparing solution. This phenomenon was not influenced by the presence of the component (iv) or the component (v). When the component (i) and the component (ii) were contained, but the component (ii) was completely neutralized with a neutralizer (Reference Example 2-13 and Reference Example 2-16), a slight increase in viscosity was observed at a time of a decrease in temperature. However, the viscosity was significantly low (about 100 mPa·s or less) as a whole, and G'<G" remained established, with the result that preferred cold gelation characteristics were lost. Only when the component (i) and the component (ii) having a degree of neutralization of 7.8% were mixed with each other (Reference Examples 2-14 and 2-15), appropriate cold gelation characteristics were obtained. From the foregoing, it was considered that it was important that all the component (i), the component (ii), and the basic neutralizer capable of partially neutralizing the component (ii) were contained in a capsule-preparing solution for preparing an enteric hard capsule. In particular, in the case where the enteric polymer is formed only of the enteric methacrylic acid copolymer, when the degree of neutralization is higher than about 25%, G'<G" is established, and cold gel characteristics are liable to be lost.

Needless to say, the enteric property of the film after being dried cannot be guaranteed without the presence of the component (ii) serving as the enteric polymer. In addition, even when the component (i), the component (ii), and an appropriate amount of the basic neutralizer are present (Reference Example 2-14), the film after being dried is significantly brittle. When NE30D serving as the component (iv) was contained (Reference Example 2-15), independent film formation was able to be realized. When the entire component (iv) is substituted with the component (v), the dissolution after 2 hours at pH 1.2 is increased, and the enteric property is liable to be lost. Through use of the combination of the component (iv) and the component (v), the mechanical characteristics, in particular, ease of cracking of the film were improved without impairing the enteric property.

Besides the foregoing, also when HPMC was used as the component (i) and FS30D was used as the component (ii), and when MC or HPC was used as the component (i) and L30D55 was used as the component (ii), in accordance with Reference Examples 2-12, 2-13, and 2-14, the following was able to be confirmed. When the degree of neutralization was zero, aggregation occurred immediately after mixing of the component (i) and the component (ii) (colloid dispersion liquid). When the degree of neutralization was 100%, cold gelation performance was not exhibited. Specifically, it is required to appropriately regulate the degree of neutralization within a range of from 2% to 20% in order to obtain the cold gelation performance of the capsule-preparing solution.

3. Example 8

An example of the enteric hard capsule containing all the first to fourth components and an example of the enteric hard capsule containing all the first to fifth components are shown in Table 10 as Examples 8-1 and 8-2, respectively. A capsule-preparing solution was prepared in accordance with Preparation Example III-1 (preparation method of the embodiment 3-1). Molding was performed by the molding method IV. When a total mass of solid contents (total polymer solid content mass) of the component (i) (first component), the component (ii) (second component), the component (iii) (third component), the component (iv) (fourth component), and the component (v) (fifth component) was set to 100 mass %, the ratios of the component (i), the component (ii), the component (iii), the component (iv), and the component (v) in terms of mass % were represented by $\alpha$, $\beta$, $\gamma$, $\sigma$, and $\varphi$, respectively. Mass ratios of a basic neutralizer (NaOH) and titanium oxide (light-shielding agent) with respect to the above-mentioned total polymer solid content mass were represented by $\delta$ (%) and $\varepsilon$ (%), respectively. In addition, a mass ratio of the solid contents of the components (i) to (v) with respect to a total mass of purified water serving as a solvent and the solid contents of the components (i) to (iii) was defined as a polymer solid content concentration (%). Each specific composition is shown in Table 10. In addition, the degree of neutralization (with respect to the component (iii)) in the table refers to a degree of neutralization of the neutralization and dissolution of the component (iii) in the step A of the preparation method. Basically, the case in which the degree of neutralization of the component (iii) in the step A is 100% is defined as complete neutralization. Only in the case of Example 8-1 in which ammonia is used as a basic neutralizer, ammonia is added in excess in consideration of volatility, but a residue in the final film is estimated to be significantly smaller than 100%.

In any case, sufficient dissolution characteristics and mechanical strength as the enteric hard capsule were obtained.

TABLE 10

| | First Component | | Second Component | | Third Component | | Fourth Component Methacrylic acid alkyl | | Fifth Component PVA, | | Basic neutralizer |
|---|---|---|---|---|---|---|---|---|---|---|---|
| | HPMC | α (%) | Methacrylic acid copolymer | β (%) | Enteric cellulose compound | γ (%) | ester copolymer | σ (%) | plasticizer, etc. | φ (%) | Substance name |
| Example 8-1 | 60SH10000 | 17.5 | L30D55 | 10.3 | HPMCAS-MG | 51.5 | NE30D | 20.6 | None | 0 | Ammonia |
| Example 8-2 | 60SH10000 | 15 | L30D55 | 26.2 | HP50 | 26.2 | NE30D | 26.2 | EG48P | 6.4 | NaOH |

| | Basic neutralizer δ (%) | Degree of neutralization (%) With respect to third component | Degree of neutralization (%) With respect to enteric polymer | Others Substance name | ε (%) | Polymer solid content concentration (%) | pH 1.2 Dissolution rate after 2 hours (%) | pH 6.8 Time (min) | pH 6.8 Dissolution rate (%) |
|---|---|---|---|---|---|---|---|---|---|
| Example 8-1 | 2.84 | 273.0 | 143.3 | Titanium oxide | 3.1 | 18.8 | 2 | 60 | 90.4 |
| Example 8-2 | 1.71 | 100.4 | 23.3 | Titanium oxide | 3.1 | 21.4 | 3 | 30 | 100 |

VI. Mechanical Strength of Capsule Films in Examples 1 to 8

The hardness of a film formed into a hard capsule in each of Examples 1 to 7 had sufficient mechanical strength for keeping a stable shape as an empty hard capsule film.

Of those Examples, in each of Examples 1-1, 1-4, 1-6, 2-1, 2-2, 2-3, 2-4, 2-6, 6-1, 6-2, 6-4, and 6-6, a cast film of the same formulation was created and subjected to a tensile test. As a result, it was able to be confirmed that the elastic modulus thereof fell within a range of from 2 GPa to 5 GPa at a relative humidity of 60%. In addition, it was able to be confirmed that the capsule film had an elongation within a range of from 3% to 10% even under a condition of a relative humidity of 22% on a low humidity side, and had mechanical strength with which problems such as large deformation and cracking were not observed in usual handling. The fourth component had an effect of increasing an elongation at break to improve a cracking property of the capsule film. In addition, PVA serving as the fifth component had an effect of improving the hardness and elongation at break, that is, the cracking property of the capsule film, in particular, within a range of a relative humidity of less than 50%. In Examples 6-5 and 6-10 in which the amount of the plasticizer (PEG35000 or PG) serving as the fifth component was more than 10 mass %, the elongation at break was increased to improve the cracking property, but the hardness (elastic modulus) at a high humidity of a relative humidity of 60% was less than 2 GPa.

VII. Effect of Band Seal in Examples 1 to 8

When a band seal (for example, a seal liquid formed of a solution, in which HPMCAS-MF was dissolved in a solvent containing water and ethanol in a ratio of 2:8, was applied in a band shape to a region, in which a cap and a body of a body section of a capsule having a size of No. 2 were fitted with each other, with a width of about 5 mm and dried) was applied in the dissolution test in Examples 1 to 8, the dissolution rate was hardly influenced as compared to the case in which the band seal was not applied. The reason for this is considered as described below. The enteric hard capsule according to the present disclosure has a property of being slightly swollen in the first liquid, and this property effectively closes a gap between the cap and the body. However, in a capsule having a dissolution rate of about 10% after 2 hours from immersion in the first liquid, a decrease in dissolution rate by about 1% to about 2% is observed through application of the band seal in some cases. Therefore, when it is required to suppress dissolution more reliably, it is considered to be effective to apply the band seal.

VII. Example 9

A capsule formulation in which acetaminophen mixed powder was filled into the enteric hard capsule (size: No. 2) of Example 1-1 according to the present disclosure was prepared and used as an internal capsule. A capsule formulation having a double-capsule structure in which 100 mg of caffeine and the above-mentioned internal capsule were filled into a hypromellose capsule (Quali-V (trademark), size: No. 00) was prepared. A dissolution test was performed for 2 hours in the first liquid, and then a dissolution test was performed in the second liquid. Changes in the dissolution rates of caffeine and acetaminophen over time are shown in FIG. 8. Only the hypromellose capsule having no pH dependency was dissolved in the first liquid, and only caffeine that was a content was eluted by about 100% within a short period of time. However, the enteric hard capsule according to the present disclosure on the inner side was not dissolved, and hence the elution of acetaminophen was substantially zero. After transfer to the second liquid, dissolution started rapidly, and acetaminophen was eluted by 100% within about 30 minutes.

The invention claimed is:

1. An enteric hard capsule, comprising a film containing a first component and a second component, and further containing at least one component selected from the group consisting of a third component, and a fourth component,
   wherein the first component is a nonionic water-soluble cellulose compound having a viscosity value within a range of from 100 mPa·s to 100,000 mPa·s,
   the viscosity value is obtained by measuring a viscosity value of a 2 mass % aqueous solution of the nonionic water-soluble cellulose compound at 20° C.±0.1° C. using an Ubbelohde method in the case of the viscosity value of less than 600 mPa·s or a Brookfield type viscometer in the case of the viscosity value of 600 mPa·s or more, and
   the nonionic water-soluble cellulose compound is at least one kind selected from the group consisting of hydroxypropyl methylcellulose, methylcellulose, and hydroxypropyl cellulose;
   the second component is at least one enteric methacrylic acid copolymer selected from the group consisting of a copolymer of methacrylic acid, methyl methacrylate and methyl acrylate; a copolymer of methacrylic acid and ethyl acrylate; and salts thereof which are pharmaceutically acceptable or acceptable as a food additive, wherein the enteric methacrylic acid copolymer contains 5 mass % to 70 mass % of a methacrylic acid monomer unit when the total number of units or total number of groups of monomers forming the copolymer is set to 100 mass %;
   the third component is at least one enteric cellulose compound selected from the group consisting of hydroxypropyl methylcellulose phthalate, hydroxypropyl methylcellulose acetate succinate, cellulose acetate phthalate, and salts thereof which are pharmaceutically acceptable or acceptable as a food additive; and
   the fourth component is a water-insoluble (meth) acrylic acid alkyl ester copolymer which is a copolymer of methyl methacrylate and ethyl acrylate, wherein the water-insoluble (meth) acrylic acid alkyl ester copolymer is formed of 20 mass % to 40 mass % of methyl methacrylate and 60 mass % to 80 mass % of ethyl acrylate,
   the film optionally comprises at least one component selected from the group consisting of polyvinyl alcohol, triethyl citrate, polyethylene glycol, and propylene glycol,
   wherein the enteric hard capsule is prepared by a cold gelation method, and the method comprises:
   immersing a mold pin in an enteric hard capsule-preparing solution, the mold pin having a surface temperature lower than a temperature of the enteric hard capsule-preparing solution; and
   pulling up the mold pin from the enteric hard capsule-preparing solution and drying the enteric hard capsule-preparing solution adhering to the mold pin,
   wherein the enteric hard capsule-preparing solution comprises the first component, the second component, at least one component selected from the group consisting of the third component and the fourth component, a basic neutralizer that is pharmaceutically acceptable or is acceptable as a food additive, and a solvent, and optionally comprises at least one component selected from the group consisting of polyvinyl alcohol, triethyl citrate, polyethylene glycol, and propylene glycol.

2. The enteric hard capsule according to claim 1, wherein the enteric methacrylic acid copolymer is a copolymer containing from 40 mass % to 60 mass % of methacrylic acid and from 60 mass % to 40 mass % of ethyl acrylate.

3. The enteric hard capsule according to claim 1, wherein, when a total mass of the first component, the second component, the third component, the fourth component, and a total of the optional components contained in the film is set to 100 mass %, and when a ratio of the first component is represented by α mass %, a ratio of the second component is represented by β mass %, a ratio of the third component is represented by γ mass %, a ratio of the fourth component is represented by σ mass %, and a ratio of the total of the optional components is represented by φ mass %,
wherein a ratio of (β+γ+σ) to (α+β+γ+σ+φ) is in the range from 0.5 to 0.9, and
wherein a ratio of (β+γ) to (β+γ+σ) is 0.4 or more.

4. The enteric hard capsule according to claim 1, wherein, when a total mass of the first component, the second component, the third component, the fourth component, and a total of the optional components contained in the film is set to 100 mass %, and when a ratio of the first component is represented by α mass %, a ratio of the second component is represented by β mass %, a ratio of the third component is represented by γ mass %, a ratio of the fourth component is represented by σ mass %, and a ratio of the total of the optional components is represented by φ mass %,
wherein a ratio of α to (α+β+γ+σ+φ) is in the range from 0.05 to 0.5.

5. The enteric hard capsule according to claim 1, wherein, when a total mass of the first component, the second component, the third component, the fourth component, and a total of the optional components contained in the film is set to 100 mass %, and when a ratio of the second component is represented by β mass % and a ratio of the third component is represented by γ mass %,
wherein a ratio of β to (β+γ) is in the range from 0.1 to 1.

6. The enteric hard capsule according to claim 5, wherein, when the total mass of the first component, the second component, the third component, the fourth component, and the total of the optional components contained in the film is set to 100 mass %, and when the ratio of the first component is represented by α mass %, the ratio of the second component is represented by β mass %, the ratio of the fourth component is represented by σ mass %, and the ratio of the total of the optional components is represented by φ mass %,
wherein the ratio of the third component is 0 mass %, and
wherein a ratio of β to (α+β+γ+σ+φ) is in the range from 0.3 to 0.7.

7. The enteric hard capsule according to claim 1, wherein at least a part of the second component is contained as the salt of the second component, which is pharmaceutically acceptable or is acceptable as the food additive, and/or at least a part of the third component is contained as the salt of the third component, which is pharmaceutically acceptable or is acceptable as the food additive.

8. The enteric hard capsule according to claim 7, wherein, when a total molar number of carboxyl groups forming the salts in the second component and/or the third component contained in the film and carboxyl groups prevented from forming the salts is set to 100 mol %, a content of the carboxyl groups forming the salts is from 2 mol % to 50 mol %.

9. The enteric hard capsule according to claim 1, wherein the film has a thickness of from 50 μm to 250 μm.

10. The enteric hard capsule according to claim 9, wherein the film has an elastic modulus of from 1 GPa to 5 GPa at 25° C. and a relative humidity of 60%, and the elastic modulus is measured by preparing a sample film having a dumbbell shape of 5 mm×75 mm and a thickness of 100 μm; setting both ends of the sample film on a holder of a compact tabletop testing machine, EZ-LX manufactured by Shimadzu Corporation, with gap length of 60 mm; performing a tensile test by pulling the sample film at a tensile rate of 10 mm/min thereby obtaining an elongation of the sample film and a curve between a stress that occurs in the sample film and an elongation rate; and determining the elastic modulus from an inclination of the curve in an elastic deformation region at a time of a low stress.

11. The enteric hard capsule according to claim 9, wherein the film has an elongation at break of from 2% to 30% at 25° C. and a relative humidity of 22%, and the elongation at break is obtained by preparing a sample film having a dumbbell shape of 5 mm×75 mm and a thickness of 100 μm; setting both ends of the sample film on a holder of a compact tabletop testing machine, EZ-LX manufactured by Shimadzu Corporation, with gap length of 60 mm; and performing a tensile test by pulling the sample film at a tensile rate of 10 mm/min thereby obtaining an elongation rate at a breakpoint as the elongation at break.

12. The enteric hard capsule according to claim 1, wherein the film of the enteric hard capsule has a structure in which a phase containing the first component is dispersed in a phase formed of the second component,
the phase containing the first component optionally comprises the third component, and
the phase formed of the second component optionally comprises the first component, the fourth component, polyvinyl alcohol, triethyl citrate, polyethylene glycol, and/or propylene glycol.

13. The enteric hard capsule according to claim 1, wherein, in a dissolution test using a solution having a pH of 1.2, a dissolution ratio of the enteric hard capsule after two hours is 25% or less, and the dissolution ratio is measured by filling 40 mg of acetaminophen, 140 mg of lactose, and 20 mg of sodium starch glycolate into one capsule to obtain a sample of an enteric hard capsule formulation; preparing the solution having the pH of 1.2 by adding 7.0 ml of hydrochloric acid and water to 2.0 g of sodium chloride to obtain 1,000 ml of a liquid; and measuring absorbance at 244 nm, when the sample is immersed in the solution having the pH of 1.2 at 37° C.±0.5° C. for 2 hours, and determining the dissolution rate of acetaminophen, wherein an absorbance at 244 nm when the same volume of acetaminophen is separately dissolved in the solution having a pH of 1.2 is set to 100%.

14. The enteric hard capsule according to claim 13, wherein the dissolution ratio of the enteric hard capsule in the dissolution test is 10% or less.

15. An enteric hard capsule formulation, comprising the enteric hard capsule of claim 1 sealed with a band seal,
wherein the band seal comprises the enteric methacrylic acid copolymer of the second component and/or the enteric cellulose compound of the third component.

16. A hard capsule formulation, comprising the enteric hard capsule of claim 1 in a hard capsule that is dissolvable under an acidic condition.

17. The enteric hard capsule according to claim 1, further optionally comprising dioctyl adipate, polyester adipate, epoxidized soybean oil, an epoxyhexahydrophthalic acid diester, kaolin, glycerin, a glycerin fatty acid ester, sesame oil, a dimethyl polysiloxane-silicon dioxide mixture, D-sorbitol, a medium-chain fatty acid triglyceride, corn starch-derived sugar alcohol liquid, triacetin, concentrated glycerin, castor oil, phytosterol, diethyl phthalate, dioctyl phthalate, dibutyl phthalate, butyl phthalyl butyl glycolate, polyoxyethylene 105 polyoxypropylene 5 glycol, polysorbate 80, macrogol, isopropyl myristate, a cotton seed oil-soybean oil mixture, glycerin monostearate, and/or isopropyl linoleate.

18. The enteric hard capsule according to claim 1, further optionally comprising benzalkonium chloride, benzethonium chloride polyoxyethylene 40 monostearate, sorbitan sesquioleate, polyoxyethylene 20 sorbitan monooleate, glyceryl monostearate, sodium lauryl sulfate, polyoxyethylene lauryl ether, a sodium alkyl benzene sulfonate, a sucrose fatty acid ester, polyethylene glycol monooleate, polyethylene glycol dioleate, a propylene glycol fatty acid ester, polyoxyethylene hydrogenated castor oil, polyoxyethylene glycerin monostearate, polyoxyethylene 160 polyoxypropylene 30 glycol, and/or polyoxyethylene nonylphenyl ether.

* * * * *